United States Patent
Nakatani et al.

(10) Patent No.: US 7,875,606 B2
(45) Date of Patent: Jan. 25, 2011

(54) IZOXAZOLINE DERIVATIVE AND HERBICIDE

(75) Inventors: Masao Nakatani, Shizuoka (JP); Minoru Ito, Shizuoka (JP); Kyoko Kimijima, Shizuoka (JP); Masahiro Miyazaki, Shizuoka (JP); Makoto Fujinami, Shizuoka (JP); Ryohei Ueno, Shizuoka (JP); Satoru Takahashi, Shizuoka (JP)

(73) Assignees: Ihara Chemical Industry Co., Ltd., Tokyo (JP); Kumiai Chemical Industry Co., Ltd., Tokyo (JP)

( * ) Notice: Subject to any disclaimer, the term of this patent is extended or adjusted under 35 U.S.C. 154(b) by 1939 days.

(21) Appl. No.: 10/480,376

(22) PCT Filed: Jun. 20, 2002

(86) PCT No.: PCT/JP02/06183

§ 371 (c)(1), (2), (4) Date: Jun. 12, 2004

(87) PCT Pub. No.: WO03/000686

PCT Pub. Date: Jan. 3, 2003

(65) Prior Publication Data

US 2004/0259734 A1    Dec. 23, 2004

(30) Foreign Application Priority Data

Jun. 21, 2001    (JP) .............................. 2001-187679

(51) Int. Cl.
*A61K 31/541* (2006.01)
*A61K 31/496* (2006.01)
*C07D 417/02* (2006.01)
*C07D 413/02* (2006.01)

(52) U.S. Cl. ............. 514/227.8; 514/235.5; 514/254.02; 514/326; 514/380; 548/243; 544/137; 544/367

(58) Field of Classification Search ............... 514/227.8, 514/235.5, 254.02, 326, 328; 548/243; 544/137, 544/367
See application file for complete search history.

(56) References Cited

U.S. PATENT DOCUMENTS 7,238,689 B2 *    7/2007    Nakatani et al. ......... 514/227.8

FOREIGN PATENT DOCUMENTS

| EP | 1 203 768 | 9/2000 |
|---|---|---|
| EP | 1 364 946 | 11/2003 |
| JP | 5-105672 | 4/1993 |
| JP | 05-105672 | 4/1993 |
| JP | 9-328483 | 12/1997 |
| JP | 09-328483 | 12/1997 |
| WO | 03/010165 | 2/2003 |

OTHER PUBLICATIONS

Dorwald F. A. Side Reactions in Organic Synthesis, 2005, Wiley: VCH, Weinheim p. IX of Preface.*

* cited by examiner

*Primary Examiner*—Sabiha Qazi
(74) *Attorney, Agent, or Firm*—Bacon & Thomas, PLLC

(57) ABSTRACT

The present invention aims at providing an isoxazoline derivative and a pharmaceutically acceptable salt thereof, both having an excellent herbicidal effect and an excellent selectivity between crop and weed.

The isoxazoline derivative of the present invention is represented by the following general formula:

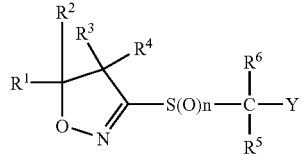

wherein $R^1$ is a haloalkyl group; $R^2$ is a hydrogen atom, an alkyl group, or the like; $R^3$, $R^4$, $R^5$ and $R^6$ are each a hydrogen atom, or the like; Y is a pyrrolyl group, a pyrazolyl group, an isothiazolyl group, an oxazolyl group, an imidazolyl group, a pyridazinyl group, a pyrimidinyl group, a pyrazinyl group, a triazinyl group, a triazolyl group, an oxadiazolyl group, or the like; and n is an integer of 0 to 2.

6 Claims, No Drawings

IZOXAZOLINE DERIVATIVE AND HERBICIDE

CROSS-REFERENCE TO RELATED APPLICATIONS

This application is a National Phase Application (35 USC 371) of PCT/JP02/006183 and claims priority of Japanese Application No. 2001-187679, filed Jun. 21, 2001.

TECHNICAL FIELD

The present invention relates to a novel isoxazoline derivative and a herbicide containing the isoxazoline derivative as an active ingredient.

BACKGROUND ART

The herbicidal activities of isoxazoline derivatives having a haloalkyl group at the 5-position of the isoxazoline ring are reported in, for example, JP-A-8-225548, JP-A-9-328477 and JP-A-9-328483. The compound of the present invention, however, is not described in these literatures.

Herbicides applied to useful crops are desired, when applied to soil or stems and leaves, to show a sufficient herbicidal effect at a low ingredient amount and, moreover, exhibit a high selectivity between crop and weed. In these respects, the compounds described in the above literatures are not fully satisfactory.

In view of the above situation, the present inventors made a study on the herbicidal effect and selectivity between crop and weed, of various compounds. As a result, the present inventors found out that a novel isoxazoline derivative has an excellent herbicidal effect and an excellent selectivity between crop and weed. The above finding has led to the completion of the present invention.

DISCLOSURE OF THE INVENTION

The present invention provides the followings.

(1) An isoxazoline derivative having the following general formula [I] and a pharmaceutically acceptable salt thereof:

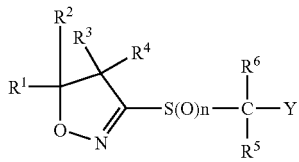

wherein $R^1$ is a C1 to C4 haloalkyl group;

$R^2$ is a hydrogen atom, a C1 to C10 alkyl group, a C1 to C4 haloalkyl group, a C3 to C8 cycloalkyl group, or a C3 to C8 cycloalkyl C1 to C3 alkyl group;

$R^3$ and $R^4$ may be the same or different and are each a hydrogen atom, a C1 to C10 alkyl group or a C3 to C8 cycloalkyl group; or $R^3$ and $R^4$ may be bonded to each other to form a C3 to C7 spiro ring together with the carbon atom to which they bond; or $R^2$ and $R^3$ may be bonded to each other to form a 5- to 8-membered ring together with the carbon atoms to which they bond;

$R^5$ and $R^6$ may be the same or different and are each a hydrogen atom or a C1 to C10 alkyl group;

Y is a pyrrolyl group, a pyrazolyl group, an isothiazolyl group, an oxazolyl group, an imidazolyl group, a pyridazinyl group, a pyrimidinyl group, a pyrazinyl group, a triazinyl group, a triazolyl group, an oxadiazolyl group, a benzothienyl group, an indolyl group, a benzoxazolyl group, a benzimidazolyl group, a benzoisoxazolyl group, a benzoisothiazolyl group, an indazolyl group, a quinolyl group, an isoquinolyl group, a phthalazinyl group, a quinoxalinyl group, a quinazolinyl group, a cinnolinyl group or a benzotriazolyl group (in these heterocyclic groups, when the hetero atom is a nitrogen atom, the nitrogen atom may be oxidized to form an N-oxide); these heterocyclic groups may each be substituted with one to six same or different groups selected from the following substituent group a (when the heterocyclic group is substituted at the two adjacent positions with two alkyl groups, two alkoxy groups, an alkyl group and an alkoxy group, an alkyl group and an alkylthio group, an alkyl group and an alkylsulfonyl group, an alkyl group and a monoalkylamino group, or an alkyl group and a dialkylamino group, the two groups may form a 5- to 8-membered ring which may be substituted with 1 to 4 halogen atoms);

n is an integer of 0 to 2.

[Substituent Group α]

Hydroxyl group; halogen atoms; C1 to C10 alkyl groups; C1 to C10 alkyl groups each mono-substituted with a group selected from the following substituent group β, C1 to C4 haloalkyl groups; C3 to C8 cycloalkyl groups; C1 to C10 alkoxy groups; C1 to C10 alkoxy groups each mono-substituted with a group selected from the following substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfinyl groups; C1 to C10 alkylsulfonyl groups; C1 to C10 alkylsulfonyl groups each mono-substituted with a group selected from the substituent group γ; C1 to C4 haloalkylsulfinyl groups; C1 to C4 haloalkylsulfonyl groups; C1 to C10 alkylsulfonyloxy groups; C1 to C4 haloalkylsulfonyloxy groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfinyl groups; optionally substituted phenylsulfonyl groups; optionally substituted aromatic heterocyclic sulfinyl groups; optionally substituted aromatic heterocyclic sulfonyl groups; optionally substituted phenylsulfonyloxy groups; C1 to C6 acyl groups; C1 to C4 haloalkylcarbonyl groups; optionally substituted benzylcarbonyl group; optionally substituted benzoyl group; carboxyl group; C1 to C10 alkoxycarbonyl groups; optionally substituted benzyloxycarbonyl group; optionally substituted phenoxycarbonyl group; cyano group; carbamoyl group (its nitrogen atom may be substituted with same or different groups selected from C1 to C10 alkyl groups and optionally substituted phenyl group); C1 to C6 acyloxy groups; C1 to C4 haloalkylcarbonyloxy groups; optionally substituted benzylcarbonyloxy group; optionally substituted benzoyloxy group; nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl group, C1 to C4 haloalkylsulfonyl groups, optionally substituted benzylsulfonyl group, and optionally substituted phenylsulfonyl group).

[Substituent Group β]

Hydroxyl group; C3 to C8 cycloalkyl groups (which may be substituted with halogen atoms or C1 to C10 alkyl groups); C1 to C10 alkoxy groups; C1 to C10 alkylthio groups; C1 to C10 alkylsulfonyl groups; C1 to C10 alkoxycarbonyl groups; C2 to C6 haloalkenyl groups; amino group (its nitrogen atom may be substituted with same or different groups selected from C1 to C10 alkyl groups, C2 to C6 acyl groups; C1 to C4 haloalkylcarbonyl groups, C1 to C10 alkylsulfonyl groups and C1 to C4 haloalkylsulfonyl groups); carbamoyl group (its nitrogen atom may be substituted with same or different groups selected from C1 to C10 alkyl groups and optionally substituted phenyl group); C2 to C6 acyl groups; C1 to C4 haloalkylcarbonyl groups; C1 to C10 alkoxyimino groups; cyano group; optionally substituted phenyl group; and optionally substituted phenoxy group.

[Substituent Group γ]

C1 to C10 alkoxycarbonyl groups; optionally substituted phenyl group; optionally substituted aromatic heterocyclic groups; cyano group; and carbamoyl group (its nitrogen atom may be substituted with same or different C1 to C10 alkyl groups).

(2) An isoxazoline derivative or a pharmaceutically acceptable salt thereof according to (1), wherein the substituent group α is represented by hydroxyl group; halogen atoms; C1 to C10 alkyl groups; C1 to C10 alkyl groups each mono-substituted with a group selected from the substituent group β; C1 to C4 haloalkyl groups; C3 to C8 cycloalkyl groups; C1 to C10 alkoxy groups; C1 to C10 alkoxy groups each mono-substituted with a group selected from the substituent group γ; C1 to C4 haloalkoxy groups; C3 to C8 cycloalkyloxy groups; C3 to C8 cycloalkyl C1 to C3 alkyloxy groups; C1 to C10 alkylthio groups; C1 to C10 alkylthio groups each mono-substituted with a group selected from the substituent group γ; C1 to C4 haloalkylthio groups; C2 to C6 alkenyl groups; C2 to C6 alkenyloxy groups; C2 to C6 alkynyl groups; C2 to C6 alkynyloxy groups; C1 to C10 alkylsulfonyl groups; C1 to C4 haloalkylsulfonyl groups; optionally substituted phenyl group; optionally substituted phenoxy group; optionally substituted phenylthio group; optionally substituted aromatic heterocyclic groups; optionally substituted aromatic heterocyclic oxy groups; optionally substituted aromatic heterocyclic thio groups; optionally substituted phenylsulfonyl groups; optionally substituted aromatic heterocyclic sulfonyl groups; C1 to C6 acyl groups; C1 to C4 haloalkylcarbonyl groups; optionally substituted benzylcarbonyl group; optionally substituted benzoyl group; carboxyl group; C1 to C10 alkoxycarbonyl groups; cyano group; carbamoyl group (its nitrogen atom may be substituted with same or different groups selected from C1 to C10 alkyl groups and optionally substituted phenyl group); nitro group; and amino group (its nitrogen atom may be substituted with same or different groups selected from C1 to C10 alkyl groups, optionally substituted phenyl group, C1 to C6 acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group, and optionally substituted phenylsulfonyl group).

(3) An isoxazoline derivative or a pharmaceutically acceptable salt thereof according to (2), wherein the substituent group a is represented by halogen atoms; C1 to C10 alkyl groups; C1 to C4 haloalkyl groups; C1 to C10 alkoxy C1 to C3 alkyl groups; C3 to C8 cycloalkyl groups (which may be substituted with halogen atom or alkyl group); C1 to C10 alkoxy groups; C1 to C4 haloalkoxy groups; C3 to C8 cycloalkyl C1 to C3 alkyloxy groups; optionally substituted phenoxy group; C1 to C10 alkylthio groups; C1 to C10 alkylsulfonyl groups; acyl groups; C1 to C4 haloalkylcarbonyl groups; C1 to C10 alkoxycarbonyl groups; cyano group and carbamoyl group (its nitrogen atom may be substituted with same or different C1 to C10 alkyl groups).

(4) An isoxazoline derivative or a pharmaceutically acceptable salt thereof according to (1), (2) or (3), wherein $R^1$ is a chloromethyl group; $R^2$ is a methyl group or an ethyl group; $R^3$, $R^4$, $R^5$ and $R^6$ are each a hydrogen atom.

(5) An isoxazoline derivative or a pharmaceutically acceptable salt thereof according to (1), (2), (3) or (4), wherein Y is a pyrrolyl group, a pyrazolyl group, an isothiazolyl group, an oxazolyl group, an imidazolyl group, a pyridazinyl group, a pyrimidinyl group, a pyrazinyl group, a triazinyl group, a triazolyl group or an oxadiazolyl group.

(6) An isoxazoline derivative or a pharmaceutically acceptable salt thereof according to (5), wherein Y is a pyrazolyl group or a pyrimidinyl group.

(7) An isoxazoline derivative or a pharmaceutically acceptable salt thereof according to (6), wherein Y is a pyrazol-4-yl group or a pyrimidin-5-yl group.

(8) An isoxazoline derivative or a pharmaceutically acceptable salt thereof according to (7), wherein Y is a pyrazol-4-yl group and the pyrazole ring is substituted at the 3- and 5-positions with a group selected from the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group, a C1 to C10 alkylsulfinyl group, a C1 to C10 alkylsulfonyl group, a C1 to C10 alkylsulfonyl group mono-substituted with a group selected from the substituent group γ, a C1 to C4 haloalkylsulfonyl group, an optionally substituted phenyl group, an optionally substituted aromatic heterocyclic group, an optionally substituted phenylsulfonyl group, an optionally substituted aromatic heterocyclic sulfonyl group, an acyl group, a C1 to C4 haloalkylcarbonyl group, an optionally substituted benzylcarbonyl group, an optionally substituted benzoyl group, a C1 to C10 alkoxycarbonyl group, an optionally substituted benzyloxycarbonyl group, an optionally substituted phenoxycarbonyl group, a carbamoyl group (its nitrogen atom may be substituted with same or different groups selected from C1 to C10 alkyl groups and optionally substituted phenyl group), or an amino group (its nitrogen atom may be substituted with same or different groups selected from C1 to C10 alkyl groups, optionally substituted phenyl group, acyl groups, C1 to C4 haloalkylcarbonyl groups, optionally substituted benzylcarbonyl group, optionally substituted benzoyl group, C1 to C10 alkylsulfonyl groups, C1 to C4 haloalkylsulfonyl groups, optionally substituted benzylsulfonyl group and optionally substituted phenylsulfonyl group).

(9) An isoxazoline derivative or a pharmaceutically acceptable salt thereof according to (7), wherein Y is a pyrimidin-5-yl group and the pyrimidine ring are substituted with a group selected from the substituent group α, at the 4- and 6-positions.

(10) A herbicide containing, as an active ingredient, an isoxazoline derivative or a pharmaceutically acceptable salt thereof according to any of (1) to (9).

The definitions of the terms used in the present specification are given below.

The expression of "C1 to C10", etc. indicates that the substituent appearing after the expression has 1 to 10 carbon atoms in the case of "C1 to C10".

Halogen atom refers to a fluorine atom, a chlorine atom, a bromine atom or an iodine atom.

C1 to C10 alkyl group refers, unless otherwise specified, to a straight or branched chain alkyl group of 1 to 10 carbon atoms; and there can be mentioned, for example, methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, 3,3-dimethylbutyl group, heptyl group and octyl group.

C3 to C8 cycloalkyl group refers to a cycloalkyl group of 3 to 8 carbon atoms; and there can be mentioned, for example, cyclopropyl group, cyclobutyl group, cyclopentyl group and cyclohexyl group.

C3 to C8 cycloalkyl C1 to C3 alkyl group (which may be substituted with halogen atom or alkyl group) refers, unless otherwise specified, to a C1 to C3 alkyl group substituted with a C3 to C8 cycloalkyl group which may be substituted with 1 to 4 same or different halogen atoms or C1 to C3 alkyl group; and there can be mentioned, for example, cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group, cyclohexylmethyl group, 2-chlorocyclopropylmethyl group, 2,2-dichlorocyclopropylmethyl group, 2-fluorocyclopropylmethyl group, 2,2-difluorocyclopropylmethyl group, 2-methylcyclopropylmethyl group, 2,2-dimethylcyclopropylmethyl group and 2-methylcyclopropylethyl group.

C3 to C8 cycloalkyl C1 to C3 alkyl group refers to a alkyl group of 1 to 3 carbon atoms, substituted with a cycloalkyl group of 3 to 8 carbon atoms; and there can be mentioned, for example, cyclopropylmethyl group, 1-cyclopropylethyl group, 2-cyclopropylethyl group, 1-cyclopropylpropyl group, 2-cyclopropylpropyl group, 3-cyclopropylpropyl group, cyclobutylmethyl group, cyclopentylmethyl group and cyclohexylmethyl group.

C1 to C4 haloalkyl group refers, unless otherwise specified, to a straight or branched chain alkyl group of 1 to 4 carbon atoms, substituted with 1 to 9 same or different halogen atoms; and there can be mentioned, for example, fluoromethyl group, chloromethyl group, bromomethyl group, difluoromethyl group, trifluoromethyl group, 2,2-difluoroethyl group, 2,2,2-trifluoroethyl group and pentafluoroethyl group.

C2 to C6 alkenyl group refers to a straight or branched chain alkenyl group of 2 to 6 carbon atoms; and there can be mentioned, for example, ethenyl group, 1-propenyl group, 2-propenyl group, isopropenyl group, 1-butenyl group, 2-butenyl group, 3-butenyl group and 2-pentenyl group.

C2 to C6 alkynyl group refers to a straight or branched chain alkynyl group of 2 to 6 carbon atoms; and there can be mentioned, for example, ethynyl group, 2-propynyl group, 1-methyl-2-propynyl group, 2-butynyl group, 3-butynyl group and 2-methyl-3-butynyl group.

C2 to C6 haloalkenyl group refers, unless otherwise specified, to a straight or branched alkenyl group of 2 to 6 carbon atoms, substituted with 1 to 4 same or different halogen atoms; and there can be mentioned, for example, 3-chloro-2-propenyl group and 2-chloro-2-propenyl group.

C1 to C10 alkoxy group refers to an (alkyl)-O— group wherein the alkyl moiety has the above definition; and there can be mentioned, for example, methoxy group, ethoxy group, n-propoxy group, isopropoxy group, tert-butoxy group, n-butoxy group, sec-butoxy group and isobutoxy group.

C1 to C10 alkoxy C1 to C3 alkyl group refers to an (alkyl)-O-(alkyl) group wherein the alkoxy moiety and the alkyl moiety have the above definitions; and there can be mentioned, for example, methoxymethyl group, ethoxymethyl group, methoxyethyl group and ethoxyethyl group.

C1 to C4 haloalkoxy group refers to a (haloalkyl)-O— group wherein the haloalkyl moiety has the above definition; and there can be mentioned, for example, difluoromethoxy group, trifluoromethoxy group, 2,2-difluoroethoxy group and 2,2,2-trifluoroethoxy group.

C3 to C8 cycloalkyloxy group refers to a (cycloalkyl)-O— group wherein the cycloalkyl moiety has the above definition; and there can be mentioned, for example, cyclopropyloxy group, cyclobutyloxy group, cyclopentyloxy group and cyclohexyloxy group.

C3 to C8 cycloalkyl C1 to C3 alkyloxy group refers to a (cycloalkylalkyl)-O— group wherein the cycloalkylalkyl moiety has the above definition; and there can be mentioned, for example, cyclopropylmethoxy group, 1-cyclopropylethoxy group, 2-cyclopropylethoxy group, 1-cyclopropylpropoxy group, 2-chclopropylpropoxy group, 3-cyclopropylpropoxy group, cyclobutylmethoxy group, cyclopentylmethoxy group and cyclohexylmethoxy group.

C2 to C6 alkenyloxy group and C2 to C6 alkynyloxy group refer, respectively, to an (alkenyl)-O— group and an (alkynyl)-O— group, in each of which the alkenyl or alkynyl moiety has the above definition; and there can be mentioned, for example, 2-propenyloxy group and 2-propynyloxy group.

C1 to C10 alkoxyimino group refers to an (alkoxy)-N= group wherein the alkoxy moiety has the above definition; and there can be mentioned, for example, methoxyimino group and ethoxyimino group.

C1 to C10 alkylthio group, C1 to C10 alkylsulfinyl group and C1 to C10 alkylsulfonyl group refer, respectively, to an (alkyl)-S— group, an (alkyl)-SO— group and an (alkyl)-$SO_2$— group, in each of which the alkyl moiety has the above definition; and there can be mentioned, for example, methylthio group, ethylthio group, n-propylthio group, isopropylthio group, methylsulfinyl group, methylsulfonyl group, ethylsulfonyl group, n-propylsulfonyl group and isopropylsulfonyl group.

C1 to C10 alkylsulfonyloxy group refers to an (alkylsulfonyl)-O— group wherein the alkylsulfonyl moiety has the above definition, and there can be mentioned, for example, methylsulfonyloxy group and ethylsulfonyloxy group.

C1 to C10 alkoxycarbonyl group refers to an (alkoxy)-CO— group wherein the alkoxy moiety has the above definition, and there can be mentioned, for example, methoxycarbonyl group, ethoxycarbonyl group, n-propoxycarbonyl group and isopropoxycarbonyl group.

C1 to C6 acyl group refers to a straight or branched chain aliphatic acyl group of 1 to 6 carbon atoms, and there can be mentioned, for example, formyl group, acetyl group, propionyl group, isopropionyl group, butyryl group and pivaloyl group.

C1 to C10 acyloxy group refers to an (acyl)-O— group wherein the acyl moiety has the above definition; and there can be mentioned, for example, acetoxy group, propionyloxy group, isopropionyloxy group and pivaloyloxy group.

C1 to C4 haloalkylcarbonyl group, C1 to C4 haloalkylthio group, C1 to C4 haloalkylsulfinyl group and C1 to C4 haloalkylsulfonyl group refers, respectively, to a (haloalkyl)-CO— group, a (haloalkyl)-S— group, a (haloalkyl)-SO— group and a (haloalkyl)-SO$_2$— group, in each of which the haloalkyl moiety has the above definition; and there can be mentioned, for example, chloroacetyl group, trifluoroacetyl group, pentafluoropropionyl group, difluoromethylthio group, trifluoromethylthio group, chloromethylsulfinyl group, difluoromethylsulfinyl group, trifluoromethylsulfinyl group, chloromethylsulfonyl group, difluoromethylsulfonyl group and trifluoromethylsulfonyl group.

C1 to C4 haloalkylcarbonyloxy group and C1 to C4 haloalkylsulfonyloxy group refer, respectively, to a (haloalkylcarbonyl)-O— group and a (haloalkylsulfonyl)-O— group, in each of which the haloalkylcarbonyl moiety or the haloalkylsulfonyl moiety has the above definition; and there can be mentioned, for example, chloroacetyloxy group, trifluoroacetyloxy group, chloromethylsulfonyloxy group and trifluoromehtylsulfonyloxy group.

"Optionally substituted" in (optionally substituted) phenyl group, (optionally substituted) aromatic heterocyclic group, (optionally substituted) phenoxy group, (optionally substituted aromatic heterocyclic oxy group, (optionally substituted) phenylthio group, (optionally substituted) aromatic heterocyclic thio group, (optionally substituted) phenylsulfinyl group, (optionally substituted) phenylsulfonyl group, (optionally substituted) phenylsulfonyloxy group, (optionally substituted) aromatic heterocyclic sulfinyl group, (optionally substituted) aromatic heterocyclic sulfonyl group, (optionally substituted) benzylcarbonyl group, (optionally substituted) benzylcarbonyloxy group, (optionally substituted) benzylsulfonyl group, (optionally substituted) benzoyl group, (optionally substituted) benzoyloxy group, (optionally substituted) benzyloxycarbonyl group and (optionally substituted) phenoxycarbonyl group, refers to being optionally substituted with, for example, halogen atom, C1 to C10 alkyl group, C1 to C4 haloalkyl group, C1 to C10 alkoxy C1 to C3 alkyl group, C1 to C10 alkoxy group, C1 to C10 alkylthio group, C1 to C10 alkylsulfonyl group, acyl group, C1 to C10 alkoxycarbonyl group, cyano group, carbamoyl group (its nitrogen atom may be substituted with same or different C1 to C10 alkyl groups), nitro group, or amino group (its nitrogen atom may be substituted with same or different groups selected from C1 to C10 alkyl groups, C1 to C6 acyl groups, C1 to C4 haloalkylcarbonyl groups, C1 to C10 alkylsulfonyl groups and C1 to C4 haloalkylsulfonyl groups).

Aromatic heterocycle in (optionally substituted) aromatic heterocyclic group, (optionally substituted) aromatic heterocyclic oxy group, (optionally substituted) aromatic heterocyclic thio group, (optionally substituted) aromatic heterocyclic sulfinyl group and (optionally substituted) aromatic heterocyclic sulfonyl group, refers to a 5- to 6-membered group having 1 to 3 hetero atoms randomly selected from nitrogen atom, oxygen atom and sulfur atom; and there can be mentioned, for example, furyl group, thienyl group, pyrrolyl group, pyrazolyl group, isoxazolyl group, isothiazolyl group, oxazolyl group, thiazolyl group, imidazolyl group, pyridyl group, pyridazinyl group, pyrimidinyl group, pyrazinyl group, triazinyl group, triazolyl group, oxadiazolyl group and thiadiazolyl group.

Pharmaceutically acceptable salt is a salt of a compound of the general formula [I] having, in the structure, hydroxyl group, carboxyl group, amino group or the like, with a metal or an organic base or with a mineral acid or an organic acid. As the metal, there can be mentioned alkali metals such as sodium, potassium and the like; and alkaline earth metals such as magnesium, calcium and the like. As the organic base, there can be mentioned triethylamine, diisopropylamine, etc. As the mineral acid, there can be mentioned hydrochloric acid, sulfuric acid, etc. As the organic acid, there can be mentioned acetic acid, methanesulfonic acid, p-toluenesulfonic acid, etc.

Of the compounds represented by the general formula [I], preferred is an isoxazoline derivative wherein $R^1$ is a chloromethyl group;

$R^2$ is a methyl group or an ethyl group;

$R^3$, $R^4$, $R^5$ and $R^6$ are each a hydrogen atom;

n is an integer of 2; and

Y is a pyrazol-4-yl group which is substituted, at the 3- and 5-positions, with halogen atom, alkyl group, haloalkyl group, alkoxyalkyl group, cycloalkyl group, alkoxy group, haloalkoxy group, cycloalkylalkyloxy group, optionally substituted phenoxy group, alkylthio group, alkylsulfonyl group, acyl group, haloalkylcarbonyl group, alkoxycarbonyl group, cyano group or carbamoyl group (its nitrogen atom may be substituted with same or different alkyl groups) and, at the 1-position, with hydrogen atom, alkyl group, alkyl group monosubstituted with a group selected from the substituent group β, haloalkyl group, cycloalkyl group, alkenyl group, alkynyl group, alkylsulfonyl group, alkylsulfonyl group mono-substituted with a group selected from the substituent group γ, haloalkylsulfonyl group, optionally substituted phenyl group, optionally substituted aromatic heterocyclic group, optionally substituted phenylsulfonyl group, optionally substituted aromatic heterosulfonyl group, acyl group, haloalkylcarbonyl group, optionally substituted benzylcarbonyl group, optionally substituted benzoyl group, alkoxycarbonyl group, optionally substituted benzoyloxycarbonyl group, optionally substituted phenoxycarbonyl group or carbamoyl group (its nitrogen atom may be substituted with same or different alkyl groups or optionally substituted phenyl group); or Y is a pyrimidin-5-yl group which is substituted, at the 4- and 6-positions, with halogen atom, alkyl group, haloalkyl group, alkoxyalkyl group, cycloalkyl group, alkoxy group, haloalkoxy group, alkylthio group, alkylsulfonyl group, acyl group, haloalkylcarbonyl group, alkoxycarbonyl group, cyano group or carbamoyl group (its nitrogen atom may be substituted with same or different alkyl groups).

BEST MODE FOR CARRYING OUT THE INVENTION

Next, representative examples of the present compound represented by the general formula [I] are shown in Tables 1 to 57. However, the present compound is not restricted to these examples.

The following abbreviated expressions used in the Tables of the present invention refer to the following groups.

| | |
|---|---|
| Me: methyl group | Et: ethyl group |
| Pr: n-propyl group | Pr-i: isopropyl group |
| Pr-c: cyclopropyl group | Bu: n-butyl group |
| Bu-i: isobutyl group | Bu-sec: sec-butyl group |
| Bu-t: tert-butyl group | Bu-c: cyclobutyl group |
| Pen-c: cyclopentyl group | Hex-c: cyclohexyl group |
| Ph: phenyl group | |

When the present compound of the general formula [I] contains hydroxyl group as a substituent, there may exist keto-enol tautomers. Any of these tautomers and any mixture of these tautomers are included in the present compound.

TABLE 1

| $R^1$ | $R^2$ | $R^3$ | $R^4$ | n | $R^5$ | $R^6$ | $Z^1$ | $R^{12}$ | $R^{13}$ | $R^{14}$ |
|---|---|---|---|---|---|---|---|---|---|---|
| $CH_2Cl$ | Me | H | H | 2 | H | H | N-Me | Me | H | Me |
| $CH_2Cl$ | Me | H | H | 2 | H | H | N-Me | Me | C(=O)OMe | $CH_2$C(=O)OMe |
| $CH_2Cl$ | Me | H | H | 2 | H | H | N-Me | Me | C(=O)OEt | $CH_2$C(=O)OEt |
| $CH_2Cl$ | Me | H | H | 2 | H | H | N-Me | Me | Me | Me |
| $CH_2Cl$ | Me | H | H | 2 | H | H | N-Ph | OMe | H | H |
| $CH_2Cl$ | Me | H | H | 2 | H | H | N-Ph | OEt | H | H |
| $CH_2Cl$ | Me | H | H | 2 | H | H | N-Ph | $OCHF_2$ | H | H |
| $CH_2Cl$ | Me | H | H | 1 | H | H | N-Me | Me | H | Me |
| $CH_2Cl$ | Me | H | H | 1 | H | H | N-Me | Me | C(=O)OMe | $CH_2$C(=O)OMe |
| $CH_2Cl$ | Me | H | H | 1 | H | H | N-Me | Me | C(=O)OEt | $CH_2$C(=O)OEt |
| $CH_2Cl$ | Me | H | H | 1 | H | H | N-Me | Me | Me | Me |
| $CH_2Cl$ | Me | H | H | 1 | H | H | N-Ph | OMe | H | H |
| $CH_2Cl$ | Me | H | H | 1 | H | H | N-Ph | OEt | H | H |
| $CH_2Cl$ | Me | H | H | 1 | H | H | N-Ph | $OCHF_2$ | H | H |
| $CH_2Cl$ | Me | H | H | 0 | H | H | N-Me | Me | H | Me |
| $CH_2Cl$ | Me | H | H | 0 | H | H | N-Me | Me | C(=O)OMe | $CH_2$C(=O)OMe |
| $CH_2Cl$ | Me | H | H | 0 | H | H | N-Me | Me | C(=O)OEt | $CH_2$C(=O)OEt |
| $CH_2Cl$ | Me | H | H | 0 | H | H | N-Me | Me | Me | Me |
| $CH_2Cl$ | Me | H | H | 0 | H | H | N-Ph | OMe | H | H |
| $CH_2Cl$ | Me | H | H | 0 | H | H | N-Ph | OEt | H | H |
| $CH_2Cl$ | Me | H | H | 0 | H | H | N-Ph | $OCHF_2$ | H | H |
| $CH_2Cl$ | Et | H | H | 2 | H | H | N-H | H | H | H |

TABLE 2

| $R^1$ | $R^2$ | $R^3$ | $R^4$ | n | $R^5$ | $R^6$ | $R^{15}$ | $Z^2$ | $R^{16}$ |
|---|---|---|---|---|---|---|---|---|---|
| $CH_2Cl$ | Me | H | H | 2 | H | H | H | N-Me | Cl |
| $CH_2Cl$ | Me | H | H | 2 | H | H | Me | N-Me | Me |
| $CH_2Cl$ | Me | H | H | 2 | H | H | Me | N-Me | Cl |
| $CH_2Cl$ | Me | H | H | 2 | H | H | Cl | N-Me | Cl |
| $CH_2Cl$ | Me | H | H | 2 | H | H | Cl | N-Me | $CF_3$ |
| $CH_2Cl$ | Me | H | H | 2 | H | H | $CHF_2$ | N-Me | Cl |
| $CH_2Cl$ | Me | H | H | 2 | H | H | $CF_3$ | N-Me | Cl |
| $CH_2Cl$ | Me | H | H | 2 | H | H | $CF_3$ | N-Me | CN |

TABLE 2-continued

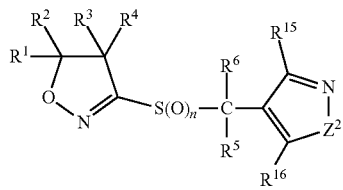

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | CF₃ | N-Me | OMe |
| CH₂Cl | Me | H | H | 2 | H | H | CF₃ | N-Me | OEt |
| CH₂Cl | Me | H | H | 2 | H | H | CF₃ | N-Me | OPr-i |
| CH₂Cl | Me | H | H | 2 | H | H | CF₃ | N-Me | OPr |
| CH₂Cl | Me | H | H | 2 | H | H | CF₃ | N-Me | OCH₂CH=CH₂ |
| CH₂Cl | Me | H | H | 2 | H | H | CF₃ | N-Me | OCH₂CF₃ |
| CH₂Cl | Me | H | H | 2 | H | H | CF₃ | N-Me | OPh |
| CH₂Cl | Me | H | H | 2 | H | H | CF₃ | N-Me | SMe |
| CH₂Cl | Me | H | H | 2 | H | H | CF₃ | N-Me | SOMe |
| CH₂Cl | Me | H | H | 2 | H | H | CF₃ | N-Me | SO₂Me |
| CH₂Cl | Me | H | H | 2 | H | H | CF₃ | N-Me | SCF₃ |
| CH₂Cl | Me | H | H | 2 | H | H | CF₃ | N-Me | SOCF₃ |
| CH₂Cl | Me | H | H | 2 | H | H | CF₃ | N-Me | SO₂CF₃ |
| CH₂Cl | Me | H | H | 2 | H | H | CF₃ | N-Me | SPh |
| CH₂Cl | Me | H | H | 2 | H | H | CF₃ | N-Me | SOPh |
| CH₂Cl | Me | H | H | 2 | H | H | CF₃ | N-Me | SO₂Ph |
| CH₂Cl | Me | H | H | 2 | H | H | CF₃ | N-Me | Ph |
| CH₂Cl | Me | H | H | 2 | H | H | CF₂CF₃ | N-Me | Cl |
| CH₂Cl | Me | H | H | 2 | H | H | CF₃ | N-H | Cl |
| CH₂Cl | Me | H | H | 2 | H | H | CF₃ | N—CH₂OH | Cl |
| CH₂Cl | Me | H | H | 2 | H | H | CF₃ | N—CH₂OMe | Cl |
| CH₂Cl | Me | H | H | 2 | H | H | CF₃ | N—CH₂CN | Cl |

TABLE 3

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | CF₃ | N—CH₂CH=CH₂ | Cl |
| CH₂Cl | Me | H | H | 2 | H | H | CF₃ | N—CH₂C≡CH | Cl |
| CH₂Cl | Me | H | H | 2 | H | H | CF₃ | N-Et | Cl |
| CH₂Cl | Me | H | H | 2 | H | H | CF₃ | N-Pr-i | Cl |
| CH₂Cl | Me | H | H | 2 | H | H | CF₃ | N-Pr | Cl |
| CH₂Cl | Me | H | H | 2 | H | H | CF₃ | N-Bu-t | Cl |
| CH₂Cl | Me | H | H | 2 | H | H | CF₃ | N—CH₂Ph | Cl |
| CH₂Cl | Me | H | H | 2 | H | H | CF₃ | N—CH₂CF₃ | Cl |
| CH₂Cl | Me | H | H | 2 | H | H | CF₃ | N—CH₂C(=O)OMe | Cl |
| CH₂Cl | Me | H | H | 2 | H | H | CF₃ | N—CH(Me)C(=O)OMe | Cl |
| CH₂Cl | Me | H | H | 2 | H | H | CF₃ | N—C(Me)₂C(=O)OMe | Cl |
| CH₂Cl | Me | H | H | 2 | H | H | CF₃ | N—CH₂CH₂SMe | Cl |
| CH₂Cl | Me | H | H | 2 | H | H | CF₃ | N—CH₂CH₂SO₂Me | Cl |
| CH₂Cl | Me | H | H | 2 | H | H | CF₃ | N—SO₂Me | Cl |
| CH₂Cl | Me | H | H | 2 | H | H | CF₃ | N—SO₂CHF₂ | Cl |
| CH₂Cl | Me | H | H | 2 | H | H | CF₃ | N—SO₂CF₃ | Cl |
| CH₂Cl | Me | H | H | 2 | H | H | CF₃ | N—SO₂Ph | Cl |
| CH₂Cl | Me | H | H | 2 | H | H | CF₃ | N—C(=O)Me | Cl |
| CH₂Cl | Me | H | H | 2 | H | H | CF₃ | N—C(=O)Ph | Cl |
| CH₂Cl | Me | H | H | 2 | H | H | CF₃ | N—C(=O)CH₂Ph | Cl |
| CH₂Cl | Me | H | H | 2 | H | H | Me | N-Ph | Me |
| CH₂Cl | Me | H | H | 2 | H | H | Et | N-Ph | Cl |
| CH₂Cl | Me | H | H | 2 | H | H | Pr | N-Ph | Cl |
| CH₂Cl | Me | H | H | 2 | H | H | Pr-i | N-Ph | Cl |
| CH₂Cl | Me | H | H | 2 | H | H | Bu-t | N-Ph | Cl |
| CH₂Cl | Me | H | H | 2 | H | H | CH₂OMe | N-Ph | Cl |
| CH₂Cl | Me | H | H | 2 | H | H | CF₃ | N-Ph | Me |
| CH₂Cl | Me | H | H | 2 | H | H | CHF₂ | N-Ph | Cl |
| CH₂Cl | Me | H | H | 2 | H | H | CF₃ | N-Ph | Cl |
| CH₂Cl | Me | H | H | 2 | H | H | CF₃ | N-Ph | OMe |
| CH₂Cl | Me | H | H | 2 | H | H | CF₃ | N-Ph | OEt |
| CH₂Cl | Me | H | H | 2 | H | H | CF₃ | N-Ph | OPr-i |
| CH₂Cl | Me | H | H | 2 | H | H | CF₃ | N-Ph | OCH₂CH=CH₂ |
| CH₂Cl | Me | H | H | 2 | H | H | CF₃ | N-Ph | OCH₂C≡CH |
| CH₂Cl | Me | H | H | 2 | H | H | CF₃ | N-Ph | OCH₂CF₃ |

TABLE 4

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | CF₃ | N-Ph | OCH₂C(=O)OMe |
| CH₂Cl | Me | H | H | 2 | H | H | CF₃ | N-Ph | OCH(Me)C(=O)OMe |
| CH₂Cl | Me | H | H | 2 | H | H | CF₃ | N-Ph | OC(Me)₂C(=O)OMe |
| CH₂Cl | Me | H | H | 2 | H | H | CF₃ | N-Ph | OH |
| CH₂Cl | Me | H | H | 2 | H | H | CF₃ | N-Ph | OC(=O)Me |
| CH₂Cl | Me | H | H | 2 | H | H | CF₃ | N-Ph | OC(=O)Ph |
| CH₂Cl | Me | H | H | 2 | H | H | CF₃ | N-Ph | OSO₂Me |
| CH₂Cl | Me | H | H | 2 | H | H | CF₃ | N-Ph | OSO₂CF₃ |
| CH₂Cl | Me | H | H | 2 | H | H | CF₃ | N-Ph | OSO₂Ph |
| CH₂Cl | Me | H | H | 2 | H | H | CF₃ | N-Ph | SMe |
| CH₂Cl | Me | H | H | 2 | H | H | CF₃ | N-Ph | SOMe |
| CH₂Cl | Me | H | H | 2 | H | H | CF₃ | N-Ph | SO₂Me |
| CH₂Cl | Me | H | H | 2 | H | H | CF₃ | N-Ph | SPh |
| CH₂Cl | Me | H | H | 2 | H | H | CF₃ | N-Ph | SOPh |
| CH₂Cl | Me | H | H | 2 | H | H | CF₃ | N-Ph | SO₂Ph |
| CH₂Cl | Me | H | H | 2 | H | H | CF₃ | N-Ph | Imidazol-1-yl |
| CH₂Cl | Me | H | H | 2 | H | H | CF₃ | N-Ph | 1,2,4-Triazol-1-yl |
| CH₂Cl | Me | H | H | 2 | H | H | CF₃ | N-Ph | 1,2,4-Triazol-4-yl |
| CH₂Cl | Me | H | H | 2 | H | H | CF₃ | N-Ph | Tetrazol-1-yl |
| CH₂Cl | Me | H | H | 2 | H | H | CF₂CF₃ | N-Ph | Cl |
| CH₂Cl | Me | H | H | 2 | H | H | CF₃ | N-Ph(2-Cl) | Cl |
| CH₂Cl | Me | H | H | 2 | H | H | CF₃ | N-Ph(2-F) | Cl |
| CH₂Cl | Me | H | H | 2 | H | H | CF₃ | N-Ph(2-OMe) | Cl |
| CH₂Cl | Me | H | H | 2 | H | H | CF₃ | N-Ph(2-Me) | Cl |
| CH₂Cl | Me | H | H | 2 | H | H | CF₃ | N-Ph(2-NO₂) | Cl |
| CH₂Cl | Me | H | H | 2 | H | H | CF₃ | N-Ph(3-Cl) | Cl |
| CH₂Cl | Me | H | H | 2 | H | H | CF₃ | N-Ph(3-F) | Cl |
| CH₂Cl | Me | H | H | 2 | H | H | CF₃ | N-Ph(3-OMe) | Cl |
| CH₂Cl | Me | H | H | 2 | H | H | CF₃ | N-Ph(3-Me) | Cl |
| CH₂Cl | Me | H | H | 2 | H | H | CF₃ | N-Ph(3-NO₂) | Cl |
| CH₂Cl | Me | H | H | 2 | H | H | CF₃ | N-Ph(4-Cl) | Cl |
| CH₂Cl | Me | H | H | 2 | H | H | CF₃ | N-Ph(4-F) | Cl |
| CH₂Cl | Me | H | H | 2 | H | H | CF₃ | N-Ph(4-OMe) | Cl |
| CH₂Cl | Me | H | H | 2 | H | H | CF₃ | N-Ph(4-Me) | Cl |
| CH₂Cl | Me | H | H | 2 | H | H | CF₃ | N-Ph(4-NO₂) | Cl |

TABLE 5

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | Ph | N-Me | Me |
| CH₂Cl | Me | H | H | 2 | H | H | Ph | N-Me | Cl |
| CH₂Cl | Me | H | H | 2 | H | H | Ph | N-Me | OEt |
| CH₂Cl | Me | H | H | 2 | H | H | Ph | N-Me | CF₃ |
| CH₂Cl | Me | H | H | 2 | H | H | Ph | N-Me | Ph |
| CH₂Cl | Me | H | H | 2 | H | H | Me | S | Cl |
| CH₂Cl | Me | H | H | 2 | H | H | Me | S | OEt |
| CH₂Cl | Me | H | H | 2 | H | H | CF₃ | S | Cl |
| CH₂Cl | Me | H | H | 2 | H | H | CF₃ | S | OMe |
| CH₂Cl | Me | H | H | 2 | H | H | CF₃ | S | OEt |
| CH₂Br | H | H | H | 2 | H | H | CF₃ | N-Me | Cl |
| CH₂Cl | H | H | H | 2 | H | H | CF₃ | N-Me | Cl |
| CH₂Cl | H | Me | H | 2 | H | H | CF₃ | N-Me | Cl |
| CH₂Cl | Me | H | H | 2 | Me | H | CF₃ | N-Me | Cl |
| CH₂Cl | Me | H | H | 2 | Et | H | CF₃ | N-Me | Cl |
| CH₂Cl | Me | H | H | 2 | Pr-i | H | CF₃ | N-Me | Cl |
| CH₂Cl | Me | H | H | 2 | Me | Me | CF₃ | N-Me | Cl |
| CH₂Cl | Et | H | H | 2 | H | H | CF₃ | N-Me | Cl |
| CH₂Cl | CH₂Cl | H | H | 2 | H | H | CF₃ | N-Me | Cl |
| CH₂Cl | Pr-i | H | H | 2 | H | H | CF₃ | N-Me | Cl |
| CH₂Cl | Pr | H | H | 2 | H | H | CF₃ | N-Me | Cl |
| CH₂Cl | Pr-c | H | H | 2 | H | H | CF₃ | N-Me | Cl |
| CH₂Cl | CH₂Pr-c | H | H | 2 | H | H | CF₃ | N-Me | Cl |
| CH₂F | Me | H | H | 2 | H | H | CF₃ | N-Me | Cl |
| CH₂Br | Me | H | H | 2 | H | H | CF₃ | N-Me | Cl |
| CH₂I | Me | H | H | 2 | H | H | CF₃ | N-Me | Cl |
| CF₃ | Me | H | H | 2 | H | H | CF₃ | N-Me | Cl |
| CH₂Cl | —(CH₂)₃— | | H | 2 | H | H | CF₃ | N-Me | Cl |
| CH₂Cl | —(CH₂)₄— | | H | 2 | H | H | CF₃ | N-Me | Cl |
| CH₂Cl | —(CH₂)₅— | | H | 2 | H | H | CF₃ | N-Me | Cl |
| CH₂Cl | —(CH₂)₆— | | H | 2 | H | H | CF₃ | N-Me | Cl |
| CH₂Cl | Me | H | H | 1 | H | H | H | N-Me | Cl |
| CH₂Cl | Me | H | H | 1 | H | H | Me | N-Me | Me |
| CH₂Cl | Me | H | H | 1 | H | H | Me | N-Me | Cl |
| CH₂Cl | Me | H | H | 1 | H | H | Cl | N-Me | Cl |

TABLE 6

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | Cl | N-Me | CF₃ |
| CH₂Cl | Me | H | H | 1 | H | H | CHF₂ | N-Me | Cl |
| CH₂Cl | Me | H | H | 1 | H | H | CF₃ | N-Me | Cl |
| CH₂Cl | Me | H | H | 1 | H | H | CF₃ | N-Me | CN |
| CH₂Cl | Me | H | H | 1 | H | H | CF₃ | N-Me | OMe |
| CH₂Cl | Me | H | H | 1 | H | H | CF₃ | N-Me | OEt |
| CH₂Cl | Me | H | H | 1 | H | H | CF₃ | N-Me | OPr-i |
| CH₂Cl | Me | H | H | 1 | H | H | CF₃ | N-Me | OPr |

TABLE 6-continued

| $R^1$ | $R^2$ | $R^3$ | $R^4$ | n | $R^5$ | $R^6$ | $R^{15}$ | $Z^2$ | $R^{16}$ |
|---|---|---|---|---|---|---|---|---|---|
| $CH_2Cl$ | Me | H | H | 1 | H | H | $CF_3$ | N-Me | $OCH_2CH=CH_2$ |
| $CH_2Cl$ | Me | H | H | 1 | H | H | $CF_3$ | N-Me | $OCH_2CF_3$ |
| $CH_2Cl$ | Me | H | H | 1 | H | H | $CF_3$ | N-Me | OPh |
| $CH_2Cl$ | Me | H | H | 1 | H | H | $CF_3$ | N-Me | SMe |
| $CH_2Cl$ | Me | H | H | 1 | H | H | $CF_3$ | N-Me | SOMe |
| $CH_2Cl$ | Me | H | H | 1 | H | H | $CF_3$ | N-Me | $SO_2Me$ |
| $CH_2Cl$ | Me | H | H | 1 | H | H | $CF_3$ | N-Me | $SCF_3$ |
| $CH_2Cl$ | Me | H | H | 1 | H | H | $CF_3$ | N-Me | $SOCF_3$ |
| $CH_2Cl$ | Me | H | H | 1 | H | H | $CF_3$ | N-Me | $SO_2CF_3$ |
| $CH_2Cl$ | Me | H | H | 1 | H | H | $CF_3$ | N-Me | SPh |
| $CH_2Cl$ | Me | H | H | 1 | H | H | $CF_3$ | N-Me | SOPh |
| $CH_2Cl$ | Me | H | H | 1 | H | H | $CF_3$ | N-Me | $SO_2Ph$ |
| $CH_2Cl$ | Me | H | H | 1 | H | H | $CF_3$ | N-Me | Ph |
| $CH_2Cl$ | Me | H | H | 1 | H | H | $CF_2CF_3$ | N-Me | Cl |
| $CH_2Cl$ | Me | H | H | 1 | H | H | $CF_3$ | N-Me | Cl |
| $CH_2Cl$ | Me | H | H | 1 | H | H | $CF_3$ | $N-CH_2OH$ | Cl |
| $CH_2Cl$ | Me | H | H | 1 | H | H | $CF_3$ | $N-CH_2OMe$ | Cl |
| $CH_2Cl$ | Me | H | H | 1 | H | H | $CF_3$ | $N-CH_2CN$ | Cl |
| $CH_2Cl$ | Me | H | H | 1 | H | H | $CF_3$ | $N-CH_2CH=CH_2$ | Cl |
| $CH_2Cl$ | Me | H | H | 1 | H | H | $CF_3$ | $N-CH_2C\equiv CH$ | Cl |
| $CH_2Cl$ | Me | H | H | 1 | H | H | $CF_3$ | N-Et | Cl |
| $CH_2Cl$ | Me | H | H | 1 | H | H | $CF_3$ | N-Pr-i | Cl |
| $CH_2Cl$ | Me | H | H | 1 | H | H | $CF_3$ | N-Pr | Cl |
| $CH_2Cl$ | Me | H | H | 1 | H | H | $CF_3$ | N-Bu-t | Cl |
| $CH_2Cl$ | Me | H | H | 1 | H | H | $CF_3$ | $N—CH_2Ph$ | Cl |
| $CH_2Cl$ | Me | H | H | 1 | H | H | $CF_3$ | $N—CH_2CF_3$ | Cl |
| $CH_2Cl$ | Me | H | H | 1 | H | H | $CF_3$ | $N—CH_2C(=O)OMe$ | Cl |

TABLE 7

| $R^1$ | $R^2$ | $R^3$ | $R^4$ | n | $R^5$ | $R^6$ | $R^{15}$ | $Z^2$ | $R^{16}$ |
|---|---|---|---|---|---|---|---|---|---|
| $CH_2Cl$ | Me | H | H | 1 | H | H | $CF_3$ | $N—CH(Me)C(=O)OMe$ | Cl |
| $CH_2Cl$ | Me | H | H | 1 | H | H | $CF_3$ | $N—C(Me)_2C(=O)OMe$ | Cl |
| $CH_2Cl$ | Me | H | H | 1 | H | H | $CF_3$ | $N—CH_2CH_2SMe$ | Cl |
| $CH_2Cl$ | Me | H | H | 1 | H | H | $CF_3$ | $N—CH_3CH_2SO_2Me$ | Cl |
| $CH_2Cl$ | Me | H | H | 1 | H | H | $CF_3$ | $N—SO_2Me$ | Cl |
| $CH_2Cl$ | Me | H | H | 1 | H | H | $CF_3$ | $N—SO_2CHF_2$ | Cl |
| $CH_2Cl$ | Me | H | H | 1 | H | H | $CF_3$ | $N—SO_2CF_3$ | Cl |
| $CH_2Cl$ | Me | H | H | 1 | H | H | $CF_3$ | $N—SO_2Ph$ | Cl |
| $CH_2Cl$ | Me | H | H | 1 | H | H | $CF_3$ | $N—C(=O)Me$ | Cl |
| $CH_2Cl$ | Me | H | H | 1 | H | H | $CF_3$ | $N—C(=O)Ph$ | Cl |
| $CH_2Cl$ | Me | H | H | 1 | H | H | $CF_3$ | $N—C(=O)CH_2Ph$ | Cl |
| $CH_2Cl$ | Me | H | H | 1 | H | H | Me | N-Ph | Me |
| $CH_2Cl$ | Me | H | H | 1 | H | H | Me | N-Ph | Cl |
| $CH_2Cl$ | Me | H | H | 1 | H | H | Et | N-Ph | Cl |
| $CH_2Cl$ | Me | H | H | 1 | H | H | Pr | N-Ph | Cl |
| $CH_2Cl$ | Me | H | H | 1 | H | H | Pr-i | N-Ph | Cl |
| $CH_2Cl$ | Me | H | H | 1 | H | H | Bu-t | N-Ph | Cl |
| $CH_2Cl$ | Me | H | H | 1 | H | H | $CH_2OMe$ | N-Ph | Cl |
| $CH_2Cl$ | Me | H | H | 1 | H | H | $CF_3$ | N-Ph | Me |
| $CH_2Cl$ | Me | H | H | 1 | H | H | $CHF_2$ | N-Ph | Cl |
| $CH_2Cl$ | Me | H | H | 1 | H | H | $CF_3$ | N-Ph | Cl |
| $CH_2Cl$ | Me | H | H | 1 | H | H | $CF_3$ | N-Ph | OMe |
| $CH_2Cl$ | Me | H | H | 1 | H | H | $CF_3$ | N-Ph | OEt |
| $CH_2Cl$ | Me | H | H | 1 | H | H | $CF_3$ | N-Ph | OPr-i |
| $CH_2Cl$ | Me | H | H | 1 | H | H | $CF_3$ | N-Ph | $OCH_2CH=CH_2$ |
| $CH_2Cl$ | Me | H | H | 1 | H | H | $CF_3$ | N-Ph | $OCH_2C\equiv CH$ |
| $CH_2Cl$ | Me | H | H | 1 | H | H | $CF_3$ | N-Ph | $OCH_2CF_3$ |
| $CH_2Cl$ | Me | H | H | 1 | H | H | $CF_3$ | N-Ph | $OCH_2C(=O)OMe$ |
| $CH_2Cl$ | Me | H | H | 1 | H | H | $CF_3$ | N-Ph | $OCH(Me)C(=O)OMe$ |
| $CH_2Cl$ | Me | H | H | 1 | H | H | $CF_3$ | N-Ph | $OC(Me)_2C(=O)OMe$ |
| $CH_2Cl$ | Me | H | H | 1 | H | H | $CF_3$ | N-Ph | OH |
| $CH_2Cl$ | Me | H | H | 1 | H | H | $CF_3$ | N-Ph | $OC(=O)Me$ |
| $CH_2Cl$ | Me | H | H | 1 | H | H | $CF_3$ | N-Ph | $OC(=O)Ph$ |
| $CH_2Cl$ | Me | H | H | 1 | H | H | $CF_3$ | N-Ph | $OSO_2Me$ |
| $CH_2Cl$ | Me | H | H | 1 | H | H | $CF_3$ | N-Ph | $OSO_2CF_3$ |

TABLE 8

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | CF₃ | N-Ph | OSO₂Ph |
| CH₂Cl | Me | H | H | 1 | H | H | CF₃ | N-Ph | SMe |
| CH₂Cl | Me | H | H | 1 | H | H | CF₃ | N-Ph | SOMe |
| CH₂Cl | Me | H | H | 1 | H | H | CF₃ | N-Ph | SO₂Me |
| CH₂Cl | Me | H | H | 1 | H | H | CF₃ | N-Ph | SPh |
| CH₂Cl | Me | H | H | 1 | H | H | CF₃ | N-Ph | SOPh |
| CH₂Cl | Me | H | H | 1 | H | H | CF₃ | N-Ph | SO₂Ph |
| CH₂Cl | Me | H | H | 1 | H | H | CF₃ | N-Ph | Imidazol-1-yl |
| CH₂Cl | Me | H | H | 1 | H | H | CF₃ | N-Ph | 1,2,4-Triazol-1-yl |
| CH₂Cl | Me | H | H | 1 | H | H | CF₃ | N-Ph | 1,2,4-Triazol-4-yl |
| CH₂Cl | Me | H | H | 1 | H | H | CF₃ | N-Ph | Tetrazol-1-yl |
| CH₂Cl | Me | H | H | 1 | H | H | CF₂CF₃ | N-Ph | Cl |
| CH₂Cl | Me | H | H | 1 | H | H | CF₃ | N-Ph(2-Cl) | Cl |
| CH₂Cl | Me | H | H | 1 | H | H | CF₃ | N-Ph(2-F) | Cl |
| CH₂Cl | Me | H | H | 1 | H | H | CF₃ | N-Ph(2-OMe) | Cl |
| CH₂Cl | Me | H | H | 1 | H | H | CF₃ | N-Ph(2-Me) | Cl |
| CH₂Cl | Me | H | H | 1 | H | H | CF₃ | N-Ph(2-NO₂) | Cl |
| CH₂Cl | Me | H | H | 1 | H | H | CF₃ | N-Ph(3-Cl) | Cl |
| CH₂Cl | Me | H | H | 1 | H | H | CF₃ | N-Ph(3-F) | Cl |
| CH₂Cl | Me | H | H | 1 | H | H | CF₃ | N-Ph(3-OMe) | Cl |
| CH₂Cl | Me | H | H | 1 | H | H | CF₃ | N-Ph(3-Me) | Cl |
| CH₂Cl | Me | H | H | 1 | H | H | CF₃ | N-Ph(3-NO₂) | Cl |
| CH₂Cl | Me | H | H | 1 | H | H | CF₃ | N-Ph(4-Cl) | Cl |
| CH₂Cl | Me | H | H | 1 | H | H | CF₃ | N-Ph(4-F) | Cl |
| CH₂Cl | Me | H | H | 1 | H | H | CF₃ | N-Ph(4-OMe) | Cl |
| CH₂Cl | Me | H | H | 1 | H | H | CF₃ | N-Ph(4-Me) | Cl |
| CH₂Cl | Me | H | H | 1 | H | H | CF₃ | N-Ph(4-NO₂) | Cl |
| CH₂Cl | Me | H | H | 1 | H | H | Ph | N-Me | Me |
| CH₂Cl | Me | H | H | 1 | H | H | Ph | N-Me | Cl |
| CH₂Cl | Me | H | H | 1 | H | H | Ph | N-Me | OEt |
| CH₂Cl | Me | H | H | 1 | H | H | Ph | N-Me | CF₃ |
| CH₂Cl | Me | H | H | 1 | H | H | Ph | N-Me | Ph |
| CH₂Cl | Me | H | H | 1 | H | H | Me | S | Cl |
| CH₂Cl | Me | H | H | 1 | H | H | Me | S | OEt |
| CH₂Cl | Me | H | H | 1 | H | H | CF₃ | S | Cl |

TABLE 9

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | CF₃ | S | OMe |
| CH₂Cl | Me | H | H | 1 | H | H | CF₃ | S | OEt |
| CH₂Cl | H | H | H | 1 | H | H | CF₃ | N-Me | Cl |
| CH₂Cl | H | H | H | 1 | H | H | CF₃ | N-Me | Cl |
| CH₂Cl | H | Me | H | 1 | H | H | CF₃ | N-Me | Cl |
| CH₂Cl | Me | H | H | 1 | Me | H | CF₃ | N-Me | Cl |
| CH₂Cl | Me | H | H | 1 | Et | H | CF₃ | N-Me | Cl |
| CH₂Cl | Me | H | H | 1 | Pr-i | H | CF₃ | N-Me | Cl |
| CH₂Cl | Me | H | H | 1 | Me | Me | CF₃ | N-Me | Cl |
| CH₂Cl | Et | H | H | 1 | H | H | CF₃ | N-Me | Cl |
| CH₂Cl | CH₂Cl | H | H | 1 | H | H | CF₃ | N-Me | Cl |
| CH₂Cl | Pr-i | H | H | 1 | H | H | CF₃ | N-Me | Cl |
| CH₂Cl | Pr | H | H | 1 | H | H | CF₃ | N-Me | Cl |
| CH₂Cl | Pr-c | H | H | 1 | H | H | CF₃ | N-Me | Cl |
| CH₂Cl | CH₂Pr-c | H | H | 1 | H | H | CF₃ | N-Me | Cl |
| CH₂F | Me | H | H | 1 | H | H | CF₃ | N-Me | Cl |
| CH₂Br | Me | H | H | 1 | H | H | CF₃ | N-Me | Cl |
| CH₂I | Me | H | H | 1 | H | H | CF₃ | N-Me | Cl |
| CF₃ | Me | H | H | 1 | H | H | CF₃ | N-Me | Cl |
| CH₂Cl | —(CH₂)₃— | H | H | 1 | H | H | CF₃ | N-Me | Cl |
| CH₂Cl | —(CH₂)₄— | H | H | 1 | H | H | CF₃ | N-Me | Cl |
| CH₂Cl | —(CH₂)₅— | H | H | 1 | H | H | CF₃ | N-Me | Cl |
| CH₂Cl | —(CH₂)₆— | H | H | 1 | H | H | CF₃ | N-Me | Cl |
| CH₂Cl | Me | H | H | 0 | H | H | H | N-Me | H |
| CH₂Cl | Me | H | H | 0 | H | H | Me | N-Me | Me |
| CH₂Cl | Me | H | H | 0 | H | H | Me | N-Me | Cl |
| CH₂Cl | Me | H | H | 0 | H | H | Cl | N-Me | Cl |
| CH₂Cl | Me | H | H | 0 | H | H | Cl | N-Me | CF₃ |
| CH₂Cl | Me | H | H | 0 | H | H | CHF₂ | N-Me | Cl |
| CH₂Cl | Me | H | H | 0 | H | H | CF₃ | N-Me | Cl |
| CH₂Cl | Me | H | H | 0 | H | H | CF₃ | N-Me | CN |
| CH₂Cl | Me | H | H | 0 | H | H | CF₃ | N-Me | OMe |
| CH₂Cl | Me | H | H | 0 | H | H | CF₃ | N-Me | OEt |
| CH₂Cl | Me | H | H | 0 | H | H | CF₃ | N-Me | OPr-i |
| CH₂Cl | Me | H | H | 0 | H | H | CF₃ | N-Me | OPr |

TABLE 10

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | CF₃ | N-Me | OCH₂CH=CH₂ |
| CH₂Cl | Me | H | H | 0 | H | H | CF₃ | N-Me | OCH₂CF₃ |
| CH₂Cl | Me | H | H | 0 | H | H | CF₃ | N-Me | OPh |
| CH₂Cl | Me | H | H | 0 | H | H | CF₃ | N-Me | SMe |
| CH₂Cl | Me | H | H | 0 | H | H | CF₃ | N-Me | SOMe |
| CH₂Cl | Me | H | H | 0 | H | H | CF₃ | N-Me | SO₂Me |
| CH₂Cl | Me | H | H | 0 | H | H | CF₃ | N-Me | SCF₃ |
| CH₂Cl | Me | H | H | 0 | H | H | CF₃ | N-Me | SOCF₃ |

TABLE 10-continued

| R$^1$ | R$^2$ | R$^3$ | R$^4$ | n | R$^5$ | R$^6$ | R$^{15}$ | Z$^2$ | R$^{16}$ |
|---|---|---|---|---|---|---|---|---|---|
| CH$_2$Cl | Me | H | H | 0 | H | H | CF$_3$ | N-Me | SO$_2$CF$_3$ |
| CH$_2$Cl | Me | H | H | 0 | H | H | CF$_3$ | N-Me | SPh |
| CH$_2$Cl | Me | H | H | 0 | H | H | CF$_3$ | N-Me | SOPh |
| CH$_2$Cl | Me | H | H | 0 | H | H | CF$_3$ | N-Me | SO$_2$Ph |
| CH$_2$Cl | Me | H | H | 0 | H | H | CF$_3$ | N-Me | Ph |
| CH$_2$Cl | Me | H | H | 0 | H | H | CF$_2$CF$_3$ | N-Me | Cl |
| CH$_2$Cl | Me | H | H | 0 | H | H | CF$_3$ | N-Me | Cl |
| CH$_2$Cl | Me | H | H | 0 | H | H | CF$_3$ | N—CH$_2$OH | Cl |
| CH$_2$Cl | Me | H | H | 0 | H | H | CF$_3$ | N—CH$_2$OMe | Cl |
| CH$_2$Cl | Me | H | H | 0 | H | H | CF$_3$ | N—CH$_2$CN | Cl |
| CH$_2$Cl | Me | H | H | 0 | H | H | CF$_3$ | N—CH$_2$CH=CH$_2$ | Cl |
| CH$_2$Cl | Me | H | H | 0 | H | H | CF$_3$ | N—CH$_2$C≡CH | Cl |
| CH$_2$Cl | Me | H | H | 0 | H | H | CF$_3$ | N-Et | Cl |
| CH$_2$Cl | Me | H | H | 0 | H | H | CF$_3$ | N-Pr-i | Cl |
| CH$_2$Cl | Me | H | H | 0 | H | H | CF$_3$ | N-Pr | Cl |
| CH$_2$Cl | Me | H | H | 0 | H | H | CF$_3$ | N-Bu-t | Cl |
| CH$_2$Cl | Me | H | H | 0 | H | H | CF$_3$ | N—CH$_2$Ph | Cl |
| CH$_2$Cl | Me | H | H | 0 | H | H | CF$_3$ | N—CH$_2$CF$_3$ | Cl |
| CH$_2$Cl | Me | H | H | 0 | H | H | CF$_3$ | N—CH$_2$C(=O)OMe | Cl |
| CH$_2$Cl | Me | H | H | 0 | H | H | CF$_3$ | N—CH(Me)C(=O)OMe | Cl |
| CH$_2$Cl | Me | H | H | 0 | H | H | CF$_3$ | N—C(Me)$_2$C(=O)OMe | Cl |
| CH$_2$Cl | Me | H | H | 0 | H | H | CF$_3$ | N—CH$_2$CH$_2$SMe | Cl |
| CH$_2$Cl | Me | H | H | 0 | H | H | CF$_3$ | N—CH$_2$CH$_2$SO$_2$Me | Cl |
| CH$_2$Cl | Me | H | H | 0 | H | H | CF$_3$ | N—SO$_2$Me | Cl |
| CH$_2$Cl | Me | H | H | 0 | H | H | CF$_3$ | N—SO$_2$CHF$_2$ | Cl |
| CH$_2$Cl | Me | H | H | 0 | H | H | CF$_3$ | N—SO$_2$CF$_3$ | Cl |
| CH$_2$Cl | Me | H | H | 0 | H | H | CF$_3$ | N—SO$_2$Ph | Cl |

TABLE 11

| R$^1$ | R$^2$ | R$^3$ | R$^4$ | n | R$^5$ | R$^6$ | R$^{15}$ | Z$^2$ | R$^{16}$ |
|---|---|---|---|---|---|---|---|---|---|
| CH$_2$Cl | Me | H | H | 0 | H | H | CF$_3$ | N—C(=O)Me | Cl |
| CH$_2$Cl | Me | H | H | 0 | H | H | CF$_3$ | N—C(=O)Ph | Cl |
| CH$_2$Cl | Me | H | H | 0 | H | H | CF$_3$ | N—C(=O)CH$_2$Ph | Cl |
| CH$_2$Cl | Me | H | H | 0 | H | H | Me | N-Ph | Me |
| CH$_2$Cl | Me | H | H | 0 | H | H | Me | N-Ph | Cl |
| CH$_2$Cl | Me | H | H | 0 | H | H | Et | N-Ph | Cl |
| CH$_2$Cl | Me | H | H | 0 | H | H | Pr | N-Ph | Cl |
| CH$_2$Cl | Me | H | H | 0 | H | H | Pr-i | N-Ph | Cl |
| CH$_2$Cl | Me | H | H | 0 | H | H | Bu-t | N-Ph | Cl |
| CH$_2$Cl | Me | H | H | 0 | H | H | CH$_2$OMe | N-Ph | Cl |
| CH$_2$Cl | Me | H | H | 0 | H | H | CF$_3$ | N-Ph | Me |
| CH$_2$Cl | Me | H | H | 0 | H | H | CHF$_2$ | N-Ph | Cl |
| CH$_2$Cl | Me | H | H | 0 | H | H | CF$_3$ | N-Ph | Cl |
| CH$_2$Cl | Me | H | H | 0 | H | H | CF$_3$ | N-Ph | OMe |
| CH$_2$Cl | Me | H | H | 0 | H | H | CF$_3$ | N-Ph | OEt |
| CH$_2$Cl | Me | H | H | 0 | H | H | CF$_3$ | N-Ph | OPr-i |
| CH$_2$Cl | Me | H | H | 0 | H | H | CF$_3$ | N-Ph | OCH$_2$CH=CH$_2$ |
| CH$_2$Cl | Me | H | H | 0 | H | H | CF$_3$ | N-Ph | OCH$_2$C≡CH |
| CH$_2$Cl | Me | H | H | 0 | H | H | CF$_3$ | N-Ph | OCH$_2$CF$_3$ |
| CH$_2$Cl | Me | H | H | 0 | H | H | CF$_3$ | N-Ph | OCH$_2$C(=O)OMe |
| CH$_2$Cl | Me | H | H | 0 | H | H | CF$_3$ | N-Ph | OCH(Me)C(=O)OMe |
| CH$_2$Cl | Me | H | H | 0 | H | H | CF$_3$ | N-Ph | OC(Me)$_2$C(=O)OMe |
| CH$_2$Cl | Me | H | H | 0 | H | H | CF$_3$ | N-Ph | OH |
| CH$_2$Cl | Me | H | H | 0 | H | H | CF$_3$ | N-Ph | OC(=O)Me |
| CH$_2$Cl | Me | H | H | 0 | H | H | CF$_3$ | N-Ph | OC(=O)Ph |
| CH$_2$Cl | Me | H | H | 0 | H | H | CF$_3$ | N-Ph | OSO$_2$Me |
| CH$_2$Cl | Me | H | H | 0 | H | H | CF$_3$ | N-Ph | OSO$_2$CF$_3$ |
| CH$_2$Cl | Me | H | H | 0 | H | H | CF$_3$ | N-Ph | OSO$_2$Ph |
| CH$_2$Cl | Me | H | H | 0 | H | H | CF$_3$ | N-Ph | SMe |
| CH$_2$Cl | Me | H | H | 0 | H | H | CF$_3$ | N-Ph | SOMe |
| CH$_2$Cl | Me | H | H | 0 | H | H | CF$_3$ | N-Ph | SO$_2$Me |
| CH$_2$Cl | Me | H | H | 0 | H | H | CF$_3$ | N-Ph | SPh |
| CH$_2$Cl | Me | H | H | 0 | H | H | CF$_3$ | N-Ph | SOPh |
| CH$_2$Cl | Me | H | H | 0 | H | H | CF$_3$ | N-Ph | SO$_2$Ph |
| CH$_2$Cl | Me | H | H | 0 | H | H | CF$_3$ | N-Ph | Imidazol-1-yl |

TABLE 12

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | CF₃ | N-Ph | 1,2,4-Triazol-1-yl |
| CH₂Cl | Me | H | H | 0 | H | H | CF₃ | N-Ph | 1,2,4-Triazol-4-yl |
| CH₂Cl | Me | H | H | 0 | H | H | CF₃ | N-Ph | Tetrazol-1-yl |
| CH₂Cl | Me | H | H | 0 | H | H | CF₂CF₃ | N-Ph | Cl |
| CH₂Cl | Me | H | H | 0 | H | H | CF₃ | N-Ph(2-Cl) | Cl |
| CH₂Cl | Me | H | H | 0 | H | H | CF₃ | N-Ph(2-F) | Cl |
| CH₂Cl | Me | H | H | 0 | H | H | CF₃ | N-Ph(2-OMe) | Cl |
| CH₂Cl | Me | H | H | 0 | H | H | CF₃ | N-Ph(2-Me) | Cl |
| CH₂Cl | Me | H | H | 0 | H | H | CF₃ | N-Ph(2-NO₂) | Cl |
| CH₂Cl | Me | H | H | 0 | H | H | CF₃ | N-Ph(3-Cl) | Cl |
| CH₂Cl | Me | H | H | 0 | H | H | CF₃ | N-Ph(3-F) | Cl |
| CH₂Cl | Me | H | H | 0 | H | H | CF₃ | N-Ph(3-OMe) | Cl |
| CH₂Cl | Me | H | H | 0 | H | H | CF₃ | N-Ph(3-Me) | Cl |
| CH₂Cl | Me | H | H | 0 | H | H | CF₃ | N-Ph(3-NO₂) | Cl |
| CH₂Cl | Me | H | H | 0 | H | H | CF₃ | N-Ph(4-Cl) | Cl |
| CH₂Cl | Me | H | H | 0 | H | H | CF₃ | N-Ph(4-F) | Cl |
| CH₂Cl | Me | H | H | 0 | H | H | CF₃ | N-Ph(4-OMe) | Cl |
| CH₂Cl | Me | H | H | 0 | H | H | CF₃ | N-Ph(4-Me) | Cl |
| CH₂Cl | Me | H | H | 0 | H | H | CF₃ | N-Ph(4-NO₂) | Cl |
| CH₂Cl | Me | H | H | 0 | H | H | Ph | N-Me | Me |
| CH₂Cl | Me | H | H | 0 | H | H | Ph | N-Me | Cl |
| CH₂Cl | Me | H | H | 0 | H | H | Ph | N-Me | OEt |
| CH₂Cl | Me | H | H | 0 | H | H | Ph | N-Me | CF₃ |
| CH₂Cl | Me | H | H | 0 | H | H | Ph | N-Me | Ph |
| CH₂Cl | Me | H | H | 0 | H | H | Me | S | Cl |
| CH₂Cl | Me | H | H | 0 | H | H | Me | S | OEt |
| CH₂Cl | Me | H | H | 0 | H | H | CF₃ | S | Cl |
| CH₂Cl | Me | H | H | 0 | H | H | CF₃ | S | OMe |
| CH₂Cl | Me | H | H | 0 | H | H | CF₃ | S | OEt |
| CH₂Cl | H | H | H | 0 | H | H | CF₃ | N-Me | Cl |
| CH₂Cl | H | H | H | 0 | H | H | CF₃ | N-Me | Cl |
| CH₂Cl | H | Me | H | 0 | H | H | CF₃ | N-Me | Cl |
| CH₂Cl | Me | H | H | 0 | Me | H | CF₃ | N-Me | Cl |
| CH₂Cl | Me | H | H | 0 | Et | H | CF₃ | N-Me | Cl |
| CH₂Cl | Me | H | H | 0 | Pr-i | H | CF₃ | N-Me | Cl |

TABLE 13

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | Me | Me | CF₃ | N-Me | Cl |
| CH₂Cl | Et | H | H | 0 | H | H | CF₃ | N-Me | Cl |
| CH₂Cl | CH₂Cl | H | H | 0 | H | H | CF₃ | N-Me | Cl |
| CH₂Cl | Pr-i | H | H | 0 | H | H | CF₃ | N-Me | Cl |
| CH₂Cl | Pr | H | H | 0 | H | H | CF₃ | N-Me | Cl |
| CH₂Cl | Pr-c | H | H | 0 | H | H | CF₃ | N-Me | Cl |
| CH₂Cl | CH₂Pr-c | H | H | 0 | H | H | CF₃ | N-Me | Cl |
| CH₂Cl | Me | H | H | 0 | H | H | CF₃ | N-Me | Cl |
| CH₂Cl | Me | H | H | 0 | H | H | CF₃ | N-Me | Cl |
| CH₂Cl | Me | H | H | 0 | H | H | CF₃ | N-Me | Cl |
| CH₂Cl | —(CH₂)₃— | | H | 0 | H | H | CF₃ | N-Me | Cl |
| CH₂Cl | —(CH₂)₄— | | H | 0 | H | H | CF₃ | N-Me | Cl |
| CH₂Cl | —(CH₂)₅— | | H | 0 | H | H | CF₃ | N-Me | Cl |
| CH₂Cl | —(CH₂)₆— | | H | 0 | H | H | CF₃ | N-Me | Cl |
| CH₂Cl | Et | H | H | 2 | H | H | H | N—H | H |
| CH₂Cl | Me | H | H | 2 | H | H | Cl | N-Et | CF₃ |
| CH₂Cl | Me | H | H | 2 | H | H | Cl | N-Pr | CF₃ |
| CH₂Cl | Me | H | H | 2 | H | H | Cl | N-Pr-i | CF₃ |
| CH₂Cl | Me | H | H | 2 | H | H | Cl | N-Bu-n | CF₃ |
| CH₂Cl | Me | H | H | 2 | H | H | CF₃ | N-Bu-n | Cl |
| CH₂Cl | Me | H | H | 2 | H | H | Cl | N-Bu-s | CF₃ |
| CH₂Cl | Me | H | H | 2 | H | H | CF₃ | N-Bu-s | Cl |
| CH₂Cl | Me | H | H | 2 | H | H | Cl | N-Bu-i | CF₃ |
| CH₂Cl | Me | H | H | 2 | H | H | CF₃ | N-Bu-i | Cl |
| CH₂Cl | Me | H | H | 2 | H | H | CF₃ | N-Bu-t | H |
| CH₂Cl | Me | H | H | 2 | H | H | Cl | N—CH₂Ph | CF₃ |
| CH₂Cl | Me | H | H | 2 | H | H | Cl | N—CH₂CH₂OMe | CF₃ |
| CH₂Cl | Me | H | H | 2 | H | H | CF₃ | N—CH₂CH₂OMe | Cl |
| CH₂Cl | Me | H | H | 2 | H | H | Cl | N—CH₂SMe | CF₃ |
| CH₂Cl | Me | H | H | 2 | H | H | CF₃ | N—CH₂SMe | Cl |
| CH₂Cl | Me | H | H | 2 | H | H | Cl | N—CH₂OEt | CF₃ |
| CH₂Cl | Me | H | H | 2 | H | H | CF₃ | N—CH₂OEt | Cl |
| CH₂Cl | Me | H | H | 2 | H | H | Cl | N—CH₂CHF₂ | CF₃ |
| CH₂Cl | Me | H | H | 2 | H | H | CF₃ | N—CH₂CHF₂ | Cl |

TABLE 14

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | Cl | N—CHF₂ | CF₃ |
| CH₂Cl | Me | H | H | 2 | H | H | CF₃ | N—CHF₂ | Cl |
| CH₂Cl | Me | H | H | 2 | H | H | Cl | N—CH₂CF₃ | CF₃ |
| CH₂Cl | Me | H | H | 2 | H | H | Cl | N—CH₂OMe | CF₃ |
| CH₂Cl | Me | H | H | 2 | H | H | Cl | N—CH₂COOEt | CF₃ |
| CH₂Cl | Me | H | H | 2 | H | H | CF₃ | N—CH₂COOEt | Cl |
| CH₂Cl | Me | H | H | 2 | H | H | Cl | N—CH₂CH=CH₂ | CF₃ |
| CH₂Cl | Me | H | H | 2 | H | H | Cl | N—CH₂C≡CH | CF₃ |
| CH₂Cl | Me | H | H | 2 | H | H | Cl | N—CH₂Pr-c | CF₃ |
| CH₂Cl | Me | H | H | 2 | H | H | CF₃ | N—CH₂Pr-c | Cl |
| CH₂Cl | Me | H | H | 2 | H | H | Cl | N—CH₂Bu-c | CF₃ |
| CH₂Cl | Me | H | H | 2 | H | H | CF₃ | N—CH₂Bu-c | Cl |
| CH₂Cl | Me | H | H | 2 | H | H | Cl | N—CH₂Pen-c | CF₃ |
| CH₂Cl | Me | H | H | 2 | H | H | CF₃ | N—CH₂Pen-c | Cl |
| CH₂Cl | Me | H | H | 2 | H | H | Cl | N—CH₂Hex-c | CF₃ |
| CH₂Cl | Me | H | H | 2 | H | H | CF₃ | N—CH₂Hex-c | Cl |
| CH₂Cl | Me | H | H | 2 | H | H | Cl | N—CH₂CCl=CHCl | CF₃ |
| CH₂Cl | Me | H | H | 2 | H | H | CF₃ | N—CH₂CCl=CHCl | Cl |
| CH₂Cl | Me | H | H | 2 | H | H | CF₃ | N-Hex-c | Cl |
| CH₂Cl | Me | H | H | 2 | H | H | CF₃ | N-Pen-c | Cl |
| CH₂Cl | Me | H | H | 2 | H | H | Cl | N—CH₂NMe₂ | CF₃ |
| CH₂Cl | Me | H | H | 2 | H | H | CF₃ | N—CH₂NMe₂ | Cl |
| CH₂Cl | Me | H | H | 2 | H | H | Cl | N—CH₂NHMe | CF₃ |
| CH₂Cl | Me | H | H | 2 | H | H | CF₃ | N—CH₂NHMe | Cl |
| CH₂Cl | Me | H | H | 2 | H | H | Cl | N—CH₂N(Me)COMe | CF₃ |
| CH₂Cl | Me | H | H | 2 | H | H | CF₃ | N—CH₂N(Me)COMe | Cl |
| CH₂Cl | Me | H | H | 2 | H | H | Cl | N—CH₂N(Me)COCF₃ | CF₃ |
| CH₂Cl | Me | H | H | 2 | H | H | CF₃ | N—CH₂N(Me)COCF₃ | Cl |
| CH₂Cl | Me | H | H | 2 | H | H | Cl | N—CH₂N(Me)SO₂Me | CF₃ |
| CH₂Cl | Me | H | H | 2 | H | H | CF₃ | N—CH₂N(Me)SO₂Me | Cl |
| CH₂Cl | Me | H | H | 2 | H | H | Cl | N—CH₂CONH₂ | CF₃ |
| CH₂Cl | Me | H | H | 2 | H | H | CF₃ | N—CH₂CONH₂ | Cl |
| CH₂Cl | Me | H | H | 2 | H | H | Cl | N—CH₂CONHMe | CF₃ |
| CH₂Cl | Me | H | H | 2 | H | H | CF₃ | N—CH₂CONHMe | Cl |
| CH₂Cl | Me | H | H | 2 | H | H | Cl | N—CH₂CONMe₂ | CF₃ |

TABLE 15

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | CF₃ | N—CH₂CONMe₂ | Cl |
| CH₂Cl | Me | H | H | 2 | H | H | Cl | N—CH₂COMe | CF₃ |
| CH₂Cl | Me | H | H | 2 | H | H | CF₃ | N—CH₂COMe | Cl |
| CH₂Cl | Me | H | H | 2 | H | H | Cl | N—CH₂CH₂COMe | CF₃ |
| CH₂Cl | Me | H | H | 2 | H | H | CF₃ | N—CH₂CH₂COMe | Cl |
| CH₂Cl | Me | H | H | 2 | H | H | Cl | N—CH₂COCF₃ | CF₃ |
| CH₂Cl | Me | H | H | 2 | H | H | CF₃ | N—CH₂COCF₃ | Cl |
| CH₂Cl | Me | H | H | 2 | H | H | CF₃ | N-Me | F |
| CH₂Cl | Me | H | H | 2 | H | H | CF₃ | N-Me | Me |
| CH₂Cl | Me | H | H | 2 | H | H | CF₃ | N-Me | CF₃ |
| CH₂Cl | Me | H | H | 2 | H | H | CF₃ | N-Me | OH |
| CH₂Cl | Me | H | H | 2 | H | H | CF₃ | N-Me | OBu-n |
| CH₂Cl | Me | H | H | 2 | H | H | CF₃ | N-Me | OBu-t |
| CH₂Cl | Me | H | H | 2 | H | H | CF₃ | N-Me | OCH₂CHF₂ |
| CH₂Cl | Me | H | H | 2 | H | H | CF₃ | N-Me | OCHF₂ |
| CH₂Cl | Me | H | H | 2 | H | H | CF₃ | N-Me | OPen-c |
| CH₂Cl | Me | H | H | 2 | H | H | CF₃ | N-Me | OHex-c |
| CH₂Cl | Me | H | H | 2 | H | H | CF₃ | N-Me | OCH₂Pr-c |
| CH₂Cl | Me | H | H | 2 | H | H | CF₃ | N-Me | NH₂ |
| CH₂Cl | Me | H | H | 2 | H | H | CF₃ | N-Me | NHMe |
| CH₂Cl | Me | H | H | 2 | H | H | CF₃ | N-Me | NMe₂ |
| CH₂Cl | Me | H | H | 2 | H | H | CF₃ | N-Me | NHPh |
| CH₂Cl | Me | H | H | 2 | H | H | CF₃ | N-Me | NMePh |
| CH₂Cl | Me | H | H | 2 | H | H | CF₃ | N-Me | O-Ph(2-Cl) |
| CH₂Cl | Me | H | H | 2 | H | H | CF₃ | N-Me | O-Ph(3-Cl) |
| CH₂Cl | Me | H | H | 2 | H | H | CF₃ | N-Me | O-Ph(4-Cl) |
| CH₂Cl | Me | H | H | 2 | H | H | CF₃ | N-Me | O-Ph(4-F) |
| CH₂Cl | Me | H | H | 2 | H | H | CF₃ | N-Me | O-Ph(4-Me) |
| CH₂Cl | Me | H | H | 2 | H | H | CF₃ | N-Me | O-Ph(4-OMe) |
| CH₂Cl | Me | H | H | 2 | H | H | CF₃ | N-Me | SO₂Et |
| CH₂Cl | Me | H | H | 2 | H | H | CF₃ | N-Ph | H |
| CH₂Cl | Me | H | H | 2 | H | H | CF₃ | N-Ph | F |
| CH₂Cl | Me | H | H | 2 | H | H | CF₃ | N-Ph | CN |
| CH₂Cl | Me | H | H | 2 | H | H | CF₃ | N-Ph | CF₃ |
| CH₂Cl | Me | H | H | 2 | H | H | CF₃ | N-Ph | Pr-n |

TABLE 16

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | CF₃ | N-Ph | OBu-t |
| CH₂Cl | Me | H | H | 2 | H | H | CF₃ | N-Ph | OCH₂CHF₂ |
| CH₂Cl | Me | H | H | 2 | H | H | CF₃ | N-Ph | OCHF₂ |
| CH₂Cl | Me | H | H | 2 | H | H | CF₃ | N-Ph | NH₂ |
| CH₂Cl | Me | H | H | 2 | H | H | CF₃ | N-Ph | NHMe |
| CH₂Cl | Me | H | H | 2 | H | H | CF₃ | N-Ph | NMe₂ |
| CH₂Cl | Me | H | H | 2 | H | H | CF₃ | N-Ph | SO₂Et |
| CH₂Cl | Me | H | H | 2 | H | H | Cl | N-Bu-t | CF₃ |
| CH₂Cl | Me | H | H | 2 | H | H | CF₃ | N-Ph(4-COMe) | Cl |
| CH₂Cl | Me | H | H | 2 | H | H | CF₃ | N-Ph(4-CN) | Cl |
| CH₂Cl | Me | H | H | 2 | H | H | CF₃ | N-Ph(4-COOMe) | Cl |
| CH₂Cl | Me | H | H | 2 | H | H | CF₃ | N-Ph(4-NO₂) | Cl |
| CH₂Cl | Me | H | H | 2 | H | H | CF₃ | N-Pyrimidin-2-yl | Cl |
| CH₂Cl | Me | H | H | 1 | H | H | Cl | N-Et | CF₃ |
| CH₂Cl | Me | H | H | 1 | H | H | Cl | N-Pr | CF₃ |
| CH₂Cl | Me | H | H | 1 | H | H | Cl | N-Pr-i | CF₃ |
| CH₂Cl | Me | H | H | 1 | H | H | Cl | N-Bu-n | CF₃ |
| CH₂Cl | Me | H | H | 1 | H | H | CF₃ | N-Bu-n | Cl |
| CH₂Cl | Me | H | H | 1 | H | H | Cl | N-Bu-s | CF₃ |
| CH₂Cl | Me | H | H | 1 | H | H | CF₃ | N-Bu-s | Cl |
| CH₂Cl | Me | H | H | 1 | H | H | Cl | N-Bu-i | CF₃ |
| CH₂Cl | Me | H | H | 1 | H | H | CF₃ | N-Bu-i | Cl |
| CH₂Cl | Me | H | H | 1 | H | H | CF₃ | N-Bu-t | H |
| CH₂Cl | Me | H | H | 1 | H | H | Cl | N—CH₂Ph | CF₃ |
| CH₂Cl | Me | H | H | 1 | H | H | Cl | N—CH₂CH₂OMe | CF₃ |
| CH₂Cl | Me | H | H | 1 | H | H | CF₃ | N—CH₂CH₂OMe | Cl |
| CH₂Cl | Me | H | H | 1 | H | H | Cl | N—CH₂SMe | CF₃ |
| CH₂Cl | Me | H | H | 1 | H | H | CF₃ | N—CH₂SMe | Cl |
| CH₂Cl | Me | H | H | 1 | H | H | Cl | N—CH₂OEt | CF₃ |
| CH₂Cl | Me | H | H | 1 | H | H | CF₃ | N—CH₂OEt | Cl |
| CH₂Cl | Me | H | H | 1 | H | H | Cl | N—CH₂CHF₂ | CF₃ |
| CH₂Cl | Me | H | H | 1 | H | H | CF₃ | N—CH₂CHF₂ | Cl |
| CH₂Cl | Me | H | H | 1 | H | H | Cl | N—CHF₂ | CF₃ |
| CH₂Cl | Me | H | H | 1 | H | H | CF₃ | N—CHF₂ | Cl |
| CH₂Cl | Me | H | H | 1 | H | H | Cl | N—CH₂CF₃ | CF₃ |

TABLE 17

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | Cl | N—CH₂OMe | CF₃ |
| CH₂Cl | Me | H | H | 1 | H | H | Cl | N—CH₂COOEt | CF₃ |
| CH₂Cl | Me | H | H | 1 | H | H | CF₃ | N—CH₂COOEt | Cl |
| CH₂Cl | Me | H | H | 1 | H | H | Cl | N—CH₂CH=CH₂ | CF₃ |
| CH₂Cl | Me | H | H | 1 | H | H | Cl | N—CH₂C≡CH | CF₃ |
| CH₂Cl | Me | H | H | 1 | H | H | Cl | N—CH₂Pr-c | CF₃ |
| CH₂Cl | Me | H | H | 1 | H | H | CF₃ | N—CH₂Pr-c | Cl |
| CH₂Cl | Me | H | H | 1 | H | H | Cl | N—CH₂Bu-c | CF₃ |
| CH₂Cl | Me | H | H | 1 | H | H | CF₃ | N—CH₂Bu-c | Cl |
| CH₂Cl | Me | H | H | 1 | H | H | Cl | N—CH₂Pen-c | CF₃ |
| CH₂Cl | Me | H | H | 1 | H | H | CF₃ | N—CH₂Pen-c | Cl |
| CH₂Cl | Me | H | H | 1 | H | H | Cl | N—CH₂Hex-c | CF₃ |
| CH₂Cl | Me | H | H | 1 | H | H | CF₃ | N—CH₂Hex-c | Cl |
| CH₂Cl | Me | H | H | 1 | H | H | Cl | N—CH₂CCl=CHCl | CF₃ |
| CH₂Cl | Me | H | H | 1 | H | H | CF₃ | N—CH₂CCl=CHCl | Cl |
| CH₂Cl | Me | H | H | 1 | H | H | CF₃ | N-Hex-c | Cl |
| CH₂Cl | Me | H | H | 1 | H | H | CF₃ | N-Pen-c | Cl |
| CH₂Cl | Me | H | H | 1 | H | H | Cl | N—CH₂NMe₂ | CF₃ |
| CH₂Cl | Me | H | H | 1 | H | H | CF₃ | N—CH₂NMe₂ | Cl |
| CH₂Cl | Me | H | H | 1 | H | H | Cl | N—CH₂NHMe | CF₃ |
| CH₂Cl | Me | H | H | 1 | H | H | CF₃ | N—CH₂NHMe | Cl |
| CH₂Cl | Me | H | H | 1 | H | H | Cl | N—CH₂N(Me)COMe | CF₃ |
| CH₂Cl | Me | H | H | 1 | H | H | CF₃ | N—CH₂N(Me)COMe | Cl |
| CH₂Cl | Me | H | H | 1 | H | H | Cl | N—CH₂N(Me)COCF₃ | CF₃ |
| CH₂Cl | Me | H | H | 1 | H | H | CF₃ | N—CH₂N(Me)COCF₃ | Cl |
| CH₂Cl | Me | H | H | 1 | H | H | Cl | N—CH₂N(Me)SO₂Me | CF₃ |
| CH₂Cl | Me | H | H | 1 | H | H | CF₃ | N—CH₂N(Me)SO₂Me | Cl |
| CH₂Cl | Me | H | H | 1 | H | H | Cl | N—CH₂CONH₂ | CF₃ |
| CH₂Cl | Me | H | H | 1 | H | H | CF₃ | N—CH₂CONH₂ | Cl |
| CH₂Cl | Me | H | H | 1 | H | H | Cl | N—CH₂CONHMe | CF₃ |
| CH₂Cl | Me | H | H | 1 | H | H | CF₃ | N—CH₂CONHMe | Cl |
| CH₂Cl | Me | H | H | 1 | H | H | Cl | N—CH₂CONMe₂ | CF₃ |
| CH₂Cl | Me | H | H | 1 | H | H | CF₃ | N—CH₂CONMe₂ | Cl |
| CH₂Cl | Me | H | H | 1 | H | H | Cl | N—CH₂COMe | CF₃ |
| CH₂Cl | Me | H | H | 1 | H | H | CF₃ | N—CH₂COMe | Cl |

TABLE 18

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | Cl | N—CH₂CH₂COMe | CF₃ |
| CH₂Cl | Me | H | H | 1 | H | H | CF₃ | N—CH₂CH₂COMe | Cl |
| CH₂Cl | Me | H | H | 1 | H | H | Cl | N—CH₂COCF₃ | CF₃ |
| CH₂Cl | Me | H | H | 1 | H | H | CF₃ | N—CH₂COCF₃ | Cl |
| CH₂Cl | Me | H | H | 1 | H | H | CF₃ | N-Me | F |
| CH₂Cl | Me | H | H | 1 | H | H | CF₃ | N-Me | Me |
| CH₂Cl | Me | H | H | 1 | H | H | CF₃ | N-Me | CF₃ |
| CH₂Cl | Me | H | H | 1 | H | H | CF₃ | N-Me | OH |
| CH₂Cl | Me | H | H | 1 | H | H | CF₃ | N-Me | OBu-n |
| CH₂Cl | Me | H | H | 1 | H | H | CF₃ | N-Me | OBu-t |
| CH₂Cl | Me | H | H | 1 | H | H | CF₃ | N-Me | OCH₂CHF₂ |
| CH₂Cl | Me | H | H | 1 | H | H | CF₃ | N-Me | OCHF₂ |
| CH₂Cl | Me | H | H | 1 | H | H | CF₃ | N-Me | OPen-c |
| CH₂Cl | Me | H | H | 1 | H | H | CF₃ | N-Me | OHex-c |
| CH₂Cl | Me | H | H | 1 | H | H | CF₃ | N-Me | OCH₂Pr-c |
| CH₂Cl | Me | H | H | 1 | H | H | CF₃ | N-Me | NH₂ |
| CH₂Cl | Me | H | H | 1 | H | H | CF₃ | N-Me | NHMe |
| CH₂Cl | Me | H | H | 1 | H | H | CF₃ | N-Me | NMe₂ |
| CH₂Cl | Me | H | H | 1 | H | H | CF₃ | N-Me | NHPh |
| CH₂Cl | Me | H | H | 1 | H | H | CF₃ | N-Me | NMePh |
| CH₂Cl | Me | H | H | 1 | H | H | CF₃ | N-Me | O-Ph(2-Cl) |
| CH₂Cl | Me | H | H | 1 | H | H | CF₃ | N-Me | O-Ph(3-Cl) |
| CH₂Cl | Me | H | H | 1 | H | H | CF₃ | N-Me | O-Ph(4-Cl) |
| CH₂Cl | Me | H | H | 1 | H | H | CF₃ | N-Me | O-Ph(4-F) |
| CH₂Cl | Me | H | H | 1 | H | H | CF₃ | N-Me | O-Ph(4-Me) |
| CH₂Cl | Me | H | H | 1 | H | H | CF₃ | N-Me | O-Ph(4-OMe) |
| CH₂Cl | Me | H | H | 1 | H | H | CF₃ | N-Me | SO₂Et |
| CH₂Cl | Me | H | H | 1 | H | H | CF₃ | N-Ph | H |
| CH₂Cl | Me | H | H | 1 | H | H | CF₃ | N-Ph | F |
| CH₂Cl | Me | H | H | 1 | H | H | CF₃ | N-Ph | CN |
| CH₂Cl | Me | H | H | 1 | H | H | CF₃ | N-Ph | CF₃ |
| CH₂Cl | Me | H | H | 1 | H | H | CF₃ | N-Ph | Pr-n |
| CH₂Cl | Me | H | H | 1 | H | H | CF₃ | N-Ph | OBu-t |
| CH₂Cl | Me | H | H | 1 | H | H | CF₃ | N-Ph | OCH₂CHF₂ |
| CH₂Cl | Me | H | H | 1 | H | H | CF₃ | N-Ph | OCHF₂ |

TABLE 19

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | CF₃ | N-Ph | NH₂ |
| CH₂Cl | Me | H | H | 1 | H | H | CF₃ | N-Ph | NHMe |
| CH₂Cl | Me | H | H | 1 | H | H | CF₃ | N-Ph | NMe₂ |
| CH₂Cl | Me | H | H | 1 | H | H | CF₃ | N-Ph | SO₂Et |
| CH₂Cl | Me | H | H | 1 | H | H | Cl | N-Bu-t | CF₃ |
| CH₂Cl | Me | H | H | 1 | H | H | CF₃ | N-Ph(4-COMe) | Cl |
| CH₂Cl | Me | H | H | 1 | H | H | CF₃ | N-Ph(4-CN) | Cl |
| CH₂Cl | Me | H | H | 1 | H | H | CF₃ | N-Ph(4-COOMe) | Cl |
| CH₂Cl | Me | H | H | 1 | H | H | CF₃ | N-Ph(4-NO₂) | Cl |
| CH₂Cl | Me | H | H | 1 | H | H | CF₃ | N-Pyrimidin-2-yl | Cl |
| CH₂Cl | Me | H | H | 0 | H | H | Cl | N-Et | CF₃ |
| CH₂Cl | Me | H | H | 0 | H | H | Cl | N-Pr | CF₃ |
| CH₂Cl | Me | H | H | 0 | H | H | Cl | N-Pr-i | CF₃ |
| CH₂Cl | Me | H | H | 0 | H | H | Cl | N-Bu-n | CF₃ |
| CH₂Cl | Me | H | H | 0 | H | H | CF₃ | N-Bu-n | Cl |
| CH₂Cl | Me | H | H | 0 | H | H | Cl | N-Bu-s | CF₃ |
| CH₂Cl | Me | H | H | 0 | H | H | CF₃ | N-Bu-s | Cl |
| CH₂Cl | Me | H | H | 0 | H | H | Cl | N-Bu-i | CF₃ |
| CH₂Cl | Me | H | H | 0 | H | H | CF₃ | N-Bu-i | Cl |
| CH₂Cl | Me | H | H | 0 | H | H | CF₃ | N-Bu-t | H |
| CH₂Cl | Me | H | H | 0 | H | H | Cl | N—CH₂Ph | CF₃ |
| CH₂Cl | Me | H | H | 0 | H | H | Cl | N—CH₂CH₂OMe | CF₃ |
| CH₂Cl | Me | H | H | 0 | H | H | CF₃ | N—CH₂CH₂OMe | Cl |
| CH₂Cl | Me | H | H | 0 | H | H | Cl | N—CH₂SMe | CF₃ |
| CH₂Cl | Me | H | H | 0 | H | H | CF₃ | N—CH₂SMe | Cl |
| CH₂Cl | Me | H | H | 0 | H | H | Cl | N—CH₂OEt | CF₃ |
| CH₂Cl | Me | H | H | 0 | H | H | CF₃ | N—CH₂OEt | Cl |
| CH₂Cl | Me | H | H | 0 | H | H | Cl | N—CH₂CHF₂ | CF₃ |
| CH₂Cl | Me | H | H | 0 | H | H | CF₃ | N—CH₂CHF₂ | Cl |
| CH₂Cl | Me | H | H | 0 | H | H | Cl | N—CHF₂ | CF₃ |
| CH₂Cl | Me | H | H | 0 | H | H | CF₃ | N—CHF₂ | Cl |
| CH₂Cl | Me | H | H | 0 | H | H | Cl | N—CH₂CF₃ | CF₃ |
| CH₂Cl | Me | H | H | 0 | H | H | Cl | N—CH₂OMe | CF₃ |
| CH₂Cl | Me | H | H | 0 | H | H | Cl | N—CH₂COOEt | CF₃ |
| CH₂Cl | Me | H | H | 0 | H | H | CF₃ | N—CH₂COOEt | Cl |

TABLE 20

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | Cl | N—CH₂CH=CH₂ | CF₃ |
| CH₂Cl | Me | H | H | 0 | H | H | Cl | N—CH₂C≡CH | CF₃ |
| CH₂Cl | Me | H | H | 0 | H | H | Cl | N—CH₂Pr-c | CF₃ |
| CH₂Cl | Me | H | H | 0 | H | H | CF₃ | N—CH₂Pr-c | Cl |
| CH₂Cl | Me | H | H | 0 | H | H | Cl | N—CH₂Bu-c | CF₃ |
| CH₂Cl | Me | H | H | 0 | H | H | CF₃ | N—CH₂Bu-c | Cl |
| CH₂Cl | Me | H | H | 0 | H | H | Cl | N—CH₂Pen-c | CF₃ |
| CH₂Cl | Me | H | H | 0 | H | H | CF₃ | N—CH₂Pen-c | Cl |

TABLE 20-continued

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | Cl | N—CH₂Hex-c | CF₃ |
| CH₂Cl | Me | H | H | 0 | H | H | CF₃ | N—CH₂Hex-c | Cl |
| CH₂Cl | Me | H | H | 0 | H | H | Cl | N—CH₂CCl=CHCl | CF₃ |
| CH₂Cl | Me | H | H | 0 | H | H | CF₃ | N—CH₂CCl=CHCl | Cl |
| CH₂Cl | Me | H | H | 0 | H | H | CF₃ | N-Hex-c | Cl |
| CH₂Cl | Me | H | H | 0 | H | H | CF₃ | N-Pen-c | Cl |
| CH₂Cl | Me | H | H | 0 | H | H | Cl | N—CH₂NMe₂ | CF₃ |
| CH₂Cl | Me | H | H | 0 | H | H | CF₃ | N—CH₂NMe₂ | Cl |
| CH₂Cl | Me | H | H | 0 | H | H | Cl | N—CH₂NHMe | CF₃ |
| CH₂Cl | Me | H | H | 0 | H | H | CF₃ | N—CH₂NHMe | Cl |
| CH₂Cl | Me | H | H | 0 | H | H | Cl | N—CH₂N(Me)COMe | CF₃ |
| CH₂Cl | Me | H | H | 0 | H | H | CF₃ | N—CH₂N(Me)COMe | Cl |
| CH₂Cl | Me | H | H | 0 | H | H | Cl | N—CH₂N(Me)COCF₃ | CF₃ |
| CH₂Cl | Me | H | H | 0 | H | H | CF₃ | N—CH₂N(Me)COCF₃ | Cl |
| CH₂Cl | Me | H | H | 0 | H | H | Cl | N—CH₂N(Me)SO₂Me | CF₃ |
| CH₂Cl | Me | H | H | 0 | H | H | CF₃ | N—CH₂N(Me)SO₂Me | Cl |
| CH₂Cl | Me | H | H | 0 | H | H | Cl | N—CH₂CONH₂ | CF₃ |
| CH₂Cl | Me | H | H | 0 | H | H | CF₃ | N—CH₂CONH₂ | Cl |
| CH₂Cl | Me | H | H | 0 | H | H | Cl | N—CH₂CONHMe | CF₃ |
| CH₂Cl | Me | H | H | 0 | H | H | CF₃ | N—CH₂CONHMe | Cl |
| CH₂Cl | Me | H | H | 0 | H | H | Cl | N—CH₂CONMe₂ | CF₃ |
| CH₂Cl | Me | H | H | 0 | H | H | CF₃ | N—CH₂CONMe₂ | Cl |
| CH₂Cl | Me | H | H | 0 | H | H | Cl | N—CH₂COMe | CF₃ |
| CH₂Cl | Me | H | H | 0 | H | H | CF₃ | N—CH₂COMe | Cl |
| CH₂Cl | Me | H | H | 0 | H | H | Cl | N—CH₂CH₂COMe | CF₃ |
| CH₂Cl | Me | H | H | 0 | H | H | CF₃ | N—CH₂CH₂COMe | Cl |
| CH₂Cl | Me | H | H | 0 | H | H | Cl | N—CH₂COCF₃ | CF₃ |

TABLE 21

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | CF₃ | N—CH₂COCF₃ | Cl |
| CH₂Cl | Me | H | H | 0 | H | H | CF₃ | N-Me | F |
| CH₂Cl | Me | H | H | 0 | H | H | CF₃ | N-Me | Me |
| CH₂Cl | Me | H | H | 0 | H | H | CF₃ | N-Me | CF₃ |
| CH₂Cl | Me | H | H | 0 | H | H | CF₃ | N-Me | OH |
| CH₂Cl | Me | H | H | 0 | H | H | CF₃ | N-Me | OBu-n |
| CH₂Cl | Me | H | H | 0 | H | H | CF₃ | N-Me | OBu-t |
| CH₂Cl | Me | H | H | 0 | H | H | CF₃ | N-Me | OCH₂CHF₂ |
| CH₂Cl | Me | H | H | 0 | H | H | CF₃ | N-Me | OCHF₂ |
| CH₂Cl | Me | H | H | 0 | H | H | CF₃ | N-Me | OPen-c |
| CH₂Cl | Me | H | H | 0 | H | H | CF₃ | N-Me | OHex-c |
| CH₂Cl | Me | H | H | 0 | H | H | CF₃ | N-Me | OCH₂Pr-c |
| CH₂Cl | Me | H | H | 0 | H | H | CF₃ | N-Me | NH₂ |
| CH₂Cl | Me | H | H | 0 | H | H | CF₃ | N-Me | NHMe |
| CH₂Cl | Me | H | H | 0 | H | H | CF₃ | N-Me | NMe₂ |
| CH₂Cl | Me | H | H | 0 | H | H | CF₃ | N-Me | NHPh |
| CH₂Cl | Me | H | H | 0 | H | H | CF₃ | N-Me | NMePh |
| CH₂Cl | Me | H | H | 0 | H | H | CF₃ | N-Me | O-Ph(2-Cl) |
| CH₂Cl | Me | H | H | 0 | H | H | CF₃ | N-Me | O-Ph(3-Cl) |
| CH₂Cl | Me | H | H | 0 | H | H | CF₃ | N-Me | O-Ph(4-Cl) |
| CH₂Cl | Me | H | H | 0 | H | H | CF₃ | N-Me | O-Ph(4-F) |
| CH₂Cl | Me | H | H | 0 | H | H | CF₃ | N-Me | O-Ph(4-Me) |
| CH₂Cl | Me | H | H | 0 | H | H | CF₃ | N-Me | O-Ph(4-OMe) |
| CH₂Cl | Me | H | H | 0 | H | H | CF₃ | N-Me | SO₂Et |
| CH₂Cl | Me | H | H | 0 | H | H | CF₃ | N-Ph | H |
| CH₂Cl | Me | H | H | 0 | H | H | CF₃ | N-Ph | F |
| CH₂Cl | Me | H | H | 0 | H | H | CF₃ | N-Ph | CN |
| CH₂Cl | Me | H | H | 0 | H | H | CF₃ | N-Ph | CF₃ |
| CH₂Cl | Me | H | H | 0 | H | H | CF₃ | N-Ph | Pr-n |
| CH₂Cl | Me | H | H | 0 | H | H | CF₃ | N-Ph | OBu-4 |
| CH₂Cl | Me | H | H | 0 | H | H | CF₃ | N-Ph | OCH₂CHF₂ |
| CH₂Cl | Me | H | H | 0 | H | H | CF₃ | N-Ph | OCHF₂ |
| CH₂Cl | Me | H | H | 0 | H | H | CF₃ | N-Ph | NH₂ |
| CH₂Cl | Me | H | H | 0 | H | H | CF₃ | N-Ph | NHMe |
| CH₂Cl | Me | H | H | 0 | H | H | CF₃ | N-Ph | NMe₂ |

TABLE 22

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | CF₃ | N-Ph | SO₂Et |
| CH₂Cl | Me | H | H | 0 | H | H | Cl | N-Bu-t | CF₃ |
| CH₂Cl | Me | H | H | 0 | H | H | CF₃ | N-Ph(4-COMe) | Cl |
| CH₂Cl | Me | H | H | 0 | H | H | CF₃ | N-Ph(4-CN) | Cl |
| CH₂Cl | Me | H | H | 0 | H | H | CF₃ | N-Ph(4-COOMe) | Cl |
| CH₂Cl | Me | H | H | 0 | H | H | CF₃ | N-Ph(4-NO₂) | Cl |
| CH₂Cl | Me | H | H | 0 | H | H | CF₃ | N-Pyrimidin-2-yl | Cl |
| CH₂Cl | Me | H | H | 2 | H | H | CF₃ | N—NH₂ | Cl |
| CH₂Cl | Me | H | H | 2 | H | H | Cl | N—NH₂ | CF₃ |
| CH₂Cl | Me | H | H | 2 | H | H | OH | N-Me | CF₃ |
| CH₂Cl | Me | H | H | 2 | H | H | OMe | N-Me | CF₃ |
| CH₂Cl | Me | H | H | 2 | H | H | OEt | N-Me | CF₃ |
| CH₂Cl | Me | H | H | 2 | H | H | OPr-i | N-Me | CF₃ |
| CH₂Cl | Me | H | H | 2 | H | H | OCHF₂ | N-Me | CF₃ |
| CH₂Cl | Me | H | H | 2 | H | H | OCH₂CHF₂ | N-Me | CF₃ |
| CH₂Cl | Me | H | H | 2 | H | H | OCH₂CF₃ | N-Me | CF₃ |
| CH₂Cl | Me | H | H | 2 | H | H | OCHF₂ | N-Me | OCHF₂ |
| CH₂Cl | Me | H | H | 2 | H | H | CF₃ | N-Me | CONH₂ |
| CH₂Cl | Me | H | H | 2 | H | H | CF₃ | N-Me | CONHMe |
| CH₂Cl | Me | H | H | 2 | H | H | CF₃ | N-Me | CONMe₂ |
| CH₂Cl | Me | H | H | 2 | H | H | CF₃ | N-Me | COOMe |
| CH₂Cl | Me | H | H | 2 | H | H | CF₃ | N-Me | COOEt |
| CH₂Cl | Me | H | H | 2 | H | H | CF₃ | N-Me | COOPr-i |
| CH₂Cl | Me | H | H | 2 | H | H | CF₃ | N-Me | COMe |
| CH₂Cl | Me | H | H | 2 | H | H | CF₃ | N-Me | COEt |
| CH₂Cl | Me | H | H | 2 | H | H | OCHF₂ | N-Ph | CF₃ |
| CH₂Cl | Me | H | H | 2 | H | H | OCH₂CHF₂ | N-Ph | CF₃ |
| CH₂Cl | Me | H | H | 2 | H | H | OCH₂CF₃ | N-Ph | CF₃ |
| CH₂Cl | Me | H | H | 2 | H | H | CF₃ | N—CHF₂ | F |
| CH₂Cl | Me | H | H | 2 | H | H | CF₃ | N—CHF₂ | OMe |
| CH₂Cl | Me | H | H | 2 | H | H | CF₃ | N—CHF₂ | OCHF₂ |
| CH₂Cl | Me | H | H | 2 | H | H | Cl | N—CHF₂ | Cl |
| CH₂Cl | Me | H | H | 2 | H | H | F | N—CHF₂ | CF₃ |
| CH₂Cl | Me | H | H | 2 | H | H | OMe | N—CHF₂ | CF₃ |
| CH₂Cl | Me | H | H | 2 | H | H | OCHF₂ | N—CHF₂ | CF₃ |

TABLE 23

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | OCHF₂ | N—CHF₂ | OCHF₂ |
| CH₂Cl | Me | H | H | 2 | H | H | Cl | N-Et | Cl |
| CH₂Cl | Me | H | H | 2 | H | H | Cl | N-Pr-i | Cl |
| CH₂Cl | Me | H | H | 2 | H | H | Cl | N-Pr | Cl |
| CH₂Cl | Me | H | H | 2 | H | H | Cl | N—CH₂Pr-c | Cl |
| CH₂Cl | Me | H | H | 2 | H | H | Cl | N—CH₂C≡CH | Cl |
| CH₂Cl | Me | H | H | 2 | H | H | Cl | N—CH₂OMe | Cl |
| CH₂Cl | Me | H | H | 2 | H | H | OCHF₂ | N-Et | OCHF₂ |
| CH₂Cl | Me | H | H | 2 | H | H | OCHF₂ | N-Pr-i | OCHF₂ |
| CH₂Cl | Me | H | H | 2 | H | H | OCHF₂ | N-Pr | OCHF₂ |
| CH₂Cl | Me | H | H | 2 | H | H | OCHF₂ | N—CH₂Pr-c | OCHF₂ |
| CH₂Cl | Me | H | H | 2 | H | H | OCHF₂ | N—CH₂C≡CH | OCHF₂ |
| CH₂Cl | Me | H | H | 2 | H | H | OCHF₂ | N—CH₂OMe | OCHF₂ |
| CH₂Cl | Me | H | H | 2 | H | H | CF₃ | N—CH₂Pr-c | F |
| CH₂Cl | Me | H | H | 2 | H | H | CF₃ | N—CH₂Pr-c | OMe |
| CH₂Cl | Me | H | H | 2 | H | H | CF₃ | N—CH₂Pr-c | OCHF₂ |
| CH₂Cl | Me | H | H | 2 | H | H | F | N—CH₂Pr-c | CF₃ |
| CH₂Cl | Me | H | H | 2 | H | H | OMe | N—CH₂Pr-c | CF₃ |
| CH₂Cl | Me | H | H | 2 | H | H | OCHF₂ | N—CH₂Pr-c | CF₃ |
| CH₂Cl | Me | H | H | 1 | H | H | CF₃ | N—NH₂ | Cl |
| CH₂Cl | Me | H | H | 1 | H | H | Cl | N—NH₂ | CF₃ |
| CH₂Cl | Me | H | H | 1 | H | H | OH | N-Me | CF₃ |
| CH₂Cl | Me | H | H | 1 | H | H | OMe | N-Me | CF₃ |
| CH₂Cl | Me | H | H | 1 | H | H | OEt | N-Me | CF₃ |
| CH₂Cl | Me | H | H | 1 | H | H | OPr-i | N-Me | CF₃ |
| CH₂Cl | Me | H | H | 1 | H | H | OCHF₂ | N-Me | CF₃ |
| CH₂Cl | Me | H | H | 1 | H | H | OCH₂CHF₂ | N-Me | CF₃ |
| CH₂Cl | Me | H | H | 1 | H | H | OCH₂CF₃ | N-Me | CF₃ |
| CH₂Cl | Me | H | H | 1 | H | H | OCHF₂ | N-Me | OCHF₂ |
| CH₂Cl | Me | H | H | 1 | H | H | CF₃ | N-Me | CONH₂ |
| CH₂Cl | Me | H | H | 1 | H | H | CF₃ | N-Me | CONHMe |
| CH₂Cl | Me | H | H | 1 | H | H | CF₃ | N-Me | CONMe₂ |
| CH₂Cl | Me | H | H | 1 | H | H | CF₃ | N-Me | COOMe |
| CH₂Cl | Me | H | H | 1 | H | H | CF₃ | N-Me | COOEt |
| CH₂Cl | Me | H | H | 1 | H | H | CF₃ | N-Me | COOPr-i |

TABLE 24

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 1 | H | H | CF₃ | N-Me | COMe |
| CH₂Cl | Me | H | H | 1 | H | H | CF₃ | N-Me | COEt |
| CH₂Cl | Me | H | H | 1 | H | H | OCHF₂ | N-Ph | CF₃ |
| CH₂Cl | Me | H | H | 1 | H | H | OCH₂CHF₂ | N-Ph | CF₃ |
| CH₂Cl | Me | H | H | 1 | H | H | OCH₂CF₃ | N-Ph | CF₃ |
| CH₂Cl | Me | H | H | 1 | H | H | CF₃ | N—CHF₂ | F |
| CH₂Cl | Me | H | H | 1 | H | H | CF₃ | N—CHF₂ | OMe |
| CH₂Cl | Me | H | H | 1 | H | H | CF₃ | N—CHF₂ | OCHF₂ |
| CH₂Cl | Me | H | H | 1 | H | H | Cl | N—CHF₂ | Cl |
| CH₂Cl | Me | H | H | 1 | H | H | F | N—CHF₂ | CF₃ |
| CH₂Cl | Me | H | H | 1 | H | H | OMe | N—CHF₂ | CF₃ |
| CH₂Cl | Me | H | H | 1 | H | H | OCHF₂ | N—CHF₂ | CF₃ |
| CH₂Cl | Me | H | H | 1 | H | H | OCHF₂ | N—CHF₂ | OCHF₂ |
| CH₂Cl | Me | H | H | 1 | H | H | Cl | N-Et | Cl |
| CH₂Cl | Me | H | H | 1 | H | H | Cl | N-Pr-i | Cl |
| CH₂Cl | Me | H | H | 1 | H | H | Cl | N-Pr | Cl |
| CH₂Cl | Me | H | H | 1 | H | H | Cl | N—CH₂Pr-c | Cl |
| CH₂Cl | Me | H | H | 1 | H | H | Cl | N—CH₂C≡CH | Cl |
| CH₂Cl | Me | H | H | 1 | H | H | Cl | N—CH₂OMe | Cl |
| CH₂Cl | Me | H | H | 1 | H | H | OCHF₂ | N-Et | OCHF₂ |
| CH₂Cl | Me | H | H | 1 | H | H | OCHF₂ | N-Pr-i | OCHF₂ |
| CH₂Cl | Me | H | H | 1 | H | H | OCHF₂ | N-Pr | OCHF₂ |
| CH₂Cl | Me | H | H | 1 | H | H | OCHF₂ | N—CH₂Pr-c | OCHF₂ |
| CH₂Cl | Me | H | H | 1 | H | H | OCHF₂ | N—CH₂C≡CH | OCHF₂ |
| CH₂Cl | Me | H | H | 1 | H | H | OCHF₂ | N—CH₂OMe | OCHF₂ |
| CH₂Cl | Me | H | H | 1 | H | H | CF₃ | N—CH₂Pr-c | F |
| CH₂Cl | Me | H | H | 1 | H | H | CF₃ | N—CH₂Pr-c | OMe |
| CH₂Cl | Me | H | H | 1 | H | H | CF₃ | N—CH₂Pr-c | OCHF₂ |
| CH₂Cl | Me | H | H | 1 | H | H | F | N—CH₂Pr-c | CF₃ |
| CH₂Cl | Me | H | H | 1 | H | H | OMe | N—CH₂Pr-c | CF₃ |
| CH₂Cl | Me | H | H | 1 | H | H | OCHF₂ | N—CH₂Pr-c | CF₃ |
| CH₂Cl | Me | H | H | 0 | H | H | CF₃ | N—NH₂ | Cl |
| CH₂Cl | Me | H | H | 0 | H | H | Cl | N—NH₂ | CF₃ |
| CH₂Cl | Me | H | H | 0 | H | H | OH | N-Me | CF₃ |
| CH₂Cl | Me | H | H | 0 | H | H | OMe | N-Me | CF₃ |

TABLE 25

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | OEt | N-Me | CF₃ |
| CH₂Cl | Me | H | H | 0 | H | H | OPr-i | N-Me | CF₃ |
| CH₂Cl | Me | H | H | 0 | H | H | OCHF₂ | N-Me | CF₃ |
| CH₂Cl | Me | H | H | 0 | H | H | OCH₂CHF₂ | N-Me | CF₃ |
| CH₂Cl | Me | H | H | 0 | H | H | OCH₂CF₃ | N-Me | CF₃ |
| CH₂Cl | Me | H | H | 0 | H | H | OCHF₂ | N-Me | OCHF₂ |
| CH₂Cl | Me | H | H | 0 | H | H | CF₃ | N-Me | CONH₂ |
| CH₂Cl | Me | H | H | 0 | H | H | CF₃ | N-Me | CONHMe |
| CH₂Cl | Me | H | H | 0 | H | H | CF₃ | N-Me | CONMe₂ |
| CH₂Cl | Me | H | H | 0 | H | H | CF₃ | N-Me | COOMe |
| CH₂Cl | Me | H | H | 0 | H | H | CF₃ | N-Me | COOEt |
| CH₂Cl | Me | H | H | 0 | H | H | CF₃ | N-Me | COOPr-i |
| CH₂Cl | Me | H | H | 0 | H | H | CF₃ | N-Me | COMe |
| CH₂Cl | Me | H | H | 0 | H | H | CF₃ | N-Me | COEt |
| CH₂Cl | Me | H | H | 0 | H | H | OCHF₂ | N-Ph | CF₃ |
| CH₂Cl | Me | H | H | 0 | H | H | OCH₂CHF₂ | N-Ph | CF₃ |
| CH₂Cl | Me | H | H | 0 | H | H | OCH₂CF₃ | N-Ph | CF₃ |
| CH₂Cl | Me | H | H | 0 | H | H | CF₃ | N—CHF₂ | F |
| CH₂Cl | Me | H | H | 0 | H | H | CF₃ | N—CHF₂ | OMe |
| CH₂Cl | Me | H | H | 0 | H | H | CF₃ | N—CHF₂ | OCHF₂ |
| CH₂Cl | Me | H | H | 0 | H | H | Cl | N—CHF₂ | Cl |
| CH₂Cl | Me | H | H | 0 | H | H | F | N—CHF₂ | CF₃ |
| CH₂Cl | Me | H | H | 0 | H | H | OMe | N—CHF₂ | CF₃ |
| CH₂Cl | Me | H | H | 0 | H | H | OCHF₂ | N—CHF₂ | CF₃ |
| CH₂Cl | Me | H | H | 0 | H | H | OCHF₂ | N—CHF₂ | OCHF₂ |
| CH₂Cl | Me | H | H | 0 | H | H | Cl | N-Et | Cl |
| CH₂Cl | Me | H | H | 0 | H | H | Cl | N-Pr-i | Cl |
| CH₂Cl | Me | H | H | 0 | H | H | Cl | N-Pr | Cl |
| CH₂Cl | Me | H | H | 0 | H | H | Cl | N—CH₂Pr-c | Cl |
| CH₂Cl | Me | H | H | 0 | H | H | Cl | N—CH₂C≡CH | Cl |
| CH₂Cl | Me | H | H | 0 | H | H | Cl | N—CH₂OMe | Cl |
| CH₂Cl | Me | H | H | 0 | H | H | OCHF₂ | N-Et | OCHF₂ |
| CH₂Cl | Me | H | H | 0 | H | H | OCHF₂ | N-Pr-i | OCHF₂ |
| CH₂Cl | Me | H | H | 0 | H | H | OCHF₂ | N-Pr | OCHF₂ |
| CH₂Cl | Me | H | H | 0 | H | H | OCHF₂ | N—CH₂Pr-c | OCHF₂ |

TABLE 26

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | OCHF₂ | N—CH₂C≡CH | OCHF₂ |
| CH₂Cl | Me | H | H | 0 | H | H | OCHF₂ | N—CH₂OMe | OCHF₂ |
| CH₂Cl | Me | H | H | 0 | H | H | CF₃ | N—CH₂Pr-c | F |
| CH₂Cl | Me | H | H | 0 | H | H | CF₃ | N—CH₂Pr-c | OMe |
| CH₂Cl | Me | H | H | 0 | H | H | CF₃ | N—CH₂Pr-c | OCHF₂ |
| CH₂Cl | Me | H | H | 0 | H | H | F | N—CH₂Pr-c | CF₃ |
| CH₂Cl | Me | H | H | 0 | H | H | OMe | N—CH₂Pr-c | CF₃ |
| CH₂Cl | Me | H | H | 0 | H | H | OCHF₂ | N—CH₂Pr-c | CF₃ |
| CH₂Cl | Me | H | H | 2 | H | H | CF₃ | N—(CH₂)₂O— | |
| CH₂Cl | Me | H | H | 2 | H | H | CF₃ | N—(CH₂)₃O— | |
| CH₂Cl | Me | H | H | 2 | H | H | CF₃ | N—(CH₂)₂S— | |
| CH₂Cl | Me | H | H | 2 | H | H | CF₃ | N—(CH₂)₂SO₂— | |
| CH₂Cl | Me | H | H | 2 | H | H | Cl | N—(CH₂)₂O— | |
| CH₂Cl | Me | H | H | 2 | H | H | Cl | N—(CH₂)₃O— | |
| CH₂Cl | Me | H | H | 2 | H | H | Cl | N—(CH₂)₂S— | |
| CH₂Cl | Me | H | H | 2 | H | H | Cl | N—(CH₂)₂SO₂— | |
| CH₂Cl | Me | H | H | 1 | H | H | CF₃ | N—(CH₂)₂O— | |
| CH₂Cl | Me | H | H | 1 | H | H | CF₃ | N—(CH₂)₃O— | |
| CH₂Cl | Me | H | H | 1 | H | H | CF₃ | N—(CH₂)₂S— | |
| CH₂Cl | Me | H | H | 1 | H | H | CF₃ | N—(CH₂)₂SO₂— | |
| CH₂Cl | Me | H | H | 1 | H | H | Cl | N—(CH₂)₂O— | |
| CH₂Cl | Me | H | H | 1 | H | H | Cl | N—(CH₂)₃O— | |
| CH₂Cl | Me | H | H | 1 | H | H | Cl | N—(CH₂)₂S— | |
| CH₂Cl | Me | H | H | 1 | H | H | Cl | N—(CH₂)₂SO₂— | |
| CH₂Cl | Me | H | H | 0 | H | H | CF₃ | N—(CH₂)₂O— | |
| CH₂Cl | Me | H | H | 0 | H | H | CF₃ | N—(CH₂)₃O— | |
| CH₂Cl | Me | H | H | 0 | H | H | CF₃ | N—(CH₂)₂S— | |
| CH₂Cl | Me | H | H | 0 | H | H | CF₃ | N—(CH₂)₂SO₂— | |
| CH₂Cl | Me | H | H | 0 | H | H | Cl | N—(CH₂)₂O— | |
| CH₂Cl | Me | H | H | 0 | H | H | Cl | N—(CH₂)₃O— | |
| CH₂Cl | Me | H | H | 0 | H | H | Cl | N—(CH₂)₂S— | |
| CH₂Cl | Me | H | H | 0 | H | H | Cl | N—(CH₂)₂SO₂— | |
| CH₂Cl | Me | H | H | 2 | H | H | CF₃ | N-Et | F |
| CH₂Cl | Me | H | H | 2 | H | H | F | N-Et | CF₃ |
| CH₂Cl | Me | H | H | 2 | H | H | CF₃ | N-Et | Br |

TABLE 27

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | Br | N-Et | CF₃ |
| CH₂Cl | Me | H | H | 2 | H | H | CF₃ | N-Et | CF₃ |
| CH₂Cl | Me | H | H | 2 | H | H | CF₃ | N-Et | CN |
| CH₂Cl | Me | H | H | 2 | H | H | CN | N-Et | CF₃ |
| CH₂Cl | Me | H | H | 2 | H | H | CF₃ | N-Et | Me |
| CH₂Cl | Me | H | H | 2 | H | H | Me | N-Et | CF₃ |
| CH₂Cl | Me | H | H | 2 | H | H | CF₃ | N-Et | Et |
| CH₂Cl | Me | H | H | 2 | H | H | Et | N-Et | CF₃ |
| CH₂Cl | Me | H | H | 2 | H | H | CF₃ | N-Et | OH |
| CH₂Cl | Me | H | H | 2 | H | H | CF₃ | N-Et | OMe |
| CH₂Cl | Me | H | H | 2 | H | H | OMe | N-Et | CF₃ |
| CH₂Cl | Me | H | H | 2 | H | H | CF₃ | N-Et | OEt |
| CH₂Cl | Me | H | H | 2 | H | H | OEt | N-Et | CF₃ |
| CH₂Cl | Me | H | H | 2 | H | H | CF₃ | N-Et | OPr-i |
| CH₂Cl | Me | H | H | 2 | H | H | OPr-i | N-Et | CF₃ |
| CH₂Cl | Me | H | H | 2 | H | H | CF₃ | N-Et | OPr |
| CH₂Cl | Me | H | H | 2 | H | H | CF₃ | N-Et | OBu-t |
| CH₂Cl | Me | H | H | 2 | H | H | CF₃ | N-Et | OPh |
| CH₂Cl | Me | H | H | 2 | H | H | CF₃ | N-Et | OCH₂Ph |
| CH₂Cl | Me | H | H | 2 | H | H | CF₃ | N-Et | OCH₂CH=CH₂ |
| CH₂Cl | Me | H | H | 2 | H | H | CF₃ | N-Et | OCH(Me)CH=CH₂ |
| CH₂Cl | Me | H | H | 2 | H | H | CF₃ | N-Et | OCH₂C≡CH |
| CH₂Cl | Me | H | H | 2 | H | H | CF₃ | N-Et | OCH(Me)C≡CH |
| CH₂Cl | Me | H | H | 2 | H | H | CF₃ | N-Et | OCHF₂ |
| CH₂Cl | Me | H | H | 2 | H | H | OCHF₂ | N-Et | CF₃ |
| CH₂Cl | Me | H | H | 2 | H | H | CF₃ | N-Et | OCH₂CF₃ |
| CH₂Cl | Me | H | H | 2 | H | H | CF₃ | N-Et | OCH₂CHF₂ |
| CH₂Cl | Me | H | H | 2 | H | H | OCH₂CHF₂ | N-Et | CF₃ |
| CH₂Cl | Me | H | H | 2 | H | H | CF₃ | N-Et | SMe |
| CH₂Cl | Me | H | H | 2 | H | H | CF₃ | N-Et | SOMe |
| CH₂Cl | Me | H | H | 2 | H | H | CF₃ | N-Et | SO₂Me |
| CH₂Cl | Me | H | H | 2 | H | H | CF₃ | N-Et | SEt |
| CH₂Cl | Me | H | H | 2 | H | H | CF₃ | N-Et | SOEt |
| CH₂Cl | Me | H | H | 2 | H | H | CF₃ | N-Et | SO₂Et |
| CH₂Cl | Me | H | H | 2 | H | H | CF₃ | N-Et | SPr-i |

TABLE 28

| R¹ | R² | R³ | R⁴ | n | R⁵ | R⁶ | R¹⁵ | Z² | R¹⁶ |
|---|---|---|---|---|---|---|---|---|---|
| $CH_2Cl$ | Me | H | H | 2 | H | H | $CF_3$ | N-Et | $SOPr$-i |
| $CH_2Cl$ | Me | H | H | 2 | H | H | $CF_3$ | N-Et | $SO_2Pr$-i |
| $CH_2Cl$ | Me | H | H | 2 | H | H | $CF_3$ | N-Et | $SCF_3$ |
| $CH_2Cl$ | Me | H | H | 2 | H | H | $CF_3$ | N-Et | $SOCF_3$ |
| $CH_2Cl$ | Me | H | H | 2 | H | H | $CF_3$ | N-Et | $SO_2CF_3$ |
| $CH_2Cl$ | Me | H | H | 2 | H | H | $CF_3$ | N-Et | $SCHF_2$ |
| $CH_2Cl$ | Me | H | H | 2 | H | H | $CF_3$ | N-Et | $SOCHF_2$ |
| $CH_2Cl$ | Me | H | H | 2 | H | H | $CF_3$ | N-Et | $SO_2CHF_2$ |
| $CH_2Cl$ | Me | H | H | 2 | H | H | $CHF_2$ | N-Et | Cl |
| $CH_2Cl$ | Me | H | H | 2 | H | H | $CHF_2$ | N-Et | OMe |
| $CH_2Cl$ | Me | H | H | 2 | H | H | $CHF_2$ | N-Et | $OCHF_2$ |
| $CH_2Cl$ | Me | H | H | 2 | H | H | $CHF_2$ | N-Et | CN |
| $CH_2Cl$ | Me | H | H | 2 | H | H | $CHF_2$ | N-Et | Me |
| $CH_2Cl$ | Me | H | H | 2 | H | H | Me | N-Et | Cl |
| $CH_2Cl$ | Me | H | H | 2 | H | H | Me | N-Et | OMe |
| $CH_2Cl$ | Me | H | H | 2 | H | H | Me | N-Et | $OCHF_2$ |
| $CH_2Cl$ | Me | H | H | 2 | H | H | Me | N-Et | CN |
| $CH_2Cl$ | Me | H | H | 2 | H | H | Me | N-Et | Me |

TABLE 28-continued

| R¹ | R² | R³ | R⁴ | n | R⁵ | R⁶ | R¹⁵ | Z² | R¹⁶ |
|---|---|---|---|---|---|---|---|---|---|
| $CH_2Cl$ | Me | H | H | 2 | H | H | Et | N-Et | Cl |
| $CH_2Cl$ | Me | H | H | 2 | H | H | Et | N-Et | OMe |
| $CH_2Cl$ | Me | H | H | 2 | H | H | Et | N-Et | $OCHF_2$ |
| $CH_2Cl$ | Me | H | H | 2 | H | H | Et | N-Et | CN |
| $CH_2Cl$ | Me | H | H | 2 | H | H | Et | N-Et | Me |
| $CH_2Cl$ | Me | H | H | 2 | H | H | $OCHF_2$ | N-Et | Cl |
| $CH_2Cl$ | Me | H | H | 0 | H | H | $CF_3$ | N-Et | F |
| $CH_2Cl$ | Me | H | H | 0 | H | H | F | N-Et | $CF_3$ |
| $CH_2Cl$ | Me | H | H | 0 | H | H | $CF_3$ | N-Et | Br |
| $CH_2Cl$ | Me | H | H | 0 | H | H | Br | N-Et | $CF_3$ |
| $CH_2Cl$ | Me | H | H | 0 | H | H | $CF_3$ | N-Et | $CF_3$ |
| $CH_2Cl$ | Me | H | H | 0 | H | H | $CF_3$ | N-Et | CN |
| $CH_2Cl$ | Me | H | H | 0 | H | H | CN | N-Et | $CF_3$ |
| $CH_2Cl$ | Me | H | H | 0 | H | H | $CF_3$ | N-Et | Me |
| $CH_2Cl$ | Me | H | H | 0 | H | H | Me | N-Et | $CF_3$ |
| $CH_2Cl$ | Me | H | H | 0 | H | H | $CF_3$ | N-Et | Et |
| $CH_2Cl$ | Me | H | H | 0 | H | H | Et | N-Et | $CF_3$ |

TABLE 29

| R¹ | R² | R³ | R⁴ | n | R⁵ | R⁶ | R¹⁵ | Z² | R¹⁶ |
|---|---|---|---|---|---|---|---|---|---|
| $CH_2Cl$ | Me | H | H | 0 | H | H | $CF_3$ | N-Et | OH |
| $CH_2Cl$ | Me | H | H | 0 | H | H | $CF_3$ | N-Et | OMe |
| $CH_2Cl$ | Me | H | H | 0 | H | H | OMe | N-Et | $CF_3$ |
| $CH_2Cl$ | Me | H | H | 0 | H | H | $CF_3$ | N-Et | OEt |
| $CH_2Cl$ | Me | H | H | 0 | H | H | OEt | N-Et | $CF_3$ |
| $CH_2Cl$ | Me | H | H | 0 | H | H | $CF_3$ | N-Et | $OPr$-i |
| $CH_2Cl$ | Me | H | H | 0 | H | H | $OPr$-i | N-Et | $CF_3$ |
| $CH_2Cl$ | Me | H | H | 0 | H | H | $CF_3$ | N-Et | OPr |
| $CH_2Cl$ | Me | H | H | 0 | H | H | $CF_3$ | N-Et | $OBu$-t |
| $CH_2Cl$ | Me | H | H | 0 | H | H | $CF_3$ | N-Et | OPh |
| $CH_2Cl$ | Me | H | H | 0 | H | H | $CF_3$ | N-Et | $OCH_2Ph$ |
| $CH_2Cl$ | Me | H | H | 0 | H | H | $CF_3$ | N-Et | $OCH_2CH{=}CH_2$ |
| $CH_2Cl$ | Me | H | H | 0 | H | H | $CF_3$ | N-Et | $OCH(Me)CH{=}CH_2$ |
| $CH_2Cl$ | Me | H | H | 0 | H | H | $CF_3$ | N-Et | $OCH_2C{\equiv}CH$ |
| $CH_2Cl$ | Me | H | H | 0 | H | H | $CF_3$ | N-Et | $OCH(Me)C{\equiv}CH$ |
| $CH_2Cl$ | Me | H | H | 0 | H | H | $CF_3$ | N-Et | $OCHF_2$ |
| $CH_2Cl$ | Me | H | H | 0 | H | H | $OCHF_2$ | N-Et | $CF_3$ |
| $CH_2Cl$ | Me | H | H | 0 | H | H | $CF_3$ | N-Et | $OCH_2CF_3$ |
| $CH_2Cl$ | Me | H | H | 0 | H | H | $CF_3$ | N-Et | $OCH_2CHF_2$ |
| $CH_2Cl$ | Me | H | H | 0 | H | H | $OCH_2CHF_2$ | N-Et | $CF_3$ |
| $CH_2Cl$ | Me | H | H | 0 | H | H | $CF_3$ | N-Et | SMe |
| $CH_2Cl$ | Me | H | H | 0 | H | H | $CF_3$ | N-Et | SOMe |
| $CH_2Cl$ | Me | H | H | 0 | H | H | $CF_3$ | N-Et | $SO_2Me$ |
| $CH_2Cl$ | Me | H | H | 0 | H | H | $CF_3$ | N-Et | SEt |
| $CH_2Cl$ | Me | H | H | 0 | H | H | $CF_3$ | N-Et | SOEt |
| $CH_2Cl$ | Me | H | H | 0 | H | H | $CF_3$ | N-Et | $SO_2Et$ |
| $CH_2Cl$ | Me | H | H | 0 | H | H | $CF_3$ | N-Et | $SPr$-i |
| $CH_2Cl$ | Me | H | H | 0 | H | H | $CF_3$ | N-Et | $SOPr$-i |
| $CH_2Cl$ | Me | H | H | 0 | H | H | $CF_3$ | N-Et | $SO_2Pr$-i |
| $CH_2Cl$ | Me | H | H | 0 | H | H | $CF_3$ | N-Et | $SCF_3$ |
| $CH_2Cl$ | Me | H | H | 0 | H | H | $CF_3$ | N-Et | $SOCF_3$ |
| $CH_2Cl$ | Me | H | H | 0 | H | H | $CF_3$ | N-Et | $SO_2CF_3$ |
| $CH_2Cl$ | Me | H | H | 0 | H | H | $CF_3$ | N-Et | $SCHF_2$ |
| $CH_2Cl$ | Me | H | H | 0 | H | H | $CF_3$ | N-Et | $SOCHF_2$ |
| $CH_2Cl$ | Me | H | H | 0 | H | H | $CF_3$ | N-Et | $SO_2CHF_2$ |

TABLE 30

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 0 | H | H | CHF₂ | N-Et | Cl |
| CH₂Cl | Me | H | H | 0 | H | H | CHF₂ | N-Et | OMe |
| CH₂Cl | Me | H | H | 0 | H | H | CHF₂ | N-Et | OCHF₂ |
| CH₂Cl | Me | H | H | 0 | H | H | CHF₂ | N-Et | CN |
| CH₂Cl | Me | H | H | 0 | H | H | CHF₂ | N-Et | Me |
| CH₂Cl | Me | H | H | 0 | H | H | Me | N-Et | Cl |
| CH₂Cl | Me | H | H | 0 | H | H | Me | N-Et | OMe |
| CH₂Cl | Me | H | H | 0 | H | H | Me | N-Et | OCHF₂ |
| CH₂Cl | Me | H | H | 0 | H | H | Me | N-Et | CN |
| CH₂Cl | Me | H | H | 0 | H | H | Me | N-Et | Me |
| CH₂Cl | Me | H | H | 0 | H | H | Et | N-Et | Cl |
| CH₂Cl | Me | H | H | 0 | H | H | Et | N-Et | OMe |
| CH₂Cl | Me | H | H | 0 | H | H | Et | N-Et | OCHF₂ |
| CH₂Cl | Me | H | H | 0 | H | H | Et | N-Et | CN |
| CH₂Cl | Me | H | H | 0 | H | H | Et | N-Et | Me |
| CH₂Cl | Me | H | H | 0 | H | H | OCHF₂ | N-Et | Cl |
| CH₂Cl | Me | H | H | 2 | H | H | CF₃ | N-Me | Et |
| CH₂Cl | Me | H | H | 2 | H | H | Me | N-Me | CF₃ |
| CH₂Cl | Me | H | H | 2 | H | H | CF₃ | N-Me | Br |
| CH₂Cl | Me | H | H | 2 | H | H | Br | N-Me | CF₃ |
| CH₂Cl | Me | H | H | 0 | H | H | CF₃ | N-Me | Et |
| CH₂Cl | Me | H | H | 0 | H | H | Me | N-Me | CF₃ |
| CH₂Cl | Me | H | H | 0 | H | H | CF₃ | N-Me | Br |
| CH₂Cl | Me | H | H | 0 | H | H | Br | N-Me | CF₃ |
| CH₂Cl | Me | H | H | 2 | H | H | CF₃ | N-Pr-i | F |
| CH₂Cl | Me | H | H | 2 | H | H | F | N-Pr-i | CF₃ |
| CH₂Cl | Me | H | H | 2 | H | H | CF₃ | N-Pr-i | Br |
| CH₂Cl | Me | H | H | 2 | H | H | Br | N-Pr-i | CF₃ |
| CH₂Cl | Me | H | H | 2 | H | H | CF₃ | N-Pr-i | CF₃ |
| CH₂Cl | Me | H | H | 2 | H | H | CF₃ | N-Pr-i | CN |
| CH₂Cl | Me | H | H | 2 | H | H | CN | N-Pr-i | CF₃ |
| CH₂Cl | Me | H | H | 2 | H | H | CF₃ | N-Pr-i | Me |
| CH₂Cl | Me | H | H | 2 | H | H | Me | N-Pr-i | CF₃ |
| CH₂Cl | Me | H | H | 2 | H | H | CF₃ | N-Pr-i | Et |
| CH₂Cl | Me | H | H | 2 | H | H | Et | N-Pr-i | CF₃ |

TABLE 31

| R¹ | R² | R³ | R⁴ | n | R⁵ | R⁶ | R¹⁵ | Z² | R¹⁶ |
|---|---|---|---|---|---|---|---|---|---|
| CH₂Cl | Me | H | H | 2 | H | H | CF₃ | N-Pr-i | OH |
| CH₂Cl | Me | H | H | 2 | H | H | CF₃ | N-Pr-i | OMe |
| CH₂Cl | Me | H | H | 2 | H | H | OMe | N-Pr-i | CF₃ |
| CH₂Cl | Me | H | H | 2 | H | H | CF₃ | N-Pr-i | OEt |
| CH₂Cl | Me | H | H | 2 | H | H | OEt | N-Pr-i | CF₃ |
| CH₂Cl | Me | H | H | 2 | H | H | CF₃ | N-Pr-i | OPr-i |
| CH₂Cl | Me | H | H | 2 | H | H | OPr-i | N-Pr-i | CF₃ |
| CH₂Cl | Me | H | H | 2 | H | H | CF₃ | N-Pr-i | OPr |
| CH₂Cl | Me | H | H | 2 | H | H | CF₃ | N-Pr-i | OBu-t |
| CH₂Cl | Me | H | H | 2 | H | H | CF₃ | N-Pr-i | OPh |
| CH₂Cl | Me | H | H | 2 | H | H | CF₃ | N-Pr-i | OCH₂Ph |
| CH₂Cl | Me | H | H | 2 | H | H | CF₃ | N-Pr-i | OCH₂CH=CH₂ |
| CH₂Cl | Me | H | H | 2 | H | H | CF₃ | N-Pr-i | OCH(Me)CH=CH₂ |
| CH₂Cl | Me | H | H | 2 | H | H | CF₃ | N-Pr-i | OCH₂C≡CH |
| CH₂Cl | Me | H | H | 2 | H | H | CF₃ | N-Pr-i | OCH(Me)C≡CH |
| CH₂Cl | Me | H | H | 2 | H | H | CF₃ | N-Pr-i | OCHF₂ |
| CH₂Cl | Me | H | H | 2 | H | H | OCHF₂ | N-Pr-i | CF₃ |
| CH₂Cl | Me | H | H | 2 | H | H | CF₃ | N-Pr-i | OCH₂CF₃ |
| CH₂Cl | Me | H | H | 2 | H | H | CF₃ | N-Pr-i | OCH₂CHF₂ |
| CH₂Cl | Me | H | H | 2 | H | H | OCH₂CHF₂ | N-Pr-i | CF₃ |
| CH₂Cl | Me | H | H | 2 | H | H | CF₃ | N-Pr-i | SMe |
| CH₂Cl | Me | H | H | 2 | H | H | CF₃ | N-Pr-i | SOMe |
| CH₂Cl | Me | H | H | 2 | H | H | CF₃ | N-Pr-i | SO₂Me |
| CH₂Cl | Me | H | H | 2 | H | H | CF₃ | N-Pr-i | SEt |
| CH₂Cl | Me | H | H | 2 | H | H | CF₃ | N-Pr-i | SOEt |
| CH₂Cl | Me | H | H | 2 | H | H | CF₃ | N-Pr-i | SO₂Et |
| CH₂Cl | Me | H | H | 2 | H | H | CF₃ | N-Pr-i | SPr-i |
| CH₂Cl | Me | H | H | 2 | H | H | CF₃ | N-Pr-i | SOPr-i |
| CH₂Cl | Me | H | H | 2 | H | H | CF₃ | N-Pr-i | SO₂Pr-i |
| CH₂Cl | Me | H | H | 2 | H | H | CF₃ | N-Pr-i | SCF₃ |
| CH₂Cl | Me | H | H | 2 | H | H | CF₃ | N-Pr-i | SOCF₃ |
| CH₂Cl | Me | H | H | 2 | H | H | CF₃ | N-Pr-i | SO₂CF₃ |
| CH₂Cl | Me | H | H | 2 | H | H | CF₃ | N-Pr-i | SCHF₂ |
| CH₂Cl | Me | H | H | 2 | H | H | CF₃ | N-Pr-i | SOCHF₂ |
| CH₂Cl | Me | H | H | 2 | H | H | CF₃ | N-Pr-i | SO₂CHF₂ |

TABLE 32

| R$^1$ | R$^2$ | R$^3$ | R$^4$ | n | R$^5$ | R$^6$ | R$^{15}$ | Z$^2$ | R$^{16}$ |
|---|---|---|---|---|---|---|---|---|---|
| CH$_2$Cl | Me | H | H | 2 | H | H | CHF$_2$ | N-Pr-i | Cl |
| CH$_2$Cl | Me | H | H | 2 | H | H | CHF$_2$ | N-Pr-i | OMe |
| CH$_2$Cl | Me | H | H | 2 | H | H | CHF$_2$ | N-Pr-i | OCHF$_2$ |
| CH$_2$Cl | Me | H | H | 2 | H | H | CHF$_2$ | N-Pr-i | CN |
| CH$_2$Cl | Me | H | H | 2 | H | H | CHF$_2$ | N-Pr-i | Me |
| CH$_2$Cl | Me | H | H | 2 | H | H | Me | N-Pr-i | Cl |
| CH$_2$Cl | Me | H | H | 2 | H | H | Me | N-Pr-i | OMe |
| CH$_2$Cl | Me | H | H | 2 | H | H | Me | N-Pr-i | OCHF$_2$ |
| CH$_2$Cl | Me | H | H | 2 | H | H | Me | N-Pr-i | CN |
| CH$_2$Cl | Me | H | H | 2 | H | H | Me | N-Pr-i | Me |
| CH$_2$Cl | Me | H | H | 2 | H | H | Et | N-Pr-i | Cl |
| CH$_2$Cl | Me | H | H | 2 | H | H | Et | N-Pr-i | OMe |
| CH$_2$Cl | Me | H | H | 2 | H | H | Et | N-Pr-i | OCHF$_2$ |
| CH$_2$Cl | Me | H | H | 2 | H | H | Et | N-Pr-i | CN |
| CH$_2$Cl | Me | H | H | 2 | H | H | Et | N-Pr-i | Me |
| CH$_2$Cl | Me | H | H | 2 | H | H | OCHF$_2$ | N-Pr-i | Cl |
| CH$_2$Cl | Me | H | H | 0 | H | H | CF$_3$ | N-Pr-i | F |
| CH$_2$Cl | Me | H | H | 0 | H | H | F | N-Pr-i | CF$_3$ |
| CH$_2$Cl | Me | H | H | 0 | H | H | CF$_3$ | N-Pr-i | Br |
| CH$_2$Cl | Me | H | H | 0 | H | H | Br | N-Pr-i | CF$_3$ |
| CH$_2$Cl | Me | H | H | 0 | H | H | CF$_3$ | N-Pr-i | CF$_3$ |
| CH$_2$Cl | Me | H | H | 0 | H | H | CF$_3$ | N-Pr-i | CN |
| CH$_2$Cl | Me | H | H | 0 | H | H | CN | N-Pr-i | CF$_3$ |
| CH$_2$Cl | Me | H | H | 0 | H | H | CF$_3$ | N-Pr-i | Me |
| CH$_2$Cl | Me | H | H | 0 | H | H | Me | N-Pr-i | CF$_3$ |
| CH$_2$Cl | Me | H | H | 0 | H | H | CF$_3$ | N-Pr-i | Et |
| CH$_2$Cl | Me | H | H | 0 | H | H | Et | N-Pr-i | CF$_3$ |
| CH$_2$Cl | Me | H | H | 0 | H | H | CF$_3$ | N-Pr-i | OH |
| CH$_2$Cl | Me | H | H | 0 | H | H | CF$_3$ | N-Pr-i | OMe |
| CH$_2$Cl | Me | H | H | 0 | H | H | OMe | N-Pr-i | CF$_3$ |
| CH$_2$Cl | Me | H | H | 0 | H | H | CF$_3$ | N-Pr-i | OEt |
| CH$_2$Cl | Me | H | H | 0 | H | H | OEt | N-Pr-i | CF$_3$ |
| CH$_2$Cl | Me | H | H | 0 | H | H | CF$_3$ | N-Pr-i | OPr-i |
| CH$_2$Cl | Me | H | H | 0 | H | H | OPr-i | N-Pr-i | CF$_3$ |
| CH$_2$Cl | Me | H | H | 0 | H | H | CF$_3$ | N-Pr-i | OPr |

TABLE 33

| R$^1$ | R$^2$ | R$^3$ | R$^4$ | n | R$^5$ | R$^6$ | R$^{15}$ | Z$^2$ | R$^{16}$ |
|---|---|---|---|---|---|---|---|---|---|
| CH$_2$Cl | Me | H | H | 0 | H | H | CF$_3$ | N-Pr-i | OBu-t |
| CH$_2$Cl | Me | H | H | 0 | H | H | CF$_3$ | N-Pr-i | OPh |
| CH$_2$Cl | Me | H | H | 0 | H | H | CF$_3$ | N-Pr-i | OCH$_2$Ph |
| CH$_2$Cl | Me | H | H | 0 | H | H | CF$_3$ | N-Pr-i | OCH$_2$CH=CH$_2$ |
| CH$_2$Cl | Me | H | H | 0 | H | H | CF$_3$ | N-Pr-i | OCH(Me)CH=CH$_2$ |
| CH$_2$Cl | Me | H | H | 0 | H | H | CF$_3$ | N-Pr-i | OCH$_2$C≡CH |
| CH$_2$Cl | Me | H | H | 0 | H | H | CF$_3$ | N-Pr-i | OCH(Me)C≡CH |
| CH$_2$Cl | Me | H | H | 0 | H | H | CF$_3$ | N-Pr-i | OCHF$_2$ |
| CH$_2$Cl | Me | H | H | 0 | H | H | OCHF$_2$ | N-Pr-i | CF$_3$ |
| CH$_2$Cl | Me | H | H | 0 | H | H | CF$_3$ | N-Pr-i | OCH$_2$CF$_3$ |
| CH$_2$Cl | Me | H | H | 0 | H | H | CF$_3$ | N-Pr-i | OCH$_2$CHF$_2$ |
| CH$_2$Cl | Me | H | H | 0 | H | H | OCH$_2$CHF$_2$ | N-Pr-i | CF$_3$ |
| CH$_2$Cl | Me | H | H | 0 | H | H | CF$_3$ | N-Pr-i | SMe |
| CH$_2$Cl | Me | H | H | 0 | H | H | CF$_3$ | N-Pr-i | SOMe |
| CH$_2$Cl | Me | H | H | 0 | H | H | CF$_3$ | N-Pr-i | SO$_2$Me |
| CH$_2$Cl | Me | H | H | 0 | H | H | CF$_3$ | N-Pr-i | SEt |
| CH$_2$Cl | Me | H | H | 0 | H | H | CF$_3$ | N-Pr-i | SOEt |
| CH$_2$Cl | Me | H | H | 0 | H | H | CF$_3$ | N-Pr-i | SO$_2$Et |
| CH$_2$Cl | Me | H | H | 0 | H | H | CF$_3$ | N-Pr-i | SPr-i |
| CH$_2$Cl | Me | H | H | 0 | H | H | CF$_3$ | N-Pr-i | SOPr-i |
| CH$_2$Cl | Me | H | H | 0 | H | H | CF$_3$ | N-Pr-i | SO$_2$Pr-i |
| CH$_2$Cl | Me | H | H | 0 | H | H | CF$_3$ | N-Pr-i | SCF$_3$ |
| CH$_2$Cl | Me | H | H | 0 | H | H | CF$_3$ | N-Pr-i | SOCF$_3$ |
| CH$_2$Cl | Me | H | H | 0 | H | H | CF$_3$ | N-Pr-i | SO$_2$CF$_3$ |
| CH$_2$Cl | Me | H | H | 0 | H | H | CF$_3$ | N-Pr-i | SCHF$_2$ |
| CH$_2$Cl | Me | H | H | 0 | H | H | CF$_3$ | N-Pr-i | SOCHF$_2$ |
| CH$_2$Cl | Me | H | H | 0 | H | H | CF$_3$ | N-Pr-i | SO$_2$CHF$_2$ |
| CH$_2$Cl | Me | H | H | 0 | H | H | CHF$_2$ | N-Pr-i | Cl |
| CH$_2$Cl | Me | H | H | 0 | H | H | CHF$_2$ | N-Pr-i | OMe |
| CH$_2$Cl | Me | H | H | 0 | H | H | CHF$_2$ | N-Pr-i | OCHF$_2$ |
| CH$_2$Cl | Me | H | H | 0 | H | H | CHF$_2$ | N-Pr-i | CN |
| CH$_2$Cl | Me | H | H | 0 | H | H | CHF$_2$ | N-Pr-i | Me |
| CH$_2$Cl | Me | H | H | 0 | H | H | Me | N-Pr-i | Cl |
| CH$_2$Cl | Me | H | H | 0 | H | H | Me | N-Pr-i | OMe |
| CH$_2$Cl | Me | H | H | 0 | H | H | Me | N-Pr-i | OCHF$_2$ |

TABLE 34

| R$^1$ | R$^2$ | R$^3$ | R$^4$ | n | R$^5$ | R$^6$ | R$^{15}$ | Z$^2$ | R$^{16}$ |
|---|---|---|---|---|---|---|---|---|---|
| CH$_2$Cl | Me | H | H | 0 | H | H | Me | N-Pr-i | CN |
| CH$_2$Cl | Me | H | H | 0 | H | H | Me | N-Pr-i | Me |
| CH$_2$Cl | Me | H | H | 0 | H | H | Et | N-Pr-i | Cl |
| CH$_2$Cl | Me | H | H | 0 | H | H | Et | N-Pr-i | OMe |
| CH$_2$Cl | Me | H | H | 0 | H | H | Et | N-Pr-i | OCHF$_2$ |
| CH$_2$Cl | Me | H | H | 0 | H | H | Et | N-Pr-i | CN |
| CH$_2$Cl | Me | H | H | 0 | H | H | Et | N-Pr-i | Me |
| CH$_2$Cl | Me | H | H | 0 | H | H | OCHF$_2$ | N-Pr-i | Cl |
| CH$_2$Cl | Me | H | H | 2 | H | H | CF$_3$ | N-Me | Cl |

TABLE 34-continued

| R¹ | R² | R³ | R⁴ | n | R⁵ | R⁶ | R¹⁵ | Z² | R¹⁶ |
|---|---|---|---|---|---|---|---|---|---|
| CHF₂ | Me | H | H | 2 | H | H | CF₃ | N-Me | Cl |
| CHClF | Me | H | H | 2 | H | H | CF₃ | N-Me | Cl |
| CHFMe | Me | H | H | 2 | H | H | CF₃ | N-Me | Cl |
| CHClMe | Me | H | H | 2 | H | H | CF₃ | N-Me | Cl |
| CF₂Me | Me | H | H | 2 | H | H | CF₃ | N-Me | Cl |
| CH₂CH₂F | Me | H | H | 2 | H | H | CF₃ | N-Me | Cl |
| CH₂CHF₂ | Me | H | H | 2 | H | H | CF₃ | N-Me | Cl |
| CH₂CH₂Cl | Me | H | H | 2 | H | H | CF₃ | N-Me | Cl |
| CH₂CHCl₂ | Me | H | H | 2 | H | H | CF₃ | N-Me | Cl |
| CH₂CClF₂ | Me | H | H | 2 | H | H | CF₃ | N-Me | Cl |
| CH₂CF₃ | Me | H | H | 2 | H | H | CF₃ | N-Me | Cl |
| CF₂CF₃ | Me | H | H | 2 | H | H | CF₃ | N-Me | Cl |
| CH₂CH₂CF₃ | Me | H | H | 2 | H | H | CF₃ | N-Me | Cl |
| CH₂CH₂CHF₂ | Me | H | H | 2 | H | H | CF₃ | N-Me | Cl |
| CF₂CF₂CF₃ | Me | H | H | 2 | H | H | CF₃ | N-Me | Cl |
| CH₂CF₂Me | Me | H | H | 2 | H | H | CF₃ | N-Me | Cl |
| CH₂CHFMe | Me | H | H | 2 | H | H | CF₃ | N-Me | Cl |
| CF₃ | CF₃ | H | H | 2 | H | H | CF₃ | N-Me | Cl |
| CHFPr-n | Me | H | H | 2 | H | H | CF₃ | N-Me | Cl |
| CF₂Pr-n | Me | H | H | 2 | H | H | CF₃ | N-Me | Cl |
| CHCl₂ | Me | H | H | 0 | H | H | CF₃ | N-Me | Cl |
| CHF₂ | Me | H | H | 0 | H | H | CF₃ | N-Me | Cl |
| CHClF | Me | H | H | 0 | H | H | CF₃ | N-Me | Cl |
| CHFMe | Me | H | H | 0 | H | H | CF₃ | N-Me | Cl |
| CHClMe | Me | H | H | 0 | H | H | CF₃ | N-Me | Cl |
| CF₂Me | Me | H | H | 0 | H | H | CF₃ | N-Me | Cl |

TABLE 35

| 化合物番号 | R¹ | R² | R³ | R⁴ | n | R⁵ | R⁶ | R¹⁵ | Z² | R¹⁶ |
|---|---|---|---|---|---|---|---|---|---|---|
| 2-1153 | CH₂CH₂F | Me | H | H | 0 | H | H | CF₃ | N-Me | Cl |
| 2-1154 | CH₂CHF₂ | Me | H | H | 0 | H | H | CF₃ | N-Me | Cl |
| 2-1155 | CH₂CH₂Cl | Me | H | H | 0 | H | H | CF₃ | N-Me | Cl |
| 2-1156 | CH₂CHCl₂ | Me | H | H | 0 | H | H | CF₃ | N-Me | Cl |
| 2-1157 | CH₂CClF₂ | Me | H | H | 0 | H | H | CF₃ | N-Me | Cl |
| 2-1158 | CH₂CF₃ | Me | H | H | 0 | H | H | CF₃ | N-Me | Cl |
| 2-1159 | CF₂CF₃ | Me | H | H | 0 | H | H | CF₃ | N-Me | Cl |
| 2-1160 | CH₂CH₂CF₃ | Me | H | H | 0 | H | H | CF₃ | N-Me | Cl |
| 2-1161 | CH₂CH₂CHF₂ | Me | H | H | 0 | H | H | CF₃ | N-Me | Cl |
| 2-1162 | CF₂CF₂CF₃ | Me | H | H | 0 | H | H | CF₃ | N-Me | Cl |
| 2-1163 | CH₂CF₂Me | Me | H | H | 0 | H | H | CF₃ | N-Me | Cl |
| 2-1164 | CH₂CHFMe | Me | H | H | 0 | H | H | CF₃ | N-Me | Cl |
| 2-1165 | CF₃ | CF₃ | H | H | 0 | H | H | CF₃ | N-Me | Cl |
| 2-1166 | CHFPr-n | Me | H | H | 0 | H | H | CF₃ | N-Me | Cl |
| 2-1167 | CF₂Pr-n | Me | H | H | 0 | H | H | CF₃ | N-Me | Cl |

TABLE 36

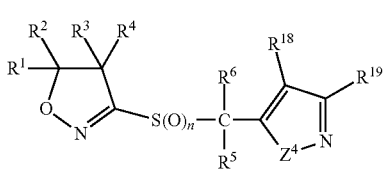

| R¹ | R² | R³ | R⁴ | n | R⁵ | R⁶ | Z⁴ | R¹⁸ | R¹⁹ |
|---|---|---|---|---|---|---|---|---|---|
| CH₂Cl | Me | H | H | 2 | H | H | N-Me | Cl | H |
| CH₂Cl | Me | H | H | 2 | H | H | N-Me | Cl | Me |
| CH₂Cl | Me | H | H | 2 | H | H | N-Me | Cl | Et |
| CH₂Cl | Me | H | H | 2 | H | H | N-Me | Cl | CF₃ |
| CH₂Cl | Me | H | H | 2 | H | H | N-Me | Cl | Me |
| CH₂Cl | Me | H | H | 2 | H | H | N-Pr-i | Cl | Me |
| CH₂Cl | Me | H | H | 2 | H | H | N-Pr | Cl | Me |
| CH₂Cl | Me | H | H | 2 | H | H | N-Bu-t | Cl | Me |
| CH₂Cl | Me | H | H | 2 | H | H | N—CH₂Ph | Cl | Me |
| CH₂Cl | Me | H | H | 2 | H | H | N-Ph | OMe | Me |
| CH₂Cl | Me | H | H | 2 | H | H | N-Ph | OEt | Me |

TABLE 36-continued

| R¹ | R² | R³ | R⁴ | n | R⁵ | R⁶ | Z⁴ | R¹⁸ | R¹⁹ |
|---|---|---|---|---|---|---|---|---|---|
| CH₂Cl | Me | H | H | 2 | H | H | N-Ph | OCHF₂ | Me |
| CH₂Cl | Me | H | H | 2 | H | H | N-Ph | OCH₂CF₃ | Me |
| CH₂Cl | Me | H | H | 2 | H | H | N-Ph | CF₃ | H |
| CH₂Cl | Me | H | H | 2 | H | H | N-Ph | OCH₂CH=CH₂ | Me |
| CH₂Cl | Me | H | H | 2 | H | H | N-Ph | OCH₂C≡CH | Me |
| CH₂Cl | Me | H | H | 2 | H | H | N-Ph | Cl | Me |
| CH₂Cl | Me | H | H | 2 | H | H | N-Ph(2-Cl) | Cl | Me |
| CH₂Cl | Me | H | H | 2 | H | H | N-Ph(2-F) | Cl | Me |
| CH₂Cl | Me | H | H | 2 | H | H | N-Ph(2-OMe) | Cl | Me |
| CH₂Cl | Me | H | H | 2 | H | H | N-Ph(2-Me) | Cl | Me |
| CH₂Cl | Me | H | H | 2 | H | H | N-Ph(3-Cl) | Cl | Me |
| CH₂Cl | Me | H | H | 2 | H | H | N-Ph(3-F) | Cl | Me |
| CH₂Cl | Me | H | H | 2 | H | H | N-Ph(3-OMe) | Cl | Me |
| CH₂Cl | Me | H | H | 2 | H | H | N-Ph(3-Me) | Cl | Me |
| CH₂Cl | Me | H | H | 2 | H | H | N-Ph(4-Cl) | Cl | Me |
| CH₂Cl | Me | H | H | 2 | H | H | N-Ph(4-F) | Cl | Me |
| CH₂Cl | Me | H | H | 2 | H | H | N-Ph(4-OMe) | Cl | Me |
| CH₂Cl | Me | H | H | 2 | H | H | N-Ph(4-Me) | Cl | Me |

TABLE 37

| R¹ | R² | R³ | R⁴ | n | R⁵ | R⁶ | Z⁴ | R¹⁸ | R¹⁹ |
|---|---|---|---|---|---|---|---|---|---|
| CH₂Br | H | H | H | 2 | H | H | N-Ph | Cl | Me |
| CH₂Cl | H | H | H | 2 | H | H | N-Ph | Cl | Me |
| CH₂Cl | H | Me | H | 2 | H | H | N-Ph | Cl | Me |
| CH₂Cl | Me | H | H | 2 | Me | H | N-Ph | Cl | Me |
| CH₂Cl | Me | H | H | 2 | Et | H | N-Ph | Cl | Me |
| CH₂Cl | Me | H | H | 2 | Pr-i | H | N-Ph | Cl | Me |
| CH₂Cl | Me | H | H | 2 | Me | Me | N-Ph | Cl | Me |
| CH₂Cl | Et | H | H | 2 | H | H | N-Ph | Cl | Me |
| CH₂Cl | CH₂Cl | H | H | 2 | H | H | N-Ph | Cl | Me |
| CH₂Cl | Pr-i | H | H | 2 | H | H | N-Ph | Cl | Me |
| CH₂Cl | Pr | H | H | 2 | H | H | N-Ph | Cl | Me |
| CH₂Cl | Pr-c | H | H | 2 | H | H | N-Ph | Cl | Me |
| CH₂Cl | CH₂Pr-c | H | H | 2 | H | H | N-Ph | Cl | Me |
| CH₂F | CH₂Cl | H | H | 2 | H | H | N-Ph | Cl | Me |
| CH₂Br | CH₂Cl | H | H | 2 | H | H | N-Ph | Cl | Me |
| CH₂I | CH₂Cl | H | H | 2 | H | H | N-Ph | Cl | Me |
| CF₃ | CH₂Cl | H | H | 2 | H | H | N-Ph | Cl | Me |
| CH₂Cl | —(CH₂)₃— | | H | 2 | H | H | N-Ph | Cl | Me |
| CH₂Cl | —(CH₂)₄— | | H | 2 | H | H | N-Ph | Cl | Me |
| CH₂Cl | —(CH₂)₅— | | H | 2 | H | H | N-Ph | Cl | Me |
| CH₂Cl | —(CH₂)₆— | | H | 2 | H | H | N-Ph | Cl | Me |
| CH₂Cl | Me | H | H | 1 | H | H | N-Ph | Cl | H |
| CH₂Cl | Me | H | H | 1 | H | H | N-Ph | Cl | Me |
| CH₂Cl | Me | H | H | 1 | H | H | N-Ph | Cl | Et |
| CH₂Cl | Me | H | H | 1 | H | H | N-Ph | Cl | CF₃ |
| CH₂Cl | Me | H | H | 1 | H | H | N-Et | Cl | Me |
| CH₂Cl | Me | H | H | 1 | H | H | N-Pr-i | Cl | Me |
| CH₂Cl | Me | H | H | 1 | H | H | N-Pr | Cl | Me |
| CH₂Cl | Me | H | H | 1 | H | H | N-Bu-t | Cl | Me |
| CH₂Cl | Me | H | H | 1 | H | H | N-CH₂Ph | Cl | Me |
| CH₂Cl | Me | H | H | 1 | H | H | N-Ph | OMe | Me |
| CH₂Cl | Me | H | H | 1 | H | H | N-Ph | OEt | Me |
| CH₂Cl | Me | H | H | 1 | H | H | N-Ph | OCHF₂ | Me |

TABLE 38

| R¹ | R² | R³ | R⁴ | n | R⁵ | R⁶ | Z⁴ | R¹⁸ | R¹⁹ |
|---|---|---|---|---|---|---|---|---|---|
| CH₂Cl | Me | H | H | 1 | H | H | N-Ph | OCH₂CF₃ | Me |
| CH₂Cl | Me | H | H | 1 | H | H | N-Ph | CF₃ | H |

TABLE 38-continued

| R¹ | R² | R³ | R⁴ | n | R⁵ | R⁶ | Z⁴ | R¹⁸ | R¹⁹ |
|---|---|---|---|---|---|---|---|---|---|
| CH₂Cl | Me | H | H | 1 | H | H | N-Ph | OCH₂CH=CH₂ | Me |
| CH₂Cl | Me | H | H | 1 | H | H | N-Ph | OCH₂C≡CH | Me |
| CH₂Cl | Me | H | H | 1 | H | H | N-Ph | Cl | Me |
| CH₂Cl | Me | H | H | 1 | H | H | N-Ph(2-Cl) | Cl | Me |
| CH₂Cl | Me | H | H | 1 | H | H | N-Ph(2-F) | Cl | Me |
| CH₂Cl | Me | H | H | 1 | H | H | N-Ph(2-OMe) | Cl | Me |
| CH₂Cl | Me | H | H | 1 | H | H | N-Ph(2-Me) | Cl | Me |
| CH₂Cl | Me | H | H | 1 | H | H | N-Ph(3-Cl) | Cl | Me |
| CH₂Cl | Me | H | H | 1 | H | H | N-Ph(3-F) | Cl | Me |
| CH₂Cl | Me | H | H | 1 | H | H | N-Ph(3-OMe) | Cl | Me |
| CH₂Cl | Me | H | H | 1 | H | H | N-Ph(3-Me) | Cl | Me |
| CH₂Cl | Me | H | H | 1 | H | H | N-Ph(4-Cl) | Cl | Me |
| CH₂Cl | Me | H | H | 1 | H | H | N-Ph(4-F) | Cl | Me |
| CH₂Cl | Me | H | H | 1 | H | H | N-Ph(4-OMe) | Cl | Me |
| CH₂Cl | Me | H | H | 1 | H | H | N-Ph(4-Me) | Cl | Me |
| CH₂Br | H | H | H | 1 | H | H | N-Ph | Cl | Me |
| CH₂Cl | H | H | H | 1 | H | H | N-Ph | Cl | Me |
| CH₂Cl | H | Me | H | 1 | H | H | N-Ph | Cl | Me |
| CH₂Cl | Me | H | H | 1 | Me | H | N-Ph | Cl | Me |
| CH₂Cl | Me | H | H | 1 | Et | H | N-Ph | Cl | Me |
| CH₂Cl | Me | H | H | 1 | Pr-i | H | N-Ph | Cl | Me |
| CH₂Cl | Me | H | H | 1 | Me | Me | N-Ph | Cl | Me |
| CH₂Cl | Et | H | H | 1 | H | H | N-Ph | Cl | Me |
| CH₂Cl | CH₂Cl | H | H | 1 | H | H | N-Ph | Cl | Me |
| CH₂Cl | Pr-i | H | H | 1 | H | H | N-Ph | Cl | Me |
| CH₂Cl | Pr | H | H | 1 | H | H | N-Ph | Cl | Me |
| CH₂Cl | Pr-c | H | H | 1 | H | H | N-Ph | Cl | Me |
| CH₂Cl | CH₂Pr-c | H | H | 1 | H | H | N-Ph | Cl | Me |
| CH₂F | CH₂Cl | H | H | 1 | H | H | N-Ph | Cl | Me |
| CH₂Br | CH₂Cl | H | H | 1 | H | H | N-Ph | Cl | Me |
| CH₂I | CH₂Cl | H | H | 1 | H | H | N-Ph | Cl | Me |

TABLE 39

| R¹ | R² | R³ | R⁴ | n | R⁵ | R⁶ | Z⁴ | R¹⁸ | R¹⁹ |
|---|---|---|---|---|---|---|---|---|---|
| CF₃ | CH₂Cl | H | H | 1 | H | H | N-Ph | Cl | Me |
| CH₂Cl | —(CH₂)₃— | | H | 1 | H | H | N-Ph | Cl | Me |
| CH₂Cl | —(CH₂)₄— | | H | 1 | H | H | N-Ph | Cl | Me |
| CH₂Cl | —(CH₂)₅— | | H | 1 | H | H | N-Ph | Cl | Me |
| CH₂Cl | —(CH₂)₆— | | H | 1 | H | H | N-Ph | Cl | Me |
| CH₂Cl | Me | H | H | 0 | H | H | N-Me | Cl | H |
| CH₂Cl | Me | H | H | 0 | H | H | N-Me | Cl | Me |
| CH₂Cl | Me | H | H | 0 | H | H | N-Me | Cl | Et |
| CH₂Cl | Me | H | H | 0 | H | H | N-Me | Cl | CF₃ |
| CH₂Cl | Me | H | H | 0 | H | H | N-Et | Cl | Me |
| CH₂Cl | Me | H | H | 0 | H | H | N-Pr-i | Cl | Me |
| CH₂Cl | Me | H | H | 0 | H | H | N-Pr | Cl | Me |
| CH₂Cl | Me | H | H | 0 | H | H | N-Bu-t | Cl | Me |
| CH₂Cl | Me | H | H | 0 | H | H | N—CH₂Ph | Cl | Me |
| CH₂Cl | Me | H | H | 0 | H | H | N-Ph | OMe | Me |
| CH₂Cl | Me | H | H | 0 | H | H | N-Ph | OEt | Me |
| CH₂Cl | Me | H | H | 0 | H | H | N-Ph | OCHF₂ | Me |
| CH₂Cl | Me | H | H | 0 | H | H | N-Ph | OCH₂CF₃ | Me |
| CH₂Cl | Me | H | H | 0 | H | H | N-Ph | CF₃ | H |
| CH₂Cl | Me | H | H | 0 | H | H | N-Ph | OCH₂CH=CH₂ | Me |
| CH₂Cl | Me | H | H | 0 | H | H | N-Ph | OCH₂C≡CH | Me |
| CH₂Cl | Me | H | H | 0 | H | H | N-Ph | Cl | Me |
| CH₂Cl | Me | H | H | 0 | H | H | N-Ph(2-Cl) | Cl | Me |
| CH₂Cl | Me | H | H | 0 | H | H | N-Ph(2-F) | Cl | Me |
| CH₂Cl | Me | H | H | 0 | H | H | N-Ph(2-OMe) | Cl | Me |
| CH₂Cl | Me | H | H | 0 | H | H | N-Ph(2-Me) | Cl | Me |
| CH₂Cl | Me | H | H | 0 | H | H | N-Ph(3-Cl) | Cl | Me |
| CH₂Cl | Me | H | H | 0 | H | H | N-Ph(3-F) | Cl | Me |
| CH₂Cl | Me | H | H | 0 | H | H | N-Ph(3-OMe) | Cl | Me |
| CH₂Cl | Me | H | H | 0 | H | H | N-Ph(3-Me) | Cl | Me |
| CH₂Cl | Me | H | H | 0 | H | H | N-Ph(4-Cl) | Cl | Me |
| CH₂Cl | Me | H | H | 0 | H | H | N-Ph(4-F) | Cl | Me |
| CH₂Cl | Me | H | H | 0 | H | H | N-Ph(4-OMe) | Cl | Me |

TABLE 40

| R¹ | R² | R³ | R⁴ | n | R⁵ | R⁶ | Z⁴ | R¹⁸ | R¹⁹ |
|---|---|---|---|---|---|---|---|---|---|
| CH₂Cl | Me | H | H | 0 | H | H | N-Ph(4-Me) | Cl | Me |
| CH₂Br | H | H | H | 0 | H | H | N-Ph | Cl | Me |
| CH₂Cl | H | H | H | 0 | H | H | N-Ph | Cl | Me |
| CH₂Cl | H | Me | H | 0 | H | H | N-Ph | Cl | Me |
| CH₂Cl | Me | H | H | 0 | Me | H | N-Ph | Cl | Me |
| CH₂Cl | Me | H | H | 0 | Et | H | N-Ph | Cl | Me |
| CH₂Cl | Me | H | H | 0 | Pr-i | H | N-Ph | Cl | Me |
| CH₂Cl | Me | H | H | 0 | Me | Me | N-Ph | Cl | Me |
| CH₂Cl | Et | H | H | 0 | H | H | N-Ph | Cl | Me |
| CH₂Cl | CH₂Cl | H | H | 0 | H | H | N-Ph | Cl | Me |
| CH₂Cl | Pr-i | H | H | 0 | H | H | N-Ph | Cl | Me |
| CH₂Cl | Pr | H | H | 0 | H | H | N-Ph | Cl | Me |
| CH₂Cl | Pr-c | H | H | 0 | H | H | N-Ph | Cl | Me |
| CH₂Cl | CH₂Pr-c | H | H | 0 | H | H | N-Ph | Cl | Me |
| CH₂F | CH₂Cl | H | H | 0 | H | H | N-Ph | Cl | Me |
| CH₂Br | CH₂Cl | H | H | 0 | H | H | N-Ph | Cl | Me |
| CH₂I | CH₂Cl | H | H | 0 | H | H | N-Ph | Cl | Me |
| CF₃ | CH₂Cl | H | H | 0 | H | H | N-Ph | Cl | Me |
| CH₂Cl | —(CH₂)₃— |  | H | 0 | H | H | N-Ph | Cl | Me |
| CH₂Cl | —(CH₂)₄— |  | H | 0 | H | H | N-Ph | Cl | Me |
| CH₂Cl | —(CH₂)₅— |  | H | 0 | H | H | N-Ph | Cl | Me |
| CH₂Cl | —(CH₂)₆— |  | H | 0 | H | H | N-Ph | Cl | Me |
| CH₂Cl | Et | H | H | 2 | H | H | N—H | H | H |
| CH₂Cl | Me | H | H | 2 | H | H | N—H | CF₃ | H |
| CH₂Cl | Me | H | H | 2 | H | H | N—CHF₂ | COMe | H |
| CH₂Cl | Me | H | H | 2 | H | H | N—CHF₂ | COMe | Me |
| CH₂Cl | Me | H | H | 2 | H | H | N—CHF₂ | COOMe | H |
| CH₂Cl | Me | H | H | 2 | H | H | N—CHF₂ | COOMe | Me |
| CH₂Cl | Me | H | H | 2 | H | H | N—CHF₂ | OCHF₂ | H |
| CH₂Cl | Me | H | H | 2 | H | H | N—CHF₂ | OCHF₂ | Me |
| CH₂Cl | Me | H | H | 2 | H | H | N—CHF₂ | OCHF₂ | Et |
| CH₂Cl | Me | H | H | 2 | H | H | N—CHF₂ | CF₃ | H |
| CH₂Cl | Me | H | H | 2 | H | H | N—CHF₂ | CF₃ | Me |

TABLE 41

| R¹ | R² | R³ | R⁴ | n | R⁵ | R⁶ | Z⁴ | R¹⁸ | R¹⁹ |
|---|---|---|---|---|---|---|---|---|---|
| CH₂Cl | Me | H | H | 2 | H | H | N—CHF₂ | CF₃ | Et |
| CH₂Cl | Me | H | H | 2 | H | H | N—CHF₂ | —(CH₂)₃— | |
| CHCl₂ | Me | H | H | 2 | H | H | N-Me | CF₃ | H |
| CHF₂ | Me | H | H | 2 | H | H | N-Me | CF₃ | H |
| CHClF | Me | H | H | 2 | H | H | N-Me | CF₃ | H |
| CHFMe | Me | H | H | 2 | H | H | N-Me | CF₃ | H |
| CHClMe | Me | H | H | 2 | H | H | N-Me | CF₃ | H |
| CF₂Me | Me | H | H | 2 | H | H | N-Me | CF₃ | H |
| CH₂CH₂F | Me | H | H | 2 | H | H | N-Me | CF₃ | H |
| CH₂CHF₂ | Me | H | H | 2 | H | H | N-Me | CF₃ | H |
| CH₂CH₂Cl | Me | H | H | 2 | H | H | N-Me | CF₃ | H |
| CH₂CHCl₂ | Me | H | H | 2 | H | H | N-Me | CF₃ | H |
| CH₂CClF₂ | Me | H | H | 2 | H | H | N-Me | CF₃ | H |
| CH₂CF₃ | Me | H | H | 2 | H | H | N-Me | CF₃ | H |
| CF₂CF₃ | Me | H | H | 2 | H | H | N-Me | CF₃ | H |
| CH₂CH₂CF₃ | Me | H | H | 2 | H | H | N-Me | CF₃ | H |
| CH₂CH₂CHF₂ | Me | H | H | 2 | H | H | N-Me | CF₃ | H |
| CF₂CF₂CF₃ | Me | H | H | 2 | H | H | N-Me | CF₃ | H |
| CH₂CF₂Me | Me | H | H | 2 | H | H | N-Me | CF₃ | H |
| CH₂CHFMe | Me | H | H | 2 | H | H | N-Me | CF₃ | H |
| CF₃ | CF₃ | H | H | 2 | H | H | N-Me | CF₃ | H |
| CHFPr-n | Me | H | H | 2 | H | H | N-Me | CF₃ | H |
| CF₂Pr-n | Me | H | H | 2 | H | H | N-Me | CF₃ | H |

TABLE 42

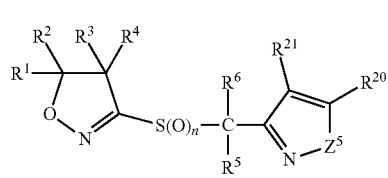

| R¹ | R² | R³ | R⁴ | n | R⁵ | R⁶ | Z⁵ | R²⁰ | R²¹ |
|---|---|---|---|---|---|---|---|---|---|
| CH₂Cl | Me | H | H | 2 | H | H | N-Me | H | OMe |
| CH₂Cl | Me | H | H | 2 | H | H | N-Me | H | OEt |
| CH₂Cl | Me | H | H | 2 | H | H | N-Me | H | OCHF₂ |
| CH₂Cl | Me | H | H | 2 | H | H | N-Me | H | OCH₂CF₃ |
| CH₂Cl | Me | H | H | 2 | H | H | N-Ph | H | OMe |
| CH₂Cl | Me | H | H | 2 | H | H | N-Ph | H | OEt |
| CH₂Cl | Me | H | H | 2 | H | H | N-Ph | H | OCHF₂ |
| CH₂Cl | Me | H | H | 2 | H | H | N-Ph | H | OCH₂CF₃ |
| CH₂Cl | Me | H | H | 2 | H | H | S | Me | H |
| CH₂Cl | CH₂Cl | H | H | 2 | H | H | N-Ph | H | OMe |
| CH₂Cl | H | H | H | 2 | H | H | N-Ph | H | OEt |
| CH₂Cl | H | Me | H | 2 | H | H | N-Ph | H | OMe |
| CH₂Cl | Me | H | H | 2 | Me | H | N-Ph | H | OEt |
| CH₂Cl | Me | H | H | 2 | Et | H | N-Ph | H | OMe |
| CH₂Cl | Me | H | H | 2 | Pr-i | H | N-Ph | H | OEt |
| CH₂Cl | Me | H | H | 2 | Me | Me | N-Ph | H | OMe |
| CH₂Cl | Et | H | H | 2 | H | H | N-Ph | H | OEt |
| CH₂Cl | CH₂Br | H | H | 2 | H | H | N-Ph | H | OMe |
| CH₂Cl | Pr-i | H | H | 2 | H | H | N-Ph | H | OEt |
| CH₂Cl | Pr | H | H | 2 | H | H | N-Ph | H | OMe |
| CH₂Cl | Pr-c | H | H | 2 | H | H | N-Ph | H | OEt |
| CH₂Cl | CH₂Pr-c | H | H | 2 | H | H | N-Ph | H | OMe |
| CH₂Br | Me | H | H | 2 | H | H | N-Ph | H | OEt |
| CH₂F | Me | H | H | 2 | H | H | N-Ph | H | OMe |
| CH₂I | Me | H | H | 2 | H | H | N-Ph | H | OEt |
| CF₃ | Me | H | H | 2 | H | H | N-Ph | H | OMe |

TABLE 42-continued

Structure: R¹R²R³R⁴-isoxazoline-S(O)n-C(R⁵)(R⁶)-pyrazole(R²⁰,R²¹,Z⁵)

| R¹ | R² | R³ | R⁴ | n | R⁵ | R⁶ | Z⁵ | R²⁰ | R²¹ |
|---|---|---|---|---|---|---|---|---|---|
| CH₂Cl | —(CH₂)₃— | | H | 2 | H | H | N-Ph | H | OEt |
| CH₂Cl | —(CH₂)₄— | | H | 2 | H | H | N-Ph | H | OMe |
| CH₂Cl | —(CH₂)₅— | | H | 2 | H | H | N-Ph | H | OMe |
| CH₂Cl | —(CH₂)₆— | | H | 2 | H | H | N-Ph | H | OEt |
| CH₂Cl | Me | H | H | 1 | H | H | N-Me | H | OMe |

TABLE 43

| R¹ | R² | R³ | R⁴ | n | R⁵ | R⁶ | Z⁵ | R²⁰ | R²¹ |
|---|---|---|---|---|---|---|---|---|---|
| CH₂Cl | Me | H | H | 1 | H | H | N-Me | H | OEt |
| CH₂Cl | Me | H | H | 1 | H | H | N-Me | H | OCHF₂ |
| CH₂Cl | Me | H | H | 1 | H | H | N-Me | H | OCH₂CF₃ |
| CH₂Cl | Me | H | H | 1 | H | H | N-Ph | H | OMe |
| CH₂Cl | Me | H | H | 1 | H | H | N-Ph | H | OEt |
| CH₂Cl | Me | H | H | 1 | H | H | N-Ph | H | OCHF₂ |
| CH₂Cl | Me | H | H | 1 | H | H | N-Ph | H | OCH₂CF₃ |
| CH₂Cl | Me | H | H | 1 | H | H | S | Me | H |
| CH₂Cl | CH₂Cl | H | H | 1 | H | H | N-Ph | H | OMe |
| CH₂Cl | H | H | H | 1 | H | H | N-Ph | H | OEt |
| CH₂Cl | H | Me | H | 1 | H | H | N-Ph | H | OMe |
| CH₂Cl | Me | H | H | 1 | Me | H | N-Ph | H | OEt |
| CH₂Cl | Me | H | H | 1 | Et | H | N-Ph | H | OMe |
| CH₂Cl | Me | H | H | 1 | Pr-i | H | N-Ph | H | OEt |
| CH₂Cl | Me | H | H | 1 | Me | Me | N-Ph | H | OMe |
| CH₂Cl | Et | H | H | 1 | H | H | N-Ph | H | OEt |
| CH₂Cl | CH₂Br | H | H | 1 | H | H | N-Ph | H | OMe |
| CH₂Cl | Pr-i | H | H | 1 | H | H | N-Ph | H | OEt |
| CH₂Cl | Pr | H | H | 1 | H | H | N-Ph | H | OMe |
| CH₂Cl | Pr-c | H | H | 1 | H | H | N-Ph | H | OEt |
| CH₂Cl | CH₂Pr-c | H | H | 1 | H | H | N-Ph | H | OMe |
| CH₂Br | Me | H | H | 1 | H | H | N-Ph | H | OEt |
| CH₂F | Me | H | H | 1 | H | H | N-Ph | H | OMe |
| CH₂I | Me | H | H | 1 | H | H | N-Ph | H | OEt |
| CF₃ | Me | H | H | 1 | H | H | N-Ph | H | OMe |
| CH₂Cl | —(CH₂)₃— | | H | 1 | H | H | N-Ph | H | OEt |
| CH₂Cl | —(CH₂)₄— | | H | 1 | H | H | N-Ph | H | OMe |
| CH₂Cl | —(CH₂)₅— | | H | 1 | H | H | N-Ph | H | OMe |
| CH₂Cl | —(CH₂)₆— | | H | 1 | H | H | N-Ph | H | OEt |
| CH₂Cl | Me | H | H | 0 | H | H | N-Me | H | OMe |
| CH₂Cl | Me | H | H | 0 | H | H | N-Me | H | OEt |
| CH₂Cl | Me | H | H | 0 | H | H | N-Me | H | OCHF₂ |
| CH₂Cl | Me | H | H | 0 | H | H | N-Me | H | OCH₂CF₃ |
| CH₂Cl | Me | H | H | 0 | H | H | N-Ph | H | OMe |

TABLE 44

| R¹ | R² | R³ | R⁴ | n | R⁵ | R⁶ | Z⁵ | R²⁰ | R²¹ |
|---|---|---|---|---|---|---|---|---|---|
| CH₂Cl | Me | H | H | 0 | H | H | N-Ph | H | OEt |
| CH₂Cl | Me | H | H | 0 | H | H | N-Ph | H | OCHF₂ |
| CH₂Cl | Me | H | H | 0 | H | H | N-Ph | H | OCH₂CF₃ |
| CH₂Cl | Me | H | H | 0 | H | H | S | Me | H |
| CH₂Cl | CH₂Cl | H | H | 0 | H | H | N-Ph | H | OMe |
| CH₂Cl | H | H | H | 0 | H | H | N-Ph | H | OEt |
| CH₂Cl | H | Me | H | 0 | H | H | N-Ph | H | OMe |
| CH₂Cl | Me | H | H | 0 | Me | H | N-Ph | H | OEt |
| CH₂Cl | Me | H | H | 0 | Et | H | N-Ph | H | OMe |
| CH₂Cl | Me | H | H | 0 | Pr-i | H | N-Ph | H | OEt |
| CH₂Cl | Me | H | H | 0 | Me | Me | N-Ph | H | OMe |
| CH₂Cl | Et | H | H | 0 | H | H | N-Ph | H | OEt |
| CH₂Cl | CH₂Br | H | H | 0 | H | H | N-Ph | H | OMe |
| CH₂Cl | Pr-i | H | H | 0 | H | H | N-Ph | H | OEt |
| CH₂Cl | Pr | H | H | 0 | H | H | N-Ph | H | OMe |
| CH₂Cl | Pr-c | H | H | 0 | H | H | N-Ph | H | OEt |
| CH₂Cl | CH₂Pr-c | H | H | 0 | H | H | N-Ph | H | OMe |
| CH₂Br | Me | H | H | 0 | H | H | N-Ph | H | OEt |
| CH₂F | Me | H | H | 0 | H | H | N-Ph | H | OMe |
| CH₂I | Me | H | H | 0 | H | H | N-Ph | H | OEt |
| CF₃ | Me | H | H | 0 | H | H | N-Ph | H | OMe |
| CH₂Cl | —(CH₂)₃— | | H | 0 | H | H | N-Ph | H | OEt |
| CH₂Cl | —(CH₂)₄— | | H | 0 | H | H | N-Ph | H | OMe |
| CH₂Cl | —(CH₂)₅— | | H | 0 | H | H | N-Ph | H | OMe |
| CH₂Cl | —(CH₂)₆— | | H | 0 | H | H | N-Ph | H | OEt |
| CH₂Cl | Et | H | H | 2 | H | H | S | H | H |
| CH₂Cl | Et | H | H | 2 | H | H | N—H | H | H |
| CH₂Cl | Me | H | H | 2 | H | H | N-Me | Cl | CHF₂ |
| CH₂Cl | Me | H | H | 2 | H | H | N-Me | Cl | CF₃ |
| CH₂Cl | Me | H | H | 2 | H | H | N-Me | Cl | CF₃ |
| CHF₂ | Me | H | H | 2 | H | H | N-Me | Cl | CF₃ |
| CHClF | Me | H | H | 2 | H | H | N-Me | Cl | CF₃ |
| CHFMe | Me | H | H | 2 | H | H | N-Me | Cl | CF₃ |

TABLE 45

| R¹ | R² | R³ | R⁴ | n | R⁵ | R⁶ | Z⁵ | R²⁰ | R²¹ |
|---|---|---|---|---|---|---|---|---|---|
| CHClMe | Me | H | H | 2 | H | H | N-Me | Cl | CF₃ |
| CF₂Me | Me | H | H | 2 | H | H | N-Me | Cl | CF₃ |
| CH₂CH₂F | Me | H | H | 2 | H | H | N-Me | Cl | CF₃ |
| CH₂CHF₂ | Me | H | H | 2 | H | H | N-Me | Cl | CF₃ |
| CH₂CH₂Cl | Me | H | H | 2 | H | H | N-Me | Cl | CF₃ |
| CH₂CHCl₂ | Me | H | H | 2 | H | H | N-Me | Cl | CF₃ |
| CH₂CClF₂ | Me | H | H | 2 | H | H | N-Me | Cl | CF₃ |
| CH₂CF₃ | Me | H | H | 2 | H | H | N-Me | Cl | CF₃ |
| CF₂CF₃ | Me | H | H | 2 | H | H | N-Me | Cl | CF₃ |
| CH₂CH₂CF₃ | Me | H | H | 2 | H | H | N-Me | Cl | CF₃ |
| CH₂CH₂CHF₂ | Me | H | H | 2 | H | H | N-Me | Cl | CF₃ |
| CF₂CF₂CF₃ | Me | H | H | 2 | H | H | N-Me | Cl | CF₃ |
| CH₂CF₂Me | Me | H | H | 2 | H | H | N-Me | Cl | CF₃ |
| CH₂CHFMe | Me | H | H | 2 | H | H | N-Me | Cl | CF₃ |
| CF₃ | CF₃ | H | H | 2 | H | H | N-Me | Cl | CF₃ |
| CHFPr-n | Me | H | H | 2 | H | H | N-Me | Cl | CF₃ |
| CF₂Pr-n | Me | H | H | 2 | H | H | N-Me | Cl | CF₃ |
| CH₂Cl | Me | H | H | 0 | H | H | N-Me | Cl | CHF₂ |
| CH₂Cl | Me | H | H | 0 | H | H | N-Me | Cl | CF₃ |
| CHCl₂ | Me | H | H | 0 | H | H | N-Me | Cl | CF₃ |
| CHF₂ | Me | H | H | 0 | H | H | N-Me | Cl | CF₃ |
| CHClF | Me | H | H | 0 | H | H | N-Me | Cl | CF₃ |
| CHFMe | Me | H | H | 0 | H | H | N-Me | Cl | CF₃ |
| CHClMe | Me | H | H | 0 | H | H | N-Me | Cl | CF₃ |
| CF₂Me | Me | H | H | 0 | H | H | N-Me | Cl | CF₃ |
| CH₂CH₂F | Me | H | H | 0 | H | H | N-Me | Cl | CF₃ |
| CH₂CHF₂ | Me | H | H | 0 | H | H | N-Me | Cl | CF₃ |
| CH₂CH₂Cl | Me | H | H | 0 | H | H | N-Me | Cl | CF₃ |
| CH₂CHCl₂ | Me | H | H | 0 | H | H | N-Me | Cl | CF₃ |
| CH₂CClF₂ | Me | H | H | 0 | H | H | N-Me | Cl | CF₃ |
| CH₂CF₃ | Me | H | H | 0 | H | H | N-Me | Cl | CF₃ |
| CF₂CF₃ | Me | H | H | 0 | H | H | N-Me | Cl | CF₃ |
| CH₂CH₂CF₃ | Me | H | H | 0 | H | H | N-Me | Cl | CF₃ |

TABLE 46

| R¹ | R² | R³ | R⁴ | n | R⁵ | R⁶ | Z⁵ | R²⁰ | R²¹ |
|---|---|---|---|---|---|---|---|---|---|
| CH₂CH₂CHF₂ | Me | H | H | 0 | H | H | N-Me | Cl | CF₃ |
| CF₂CF₂CF₃ | Me | H | H | 0 | H | H | N-Me | Cl | CF₃ |
| CH₂CF₂Me | Me | H | H | 0 | H | H | N-Me | Cl | CF₃ |
| CH₂CHFMe | Me | H | H | 0 | H | H | N-Me | Cl | CF₃ |
| CF₃ | CF₃ | H | H | 0 | H | H | N-Me | Cl | CF₃ |
| CHFPr-n | Me | H | H | 0 | H | H | N-Me | Cl | CF₃ |
| CF₂Pr-n | Me | H | H | 0 | H | H | N-Me | Cl | CF₃ |

TABLE 47

| R¹ | R² | R³ | R⁴ | n | R⁵ | R⁶ | Y¹ |
|---|---|---|---|---|---|---|---|
| CH₂Cl | Me | H | H | 2 | H | H | 1,2,4-Oxadiazol-3-yl |
| CH₂Cl | Me | H | H | 2 | H | H | 3-Phenyl-1,2,4-oxadiazol-5-yl |
| CH₂Cl | Me | H | H | 2 | H | H | 3-Benzyl-1,2,4-oxadiazol-5-yl |
| CH₂Cl | Me | H | H | 2 | Pr-i | H | 4-Trifluoromethylpyrimidin-5-yl |
| CH₂Cl | Me | H | H | 2 | H | H | 4,6-Dimetoxypyrimidin-2-yl |
| CH₂Cl | Me | H | H | 2 | H | H | 4,6-Dichloropyrimidin-5-yl |
| CH₂Cl | Me | H | H | 2 | H | H | 1,4-Dimethylimidazol-5-yl |
| CH₂Cl | Me | H | H | 2 | H | H | 1-Phenyl-4-methoxycarbonyl-1,2,3-triazol-5-yl |
| CH₂Cl | Me | H | H | 2 | H | H | 4-Methyl-6-trifluoromethylpyrimidin-5-yl |
| CH₂Cl | Me | H | H | 2 | H | H | 4-Chloro-6-trifluoromethylpyrimidin-5-yl |
| CH₂Cl | Me | H | H | 2 | H | H | 4-Methoxy-6-trifluoromethylpyrimidin-5-yl |
| CH₂Cl | Me | H | H | 2 | H | H | 4-Ethoxy-6-trifluoromethylpyrimidin-5-yl |
| CH₂Cl | Me | H | H | 2 | H | H | 4-Phenoxy-6-trifluoromethylpyrimidin-5-yl |
| CH₂Cl | Me | H | H | 2 | H | H | 4-Phenyl-6-trifluoromethylpyrimidin-5-yl |
| CH₂Cl | Me | H | H | 2 | H | H | 4-Chloro-6-methylpyrimidin-5-yl |
| CH₂Cl | Me | H | H | 2 | H | H | 4-Chloro-6-methoxypyrimidin-5-yl |
| CH₂Cl | Me | H | H | 2 | H | H | 4,6-Dimethoxypyrimidin-5-yl |
| CH₂Cl | Me | H | H | 2 | H | H | 4,6-Diethoxypyrimidin-5-yl |
| CH₂Cl | Me | H | H | 2 | H | H | 4,6-Dimethoxypyrimidin-2-yl |
| CH₂Cl | Me | H | H | 2 | H | H | 4,6-Diethoxypyrimidin-2-yl |
| CH₂Cl | H | H | H | 2 | H | H | 4-Methoxy-6-trifluoromethylpyrimidin-5-yl |
| CH₂Cl | H | H | H | 2 | H | H | 4-Ethoxy-6-trifluoromethylpyrimidin-5-yl |
| CH₂Cl | H | Me | H | 2 | H | H | 4-Methoxy-6-trifluoromethylpyrimidin-5-yl |
| CH₂Cl | Me | H | H | 2 | Me | H | 4-Ethoxy-6-trifluoromethylpyrimidin-5-yl |
| CH₂Cl | Me | H | H | 2 | Et | H | 4-Methoxy-6-trifluoromethylpyrimidin-5-yl |
| CH₂Cl | Me | H | H | 2 | Pr-i | H | 4-Ethoxy-6-trifluoromethylpyrimidin-5-yl |
| CH₂Cl | Me | H | H | 2 | Me | Me | 4-Methoxy-6-trifluoromethylpyrimidin-5-yl |
| CH₂Cl | Et | H | H | 2 | H | H | 4-Ethoxy-6-trifluoromethylpyrimidin-5-yl |
| CH₂Cl | Et | H | H | 2 | H | H | 4-Methoxy-6-trifluoromethylpyrimidin-5-yl |
| CH₂Cl | Pr-i | H | H | 2 | H | H | 4-Ethoxy-6-trifluoromethylpyrimidin-5-yl |

TABLE 48

| R¹ | R² | R³ | R⁴ | n | R⁵ | R⁶ | Y¹ |
|---|---|---|---|---|---|---|---|
| CH₂Cl | Pr | H | H | 2 | H | H | 4-Methoxy-6-trifluoromethylpyrimidin-5-yl |
| CH₂Cl | Pr-c | H | H | 2 | H | H | 4-Ethoxy-6-trifluoromethylpyrimidin-5-yl |
| CH₂Cl | CH₂Pr-c | H | H | 2 | H | H | 4-Methoxy-6-trifluoromethylpyrimidin-5-yl |
| CH₂Br | Me | H | H | 2 | H | H | 4-Ethoxy-6-trifluoromethylpyrimidin-5-yl |
| CH₂F | Me | H | H | 2 | H | H | 4-Methoxy-6-trifluoromethylpyrimidin-5-yl |
| CH₂I | Me | H | H | 2 | H | H | 4-Ethoxy-6-trifluoromethylpyrimidin-5-yl |
| CF₃ | Me | H | H | 2 | H | H | 4-Methoxy-6-trifluoromethylpyrimidin-5-yl |
| CH₂Cl | —(CH₂)₃— | | H | 2 | H | H | 4-Ethoxy-6-trifluoromethylpyrimidin-5-yl |
| CH₂Cl | —(CH₂)₄— | | H | 2 | H | H | 4-Methoxy-6-trifluoromethylpyrimidin-5-yl |
| CH₂Cl | —(CH₂)₅— | | H | 2 | H | H | 4-Ethoxy-6-trifluoromethylpyrimidin-5-yl |
| CH₂Cl | —(CH₂)₆— | | H | 2 | H | H | 4-Methoxy-6-trifluoromethylpyrimidin-5-yl |
| CH₂Cl | Me | H | H | 1 | H | H | Pyridin-2-yl |
| CH₂Cl | Me | H | H | 1 | H | H | 1,2,4-Oxadiazol-3-yl |
| CH₂Cl | Me | H | H | 1 | H | H | 3-Phenyl-1,2,4-oxadiazol-5-yl |
| CH₂Cl | Me | H | H | 1 | H | H | 3-Benzyl-1,2,4-oxadiazol-5-yl |
| CH₂Cl | Me | H | H | 1 | Pr-i | H | 4-Trifluoromethylpyrimidin-5-yl |
| CH₂Cl | Me | H | H | 1 | H | H | 4,6-Dichloropyrimidin-5-yl |
| CH₂Cl | Me | H | H | 1 | H | H | 1,4-Dimethylimidazol-5-yl |
| CH₂Cl | Me | H | H | 1 | H | H | 1-Phenyl-4-methoxycarbonyl-1,2,3-triazol-5-yl |
| CH₂Cl | Me | H | H | 1 | H | H | 4-Methyl-6-trifluoromethylpyrimidin-5-yl |
| CH₂Cl | Me | H | H | 1 | H | H | 4-Chloro-6-trifluoromethylpyrimidin-5-yl |
| CH₂Cl | Me | H | H | 1 | H | H | 4-Methoxy-6-trifluoromethylpyrimidin-5-yl |
| CH₂Cl | Me | H | H | 1 | H | H | 4-Ethoxy-6-trifluoromethylpyrimidin-5-yl |
| CH₂Cl | Me | H | H | 1 | H | H | 4-Phenoxy-6-trifluoromethylpyrimidin-5-yl |
| CH₂Cl | Me | H | H | 1 | H | H | 4-Phenyl-6-trifluoromethylpyrimidin-5-yl |
| CH₂Cl | Me | H | H | 1 | H | H | 4-Chloro-6-methylpyrimidin-5-yl |
| CH₂Cl | Me | H | H | 1 | H | H | 4-Chloro-6-methoxyrimidin-5-yl |
| CH₂Cl | Me | H | H | 1 | H | H | 4,6-Dimethoxypyrimidin-5-yl |
| CH₂Cl | Me | H | H | 1 | H | H | 4,6-Diethoxypyrimidin-5-yl |
| CH₂Cl | Me | H | H | 1 | H | H | 4,6-Dimethoxypyrimidin-2-yl |

TABLE 48-continued

| R¹ | R² | R³ | R⁴ | n | R⁵ | R⁶ | Y¹ |
|---|---|---|---|---|---|---|---|
| CH₂Cl | Me | H | H | 1 | H | H | 4,6-Diethoxypyrimidin-2-yl |
| CH₂Cl | H | H | H | 1 | H | H | 4-Methoxy-6-trifluoromethylpyrimidin-5-yl |
| CH₂Cl | H | H | H | 1 | H | H | 4-Ethoxy-6-trifluoromethylpyrimidin-5-yl |
| CH₂Cl | H | Me | H | 1 | H | H | 4-Methoxy-6-trifluoromethylpyrimidin-5-yl |

TABLE 49

| R¹ | R² | R³ | R⁴ | n | R⁵ | R⁶ | Y¹ |
|---|---|---|---|---|---|---|---|
| CH₂Cl | Me | H | H | 1 | Me | H | 4-Ethoxy-6-trifluoromethylpyrimidin-5-yl |
| CH₂Cl | Me | H | H | 1 | Et | H | 4-Methoxy-6-trifluoromethylpyrimidin-5-yl |
| CH₂Cl | Me | H | H | 1 | Pr-i | H | 4-Ethoxy-6-trifluoromethylpyrimidin-5-yl |
| CH₂Cl | Me | H | H | 1 | Me | Me | 4-Methoxy-6-trifluoromethylpyrimidin-5-yl |
| CH₂Cl | Et | H | H | 1 | H | H | 4-Ethoxy-6-trifluoromethylpyrimidin-5-yl |
| CH₂Cl | Et | H | H | 1 | H | H | 4-Methoxy-6-trifluoromethylpyrimidin-5-yl |
| CH₂Cl | Pr-i | H | H | 1 | H | H | 4-Ethoxy-6-trifluoromethylpyrimidin-5-yl |
| CH₂Cl | Pr | H | H | 1 | H | H | 4-Methoxy-6-trifluoromethylpyrimidin-5-yl |
| CH₂Cl | Pr-c | H | H | 1 | H | H | 4-Ethoxy-6-trifluoromethylpyrimidin-5-yl |
| CH₂Cl | CH₂Pr-c | H | H | 1 | H | H | 4-Methoxy-6-trifluoromethylpyrimidin-5-yl |
| CH₂Br | Me | H | H | 1 | H | H | 4-Ethoxy-6-trifluoromethylpyrimidin-5-yl |
| CH₂F | Me | H | H | 1 | H | H | 4-Methoxy-6-trifluoromethylpyrimidin-5-yl |
| CH₂I | Me | H | H | 1 | H | H | 4-Ethoxy-6-trifluoromethylpyrimidin-5-yl |
| CF₃ | Me | H | H | 1 | H | H | 4-Methoxy-6-trifluoromethylpyrimidin-5-yl |
| CH₂Cl | —(CH₂)₃— | | H | 1 | H | H | 4-Ethoxy-6-trifluoromethylpyrimidin-5-yl |
| CH₂Cl | —(CH₂)₄— | | H | 1 | H | H | 4-Methoxy-6-trifluoromethylpyrimidin-5-yl |
| CH₂Cl | —(CH₂)₅— | | H | 1 | H | H | 4-Ethoxy-6-trifluoromethylpyrimidin-5-yl |
| CH₂Cl | —(CH₂)₆— | | H | 1 | H | H | 4-Methoxy-6-trifluoromethylpyrimidin-5-yl |
| CH₂Cl | Me | H | H | 0 | H | H | 1,2,4-Oxadiazol-3-yl |
| CH₂Cl | Me | H | H | 0 | H | H | 3-Phenyl-1,2,4-oxadiazol-5-yl |
| CH₂Cl | Me | H | H | 0 | H | H | 3-Benzyl-1,2,4-oxadiazol-5-yl |
| CH₂Cl | Me | H | H | 0 | Pr-i | H | 4-Trifluoromethylpyrimidin-5-yl |
| CH₂Cl | Me | H | H | 0 | H | H | 4,6-Dichloropyrimidin-5-yl |
| CH₂Cl | Me | H | H | 0 | H | H | 2,4-Diphenylpyridin-3-yl |
| CH₂Cl | Me | H | H | 0 | H | H | 1,4-Dimethylimidazol-5-yl |
| CH₂Cl | Me | H | H | 0 | H | H | 1-Phenyl-4-methoxycarbonyl-1,2,3-triazol-5-yl |
| CH₂Cl | Me | H | H | 0 | H | H | 4-Methyl-6-trifluoromethylpyrimidin-5-yl |
| CH₂Cl | Me | H | H | 0 | H | H | 4-Chloro-6-trifluoromethylpyrimidin-5-yl |
| CH₂Cl | Me | H | H | 0 | H | H | 4-Methoxy-6-trifluoromethylpyrimidin-5-yl |
| CH₂Cl | Me | H | H | 0 | H | H | 4-Ethoxy-6-trifluoromethylpyrimidin-5-yl |
| CH₂Cl | Me | H | H | 0 | H | H | 4-Phenoxy-6-trifluoromethylpyrimidin-5-yl |

TABLE 50

| R¹ | R² | R³ | R⁴ | n | R⁵ | R⁶ | Y¹ |
|---|---|---|---|---|---|---|---|
| CH₂Cl | Me | H | H | 0 | H | H | 4-Phenyl-6-trifluoromethylpyrimidin-5-yl |
| CH₂Cl | Me | H | H | 0 | H | H | 4-Chloro-6-methylpyrimidin-5-yl |
| CH₂Cl | Me | H | H | 0 | H | H | 4-Chloro-6-methoxypyrimidin-5-yl |
| CH₂Cl | Me | H | H | 0 | H | H | 4,6-Dimethoxypyrimidin-5-yl |
| CH₂Cl | Me | H | H | 0 | H | H | 4,6-Diethoxypyrimidin-5-yl |
| CH₂Cl | Me | H | H | 0 | H | H | 4,6-Dimethoxypyrimidin-2-yl |
| CH₂Cl | Me | H | H | 0 | H | H | 4,6-Diethoxypyrimidin-2-yl |
| CH₂Cl | H | H | H | 0 | H | H | 4-Methoxy-6-trifluoromethylpyrimidin-5-yl |
| CH₂Cl | H | H | H | 0 | H | H | 4-Ethoxy-6-trifluoromethylpyrimidin-5-yl |
| CH₂Cl | H | Me | H | 0 | H | H | 4-Methoxy-6-trifluoromethylpyrimidin-5-yl |
| CH₂Cl | Me | H | H | 0 | Me | H | 4-Ethoxy-6-trifluoromethylpyrimidin-5-yl |
| CH₂Cl | Me | H | H | 0 | Et | H | 4-Methoxy-6-trifluoromethylpyrimidin-5-yl |
| CH₂Cl | Me | H | H | 0 | Pr-i | H | 4-Ethoxy-6-trifluoromethylpyrimidin-5-yl |
| CH₂Cl | Me | H | H | 0 | Me | Me | 4-Methoxy-6-trifluoromethylpyrimidin-5-yl |
| CH₂Cl | Et | H | H | 0 | H | H | 4-Ethoxy-6-trifluoromethylpyrimidin-5-yl |
| CH₂Cl | Et | H | H | 0 | H | H | 4-Methoxy-6-trifluoromethylpyrimidin-5-yl |
| CH₂Cl | Pr-i | H | H | 0 | H | H | 4-Ethoxy-6-trifluoromethylpyrimidin-5-yl |
| CH₂Cl | Pr | H | H | 0 | H | H | 4-Methoxy-6-trifluoromethylpyrimidin-5-yl |
| CH₂Cl | Pr-c | H | H | 0 | H | H | 4-Ethoxy-6-trifluoromethylpyrimidin-5-yl |
| CH₂Cl | CH₂Pr-c | H | H | 0 | H | H | 4-Methoxy-6-trifluoromethylpyrimidin-5-yl |
| CH₂Br | Me | H | H | 0 | H | H | 4-Ethoxy-6-trifluoromethylpyrimidin-5-yl |
| CH₂F | Me | H | H | 0 | H | H | 4-Methoxy-6-trifluoromethylpyrimidin-5-yl |
| CH₂I | Me | H | H | 0 | H | H | 4-Ethoxy-6-trifluoromethylpyrimidin-5-yl |
| CF₃ | Me | H | H | 0 | H | H | 4-Methoxy-6-trifluoromethylpyrimidin-5-yl |
| CH₂Cl | —(CH₂)₃— | | H | 0 | H | H | 4-Ethoxy-6-trifluoromethylpyrimidin-5-yl |
| CH₂Cl | —(CH₂)₄— | | H | 0 | H | H | 4-Methoxy-6-trifluoromethylpyrimidin-5-yl |
| CH₂Cl | —(CH₂)₅— | | H | 0 | H | H | 4-Ethoxy-6-trifluoromethylpyrimidin-5-yl |

TABLE 50-continued

| R¹ | R² | R³ | R⁴ | n | R⁵ | R⁶ | Y¹ |
|---|---|---|---|---|---|---|---|
| CH₂Cl | —(CH₂)₆— | | H | 0 | H | H | 4-Methoxy-6-trifluoromethylpyrimidin-5-yl |
| CH₂Cl | CH₂Cl | H | H | 2 | H | H | Pyrrol-1-yl |
| CH₂Cl | CH₂Cl | H | H | 2 | H | H | Oxazol-2-yl |
| CH₂Cl | CH₂Br | H | H | 2 | H | H | 1H-Imidazol-2-yl |
| CH₂Cl | CF₃ | H | H | 2 | H | H | 1H-Imidazol-4-yl |
| CH₂Cl | CH₂Cl | H | H | 2 | H | H | 1H-Imidazol-5-yl |
| CH₂Cl | CH₂Cl | H | H | 2 | H | H | 1H-1,3,4-Triazol-2-yl |

TABLE 51

| R¹ | R² | R³ | R⁴ | n | R⁵ | R⁶ | Y¹ |
|---|---|---|---|---|---|---|---|
| CH₂Cl | CH₂Cl | H | H | 2 | H | H | 1H-1,3,4-Triazol-5-yl |
| CH₂Cl | Me | H | H | 2 | H | H | 4-iso-Propoxy-6-trifluoromethylpyrimidin-5-yl |
| CH₂Cl | Me | H | H | 2 | H | H | 4-Difluoromethoxy-6-trifluoromethylpyrimidin-5-yl |
| CH₂Cl | Me | H | H | 2 | H | H | 4-Methoxy-2-methyl-6-trifluoromethylpyrimidin-5-yl |
| CH₂Cl | Me | H | H | 2 | H | H | 4-Ethoxy-2-methyl-6-trifluoromethylpyrimidin-5-yl |
| CH₂Cl | Me | H | H | 2 | H | H | 2,4-Dimethoxy-6-trifluoromethylpyrimidin-5-yl |
| CH₂Cl | Me | H | H | 2 | H | H | 2,4-Ethoxy-6-trifluoromethylpyrimidin-5-yl |
| CH₂Cl | Me | H | H | 2 | H | H | 2-Amino-4-methoxy-6-trifluoromethylpyrimidin-5-yl |
| CH₂Cl | Me | H | H | 2 | H | H | 2-Amino-4-ethoxy-6-trifluoromethylpyrimidin-5-yl |
| CH₂Cl | Me | H | H | 2 | H | H | 4-Methoxy-2-methylthio-6-trifluoromethylpyrimidin-5-yl |
| CH₂Cl | Me | H | H | 2 | H | H | 4-Ethoxy-2-methylthio-6-trifluoromethylpyrimidin-5-yl |
| CH₂Cl | Me | H | H | 2 | H | H | 4-Methoxy-2-methylsulfonyl-6-trifluoromethylpyrimidin-5-yl |
| CH₂Cl | Me | H | H | 2 | H | H | 4-Ethoxy-2-methylsulfonyl-6-trifluoromethylpyrimidin-5-yl |
| CH₂Cl | Me | H | H | 2 | H | H | 2-Difluoromethoxy-4-methoxy-6-trifluoromethylpyrimidin-5-yl |
| CH₂Cl | Me | H | H | 2 | H | H | 2-Difluoromethoxy-4-ethoxy-6-trifluoromethylpyrimidin-5-yl |
| CH₂Cl | Me | H | H | 2 | H | H | 2-Cyano-4-methoxy-6-trifluoromethylpyrimidin-5-yl |
| CH₂Cl | Me | H | H | 2 | H | H | 2-Cyano-4-ethoxy-6-trifluoromethylpyrimidin-5-yl |
| CH₂Cl | Me | H | H | 2 | H | H | 4-Methoxy-2-methylamino-6-trifluoromethylpyrimidin-5-yl |
| CH₂Cl | Me | H | H | 2 | H | H | 4-Ethoxy-2-methylamino-6-trifluoromethylpyrimidin-5-yl |
| CH₂Cl | Me | H | H | 2 | H | H | 2-Dimethylamino-4-methoxy-6-trifluoromethylpyrimidin-5-yl |
| CH₂Cl | Me | H | H | 2 | H | H | 2-Dimethylamino-4-ethoxy-6-trifluoromethylpyrimidin-5-yl |

TABLE 52

| R¹ | R² | R³ | R⁴ | n | R⁵ | R⁶ | Y¹ |
|---|---|---|---|---|---|---|---|
| CH₂Cl | Me | H | H | 2 | H | H | 4-Cyano6-trifluoromethylpyrimidin-5-yl |
| CH₂Cl | Me | H | H | 0 | H | H | 4-iso-Propoxy-6-trifluoromethylpyrimidin-5-yl |
| CH₂Cl | Me | H | H | 0 | H | H | 4-Difluoromethoxy-6-trifluoromethylpyrimidin-5-yl |
| CH₂Cl | Me | H | H | 0 | H | H | 4-Methoxy-2-methyl-6-trifluoromethylpyrimidin-5-yl |
| CH₂Cl | Me | H | H | 0 | H | H | 4-Ethoxy-2-methyl-6-trifluoromethylpyrimidin-5-yl |
| CH₂Cl | Me | H | H | 0 | H | H | 2,4-Dimethoxy-6-trifluoromethylpyrimidin-5-yl |
| CH₂Cl | Me | H | H | 0 | H | H | 2,4-Ethoxy-6-trifluoromethylpyrimidin-5-yl |
| CH₂Cl | Me | H | H | 0 | H | H | 2-Amino-4-methoxy-6-trifluoromethylpyrimidin-5-yl |
| CH₂Cl | Me | H | H | 0 | H | H | 2-Amino-4-ethoxy-6-trifluoromethylpyrimidin-5-yl |
| CH₂Cl | Me | H | H | 0 | H | H | 4-Methoxy-2-methylthio-6-trifluoromethylpyrimidin-5-yl |
| CH₂Cl | Me | H | H | 0 | H | H | 4-Ethoxy-2-methylthio-6-trifluoromethylpyrimidin-5-yl |
| CH₂Cl | Me | H | H | 0 | H | H | 4-Methoxy-2-methylsulfonyl-6-trifluoromethylpyrimidin-5-yl |
| CH₂Cl | Me | H | H | 0 | H | H | 4-Ethoxy-2-methylsulfonyl-6-trifluoromethylpyrimidin-5-yl |
| CH₂Cl | Me | H | H | 0 | H | H | 2-Difluoromethoxy-4-methoxy-6-trifluoromethylpyrimidin-5-yl |
| CH₂Cl | Me | H | H | 0 | H | H | 2-Difluoromethoxy-4-ethoxy-6-trifluoromethylpyrimidin-5-yl |
| CH₂Cl | Me | H | H | 0 | H | H | 2-Cyano-4-methoxy-6-trifluoromethylpyrimidin-5-yl |
| CH₂Cl | Me | H | H | 0 | H | H | 2-Cyano-4-ethoxy-6-trifluoromethylpyrimidin-5-yl |
| CH₂Cl | Me | H | H | 0 | H | H | 4-Methoxy-2-methylamino-6-trifluoromethylpyrimidin-5-yl |
| CH₂Cl | Me | H | H | 0 | H | H | 4-Ethoxy-2-methylamino-6-trifluoromethylpynmidin-5-yl |
| CH₂Cl | Me | H | H | 0 | H | H | 2-Dimethylamino-4-methoxy-6-trifluoromethylpyrimidin-5-yl |

TABLE 53

| R¹ | R² | R³ | R⁴ | n | R⁵ | R⁶ | Y¹ |
|---|---|---|---|---|---|---|---|
| CH₂Cl | Me | H | H | 0 | H | H | 2-Dimethylamino-4-ethoxy-6-trifluoromethylpyrimidin-5-yl |
| CH₂Cl | Me | H | H | 0 | H | H | 4-Cyano6-trifluoromethylpyrimidin-5-yl |
| CHCl₂ | Me | H | H | 2 | H | H | 4-Ethoxy-6-trifluoromethylpyrimidin-5-yl |
| CHF₂ | Me | H | H | 2 | H | H | 4-Ethoxy-6-trifluoromethylpyrimidin-5-yl |
| CHClF | Me | H | H | 2 | H | H | 4-Ethoxy-6-trifluoromethylpyrimidin-5-yl |
| CHFMe | Me | H | H | 2 | H | H | 4-Ethoxy-6-trifluoromethylpyrimidin-5-yl |
| CHClMe | Me | H | H | 2 | H | H | 4-Ethoxy-6-trifluoromethylpyrimidin-5-yl |

TABLE 53-continued

| R¹ | R² | R³ | R⁴ | n | R⁵ | R⁶ | Y¹ |
|---|---|---|---|---|---|---|---|
| CF₂Me | Me | H | H | 2 | H | H | 4-Ethoxy-6-trifluoromethylpyrimidin-5-yl |
| CH₂CH₂F | Me | H | H | 2 | H | H | 4-Ethoxy-6-trifluoromethylpyrimidin-5-yl |
| CH₂CHF₂ | Me | H | H | 2 | H | H | 4-Ethoxy-6-trifluoromethylpyrimidin-5-yl |
| CH₂CH₂Cl | Me | H | H | 2 | H | H | 4-Ethoxy-6-trifluoromethylpyrimidin-5-yl |
| CH₂CHCl₂ | Me | H | H | 2 | H | H | 4-Ethoxy-6-trifluoromethylpyrimidin-5-yl |
| CH₂CClF₂ | Me | H | H | 2 | H | H | 4-Ethoxy-6-trifluoromethylpyrimidin-5-yl |
| CH₂CF₃ | Me | H | H | 2 | H | H | 4-Ethoxy-6-trifluoromethylpyrimidin-5-yl |
| CF₂CF₃ | Me | H | H | 2 | H | H | 4-Ethoxy-6-trifluoromethylpyrimidin-5-yl |
| CH₂CH₂CF₃ | Me | H | H | 2 | H | H | 4-Ethoxy-6-trifluoromethylpyrimidin-5-yl |
| CH₂CH₂CHF | Me | H | H | 2 | H | H | 4-Ethoxy-6-trifluoromethylpyrimidin-5-yl |
| CF₂CF₂CF₃ | Me | H | H | 2 | H | H | 4-Ethoxy-6-trifluoromethylpyrimidin-5-yl |
| CH₂CF₂Me | Me | H | H | 2 | H | H | 4-Ethoxy-6-trifluoromethylpyrimidin-5-yl |
| CH₂CHFMe | Me | H | H | 2 | H | H | 4-Ethoxy-6-trifluoromethylpyrimidin-5-yl |
| CF₃ | CF₃ | H | H | 2 | H | H | 4-Ethoxy-6-trifluoromethylpyrimidin-5-yl |
| CHFPr-n | Me | H | H | 2 | H | H | 4-Ethoxy-6-trifluoromethylpyrimidin-5-yl |
| CF₂Pr-n | Me | H | H | 2 | H | H | 4-Ethoxy-6-trifluoromethylpyrimidin-5-yl |
| CHCl₂ | Me | H | H | 0 | H | H | 4-Ethoxy-6-trifluoromethylpyrimidin-5-yl |
| CHF₂ | Me | H | H | 0 | H | H | 4-Ethoxy-6-trifluoromethylpyrimidin-5-yl |
| CHClF | Me | H | H | 0 | H | H | 4-Ethoxy-6-trifluoromethylpyrimidin-5-yl |
| CHFMe | Me | H | H | 0 | H | H | 4-Ethoxy-6-trifluoromethylpyrimidin-5-yl |
| CHClMe | Me | H | H | 0 | H | H | 4-Ethoxy-6-trifluoromethylpyrimidin-5-yl |
| CF₂Me | Me | H | H | 0 | H | H | 4-Ethoxy-6-trifluoromethylpyrimidin-5-yl |
| CH₂CH₂F | Me | H | H | 0 | H | H | 4-Ethoxy-6-trifluoromethylpyrimidin-5-yl |
| CH₂CHF₂ | Me | H | H | 0 | H | H | 4-Ethoxy-6-trifluoromethylpyrimidin-5-yl |
| CH₂CH₂Cl | Me | H | H | 0 | H | H | 4-Ethoxy-6-trifluoromethylpyrimidin-5-yl |
| CH₂CHCl₂ | Me | H | H | 0 | H | H | 4-Ethoxy-6-trifluoromethylpyrimidin-5-yl |
| CH₂CClF₂ | Me | H | H | 0 | H | H | 4-Ethoxy-6-trifluoromethylpyrimidin-5-yl |

TABLE 54

| R¹ | R² | R³ | R⁴ | n | R⁵ | R⁶ | Y¹ |
|---|---|---|---|---|---|---|---|
| CH₂CF₃ | Me | H | H | 0 | H | H | 4-Ethoxy-6-trifluoromethylpyrimidin-5-yl |
| CF₂CF₃ | Me | H | H | 0 | H | H | 4-Ethoxy-6-trifluoromethylpyrimidin-5-yl |
| CH₂CH₂CF₃ | Me | H | H | 0 | H | H | 4-Ethoxy-6-trifluoromethylpyrimidin-5-yl |
| CH₂CH₂CHF | Me | H | H | 0 | H | H | 4-Ethoxy-6-trifluoromethylpyrimidin-5-yl |
| CF₂CF₂CF₃ | Me | H | H | 0 | H | H | 4-Ethoxy-6-trifluoromethylpyrimidin-5-yl |
| CH₂CF₂Me | Me | H | H | 0 | H | H | 4-Ethoxy-6-trifluoromethylpyrimidin-5-yl |
| CH₂CHFMe | Me | H | H | 0 | H | H | 4-Ethoxy-6-trifluoromethylpyrimidin-5-yl |
| CF₃ | CF₃ | H | H | 0 | H | H | 4-Ethoxy-6-trifluoromethylpyrimidin-5-yl |
| CHFPr-n | Me | H | H | 0 | H | H | 4-Ethoxy-6-trifluoromethylpyrimidin-5-yl |
| CF₂Pr-n | Me | H | H | 0 | H | H | 4-Ethoxy-6-trifluoromethylpyrimidin-5-yl |

TABLE 55

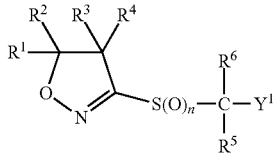

| R¹ | R² | R³ | R⁴ | n | R⁵ | R⁶ | Y¹ |
|---|---|---|---|---|---|---|---|
| CH₂Cl | Me | H | H | 2 | H | H | Benzimidazol-2-yl |
| CH₂Cl | Me | H | H | 2 | H | H | Benzothiophen-2-yl |
| CH₂Cl | Me | H | H | 2 | H | H | 3-Chlorobenzothiophen-2-yl |
| CH₂Cl | Me | H | H | 2 | H | H | Benzotriazol-1-yl |
| CH₂Cl | Me | H | H | 2 | H | H | 1-Methylindazol-4-yl |
| CH₂Cl | Me | H | H | 2 | H | H | Benzoxazol-2-yl |
| CH₂Cl | Me | H | H | 2 | H | H | 3-Methylbenzothiophen-2-yl |
| CH₂Cl | Me | H | H | 2 | H | H | 3-Bromobenzothiophen-2-yl |
| CH₂Cl | Me | H | H | 2 | H | H | Benzothiophen-7-yl |
| CF₃ | Me | H | H | 2 | H | H | Benzothiophen-7-yl |
| CH₂F | Me | H | H | 2 | H | H | Benzothiophen-7-yl |
| CH₂Cl | Me | H | H | 2 | H | H | 1-Methylindazol-7-yl |
| CH₂Cl | Me | H | H | 2 | H | H | 3-Chloro-1-methylindol-2-yl |
| CH₂Cl | Me | H | H | 1 | H | H | Benzimidazol-2-yl |
| CH₂Cl | Me | H | H | 1 | H | H | Benzothiophen-2-yl |

TABLE 55-continued

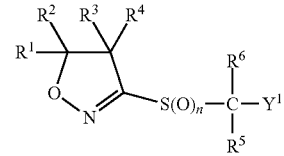

| R¹ | R² | R³ | R⁴ | n | R⁵ | R⁶ | Y¹ |
|---|---|---|---|---|---|---|---|
| CH₂Cl | Me | H | H | 1 | H | H | 3-Chlorobenzothiophen-2-yl |
| CH₂Cl | Me | H | H | 1 | H | H | Benzotriazol-1-yl |
| CH₂Cl | Me | H | H | 1 | H | H | 1-Methylindazol-4-yl |
| CH₂Cl | Me | H | H | 1 | H | H | Benzothiophen-3-yl |
| CH₂Cl | Me | H | H | 1 | H | H | 5-Chlorobenzothiophen-3-yl |
| CH₂Cl | Me | H | H | 1 | H | H | Benzoxazol-2-yl |
| CH₂Cl | Me | H | H | 1 | H | H | 3-Methylbenzothiophen-2-yl |
| CH₂Cl | Me | H | H | 1 | H | H | 3-Bromobenzothiophen-2-yl |
| CH₂Br | Me | H | H | 1 | H | H | Benzothiophen-7-yl |
| CF₃ | Me | H | H | 1 | H | H | Benzothiophen-7-yl |
| CH₂F | Me | H | H | 1 | H | H | Benzothiophen-7-yl |
| CH₂Cl | Me | H | H | 1 | H | H | Benzothiophen-7-yl |
| CH₂Cl | Me | H | H | 1 | H | H | 1-Methylindazol-7-yl |

TABLE 56

| $R^1$ | $R^2$ | $R^3$ | $R^4$ | n | $R^5$ | $R^6$ | $Y^1$ |
|---|---|---|---|---|---|---|---|
| $CH_2Cl$ | Me | H | H | 1 | H | H | 3-Chloro-1-methylindol-2-yl |
| $CH_2Cl$ | Me | H | H | 0 | H | H | Benzimidazol-2-yl |
| $CH_2Cl$ | Me | H | H | 0 | H | H | Benzothiophen-2-yl |
| $CH_2Cl$ | Me | H | H | 0 | H | H | 3-Chlorobenzothiophen-2-yl |
| $CH_2Cl$ | Me | H | H | 0 | H | H | Benzotriazol-1-yl |
| $CH_2Cl$ | Me | H | H | 0 | H | H | 1-Methylindazol-4-yl |
| $CH_2Cl$ | Me | H | H | 0 | H | H | Benzothiophen-3-yl |
| $CH_2Cl$ | Me | H | H | 0 | H | H | 5-Chlorobenzothiophen-3-yl |
| $CH_2Cl$ | Me | H | H | 0 | H | H | Benzoxazol-2-yl |
| $CH_2Cl$ | Me | H | H | 0 | H | H | 3-Methylbenzothiophen-2-yl |
| $CH_2Cl$ | Me | H | H | 0 | H | H | 3-Bromobenzothiophen-2-yl |
| $CH_2Br$ | Me | H | H | 0 | H | H | Benzothiophen-7-yl |
| $CF_3$ | Me | H | H | 0 | H | H | Benzothiophen-7-yl |
| $CH_2F$ | Me | H | H | 0 | H | H | Benzothiophen-7-yl |
| $CH_2Cl$ | Me | H | H | 0 | H | H | Benzothiophen-7-yl |
| $CH_2Cl$ | Me | H | H | 0 | H | H | 1-Methylindazol-7-yl |
| $CH_2Cl$ | Me | H | H | 0 | H | H | 3-Chloro-1-methylindol-2-yl |
| $CH_2Cl$ | Pr-c | H | H | 2 | H | H | Benzoxazol-2-yl |
| $CH_2Cl$ | Me | H | H | 2 | H | H | 4-Chlorobenzoxazol-2-yl |
| $CH_2Cl$ | Me | H | H | 2 | H | H | 5-Chlorobenzoxazol-2-yl |
| $CH_2Cl$ | Me | H | H | 2 | H | H | 6-Chlorobenzoxazol-2-yl |
| $CH_2Cl$ | Me | H | H | 2 | H | H | 7-Chlorobenzoxazol-2-yl |
| $CH_2Cl$ | Me | H | H | 2 | H | H | 4-Fluorobenzoxazol-2-yl |
| $CH_2Cl$ | Me | H | H | 2 | H | H | 5-Fluorobenzaxazol-2-yl |
| $CH_2Cl$ | Me | H | H | 2 | H | H | 6-Fluorobenzoxazol-2-yl |
| $CH_2Cl$ | Me | H | H | 2 | H | H | 7-Fluorobenzoxazol-2-yl |
| $CH_2Cl$ | $CH_2Pr$-c | H | H | 2 | H | H | 4-Methylbenzoxazol-2-yl |
| $CH_2Cl$ | Me | H | H | 2 | H | H | 5-Methylbenzoxazol-2-yl |
| $CH_2Cl$ | Me | H | H | 2 | H | H | 6-Methylbenzoxazol-2-yl |
| $CH_2Cl$ | Me | H | H | 2 | H | H | 7-Methylbenzoxazol-2-yl |
| $CH_2Cl$ | Me | H | H | 2 | H | H | 4-Methoxybenzoxazol-2-yl |
| $CH_2Cl$ | Me | H | H | 2 | H | H | 5-Methoxybenzoxazol-2-yl |
| $CH_2Cl$ | Me | H | H | 2 | H | H | 6-Methoxybenzoxazol-2-yl |

TABLE 57

| $R^1$ | $R^2$ | $R^3$ | $R^4$ | n | $R^5$ | $R^6$ | $Y^1$ |
|---|---|---|---|---|---|---|---|
| $CH_2Cl$ | Me | H | H | 2 | H | H | 7-Methoxybenzoxazol-2-yl |
| $CH_2Cl$ | Me | H | H | 2 | H | H | Quinolin-2-yl |
| $CH_2Cl$ | $CH_2Cl$ | H | H | 2 | H | H | Quinolin-6-yl |
| $CH_2Cl$ | Me | H | H | 2 | H | H | Quinoxalin-2-yl |

The compound of the present invention having the general formula [I] can be produced by the processes shown below. However, the production is not restricted to these processes alone.

[Production Process 1]

(Step 1 to Step 5)

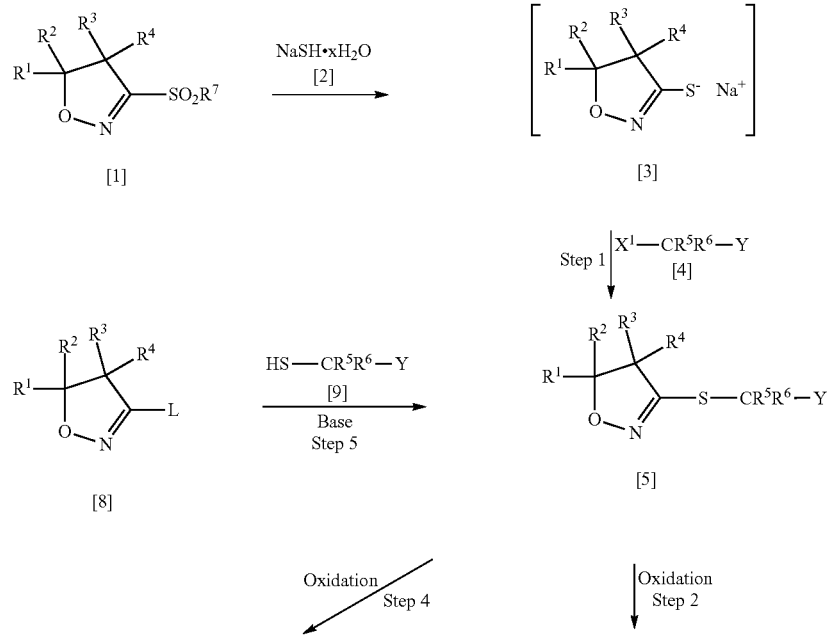

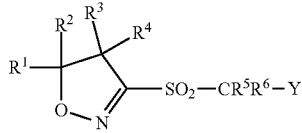 -continued 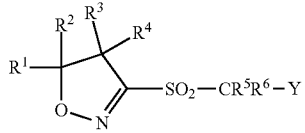

[7]     Oxidation Step 3     [6]

wherein $R^1$, $R^2$, $R^3$, $R^4$, $R^5$, $R^6$ and Y have the same meanings as given above; $X^1$ is a halogen atom; $R^7$ is a C1 to C4 alkyl group, an optionally substituted phenyl group or an optionally substituted benzyl group; L is an eliminatable group such as halogen atom, C1 to C4 alkylsulfonyl group, optionally substituted phenylsulfonyl group, optionally substituted benzylsulfonyl group or the like; and x is a number of 1 or more.

The individual steps of the above production process are described in detail below.

(Step 1)

A sulfide derivative represented by the general formula [5] can be produced by reacting a compound represented by the genera formula [1] with a sodium hydrosulfide hydrate represented by the general formula [2] in a solvent or in the absence of a solvent (preferably in an appropriate solvent) in the presence or absence of a base to produce a mercaptan salt represented by the general formula [3] in the reaction system and then reacting the mercaptan salt [3] with a halogen derivative represented by the general formula [4] without isolating the mercaptan salt [3] {optionally, a radical generator [e.g. Rongalit (trade name), $CH_2(OH)SO_2Na.2H_2O$] may be added}.

The reaction temperature in each reaction is any temperature ranging from 0° C. to the reflux temperature in reaction system, preferably a temperature range of 0° C. to 100° C. The reaction time is 0.5 to 24 hours although it differs depending upon the compounds used.

With respect to the amounts of the reagents used in the reactions, the amounts of the compound represented by the general formula [2] and the compound represented by the general formula [4] are each 1 to 3 equivalents relative to 1 equivalent of the compound represented by the general formula [1]; and when a base is used, the amount of the base is 0.5 to 3 equivalents.

As the solvent used, there can be mentioned, for example, ethers such as dioxane, tetrahydrofuran (THF) and the like; halogenated hydrocarbons such as dichloroethane, carbon tetrachloride, chlorobenzene, dichlorobenzene and the like; amides such as N,N-dimethylacetamide, N,N-dimethylformamide (DMF), N-methyl-2-pyrrolidinone and the like; sulfur compounds such as dimethyl sulfoxide, (DMSO), sulfolane and the like; aromatic hydrocarbons such as benzene, toluene, xylene and the like; alcohols such as methanol, ethanol, propanol, isopropanol, butanol, tert-butanol and the like; ketones such as acetone, 2-butanone and the like; nitriles such as acetonitrile and the like; water; and mixtures thereof.

As the base used, there can be mentioned, for example, metal hydrides such as sodium hydride and the like; alkali metal amides such as sodium amide, lithium diisopropylamide and the like; organic bases such as pyridine, triethylamine, 1,8-diazabicyclo[5.4.0]-7-undecene and the like; alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal bicarbonates such as sodium hydrogen carbonate, potassium hydrogen carbonate and the like (inorganic bases); and metal alcoholates such as sodium methoxide, sodium ethoxide, potassium tertbutoxide and the like.

(Step 2)

A sulfoxide derivative represented by the general formula [6] can be produced by reacting the sulfide derivative represented by the general formula [5] with an oxidizing agent in an appropriate solvent in the presence or absence of a catalyst.

The reaction temperature is any temperature ranging from 0° C. to the reflux temperature in reaction system, preferably a temperature range of 0° C. to 60° C. The reaction time is 1 to 72 hours although it differs depending upon the compounds used.

With respect to the amounts of the reagents used in the reaction, the amount of the oxidizing agent is 1 to 3 equivalents relative to 1 equivalent of the compound represented by the general formula [5] and, when the catalyst is used, the amount of the catalyst is 0.01 to 0.5 equivalent.

As the solvent used, there can be mentioned, for example, halogenated hydrocarbons such as dichloromethane, chloroform, dichloroethane, carbon tetrachloride, chlorobenzene, dichlorobenzene and the like; ethers such as dioxane, tetrahydrofuran (THF), dimethoxyethane, diethyl ether and the like; amides such as N,N-dimethylacetamide, N,N-dimethylformamide (DMF), N-methyl-2-pyrrolidinone and the like; alcohols such as methanol ethanol, propanol, isopropanol, butanol, tert-butanol and the like; ketones such as acetone, 2-butanone and the like; nitrites such as acetonitrile and the like; acetic acid; water; and mixtures thereof.

As the oxidizing agent used, there can be mentioned, for example, organic peroxides such as m-chloroperbenzoic acid, hydrogen peroxide, performic acid, peracetic acid and the like; and inorganic peroxides such as potassium permanganate, sodium periodate and the like.

As the catalyst used, there can be mentioned, for example, metal catalysts such as sodium tungstate and the like.

(Step 3)

A sulfone derivative represented by the general formula [7] can be produced by reacting the sulfoxide derivative represented by the general formula [6] with an oxidizing agent in an appropriate solvent in the presence or absence of a catalyst.

The reaction temperature is any temperature ranging from 0° C. to the reflux temperature in reaction system, preferably a temperature range of 0° C. to 60° C. The reaction time is 1 to 72 hours although it differs depending upon the compounds used.

With respect to the amounts of the reagents used in the reaction, the amount of the oxidizing agent is 1 to 3 equivalents relative to 1 equivalent of the compound represented by the general formula [6] and, when the catalyst is used, the amount of the catalyst is 0.01 to 0.5 equivalent.

The solvent, oxidizing agent and catalyst used can be the same as used in the step 2.

(Step 4)

The sulfone derivative represented by the general formula [7] can also be produced by reacting the sulfide derivative represented by the general formula [5] with an oxidizing agent of an appropriate amount in an appropriate solvent in the presence or absence of a catalyst, without isolating the sulfoxide derivative represented by the general formula [6].

The reaction temperature is any temperature ranging from 0° C. to the reflux temperature in reaction system, preferably a temperature range of 0° C. to 60° C. The reaction time is 1 to 72 hours although it differs depending upon the compounds used.

With respect to the amounts of the reagents used in the reaction, the amount of the oxidizing agent is 1 to 3 equivalents relative to 1 equivalent of the compound represented by the general formula [5] and, when the catalyst is used, the amount of the catalyst is 0.01 to 0.5 equivalent.

The solvent, oxidizing agent and catalyst used can be the same as used in the step 2.

(Step 5)

The sulfide derivative represented by the general formula [5] can also be produced by reacting a compound represented by the general formula [8] with a mercaptan derivative represented by the general formula [9] in a solvent or in the absence of a solvent (preferably in an appropriate solvent) in the presence of a base.

The reaction temperature is any temperature ranging from 0° C. to the reflux temperature in reaction system, preferably a temperature range of 0° C. to 100° C. The reaction time is 0.5 to 24 hours although it differs depending upon the compounds used.

With respect to the amounts of the reagents used in the reaction, the amount of the compound represented by the general formula [9] is 1 to 3 equivalents relative to 1 equivalent of the compound represented by the general formula [8] and the amount of the base is 0.5 to 3 equivalents.

As the solvent used, there can be mentioned, for example, ethers such as diethyl ether, dimethoxyethane, dioxane, tetrahydrofuran (THF) and the like; halogenated hydrocarbons such as dichloromethane, chloroform, carbon tetrachloride, dichloroethane, chlorobenzene, dichlorobenzene and the like; amides such as N,N-dimethylacetamide, N,N-dimethylformamide (DMF), N-methyl-2-pyrrolidinone and the like; sulfur compounds such as dimethyl sulfoxide, (DMSO), sulfolane and the like; aromatic hydrocarbons such as benzene, toluene, xylene and the like; alcohols such as methanol, ethanol, propanol, isopropanol, butanol, tert-butanol and the like; ketones such as acetone, 2-butanone and the like; nitriles such as acetonitrile and the like; water; and mixtures thereof.

As the base used, there can be mentioned, for example, metal hydrides such as sodium hydride and the like; alkali metal amides such as sodium amide, lithium diisopropylamide and the like; organic bases such as pyridine, triethylamine, 1,8-diazabicyclo[5.4.0]-7-undecene and the like; alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal bicarbonates such as sodium hydrogen carbonate, potassium hydrogen carbonate and the like (inorganic bases); and metal alkoxides such as sodium methoxide, sodium ethoxide, potassium tert-butoxide and the like.

Of the compounds represented by general formula [8], those wherein L is a halogen atom, i.e. a compound represented by the general formula [12] and a compound represented by the general formula [13] can be produced by the following method.

(Step 6)

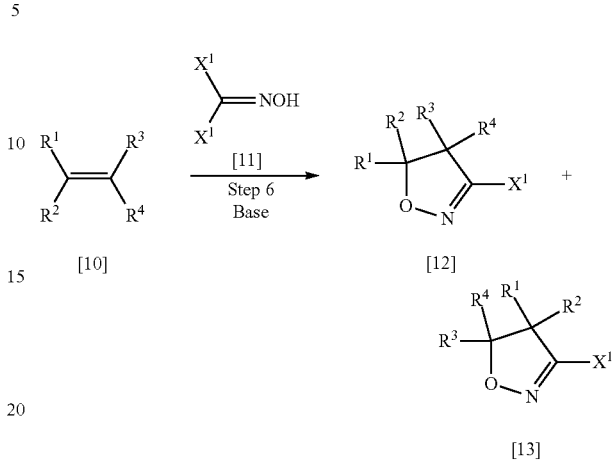

wherein $X^1$, $R^1$, $R^2$, $R^3$ and $R^4$ have the same meanings as given above.

The isoxazoline compounds represented by the general formulas [12] and [13] can be produced by reacting an olefin derivative represented by the general formula [10] with an oxime derivative represented by the general formula [11] in a solvent or in the absence of a solvent (preferably in an appropriate solvent) in the presence of a base. As necessary, the compounds of the general formula [12] and [13] are separated from each other and purified. However, when both $R^3$ and $R^4$ are a hydrogen atom, the isoxazoline compound represented by the general formula [12] is obtained predominantly.

The reaction temperature is any temperature ranging from 0° C. to the reflux temperature in reaction system, preferably a temperature range of 0° C. to 80° C. The reaction time is 0.5 hour to 2 weeks although it differs depending upon the compounds used.

With respect to the amounts of the reagents used in the reaction, the amount of the compound represented by the general formula [10] is 1 to 3 equivalents relative to 1 equivalent of the compound represented by the general formula [11].

As the solvent used, there can be mentioned, for example, ethers such as ethylene glycol dimethyl ether, ethylene glycol diethyl ether, diethyl ether, dioxane, tetrahydrofuran and the like; halogenated hydrocarbons such as dichloroethane, carbon tetrachloride, chlorobenzene, dichlorobenzene and the like; aromatic hydrocarbons such as benzene, toluene, xylene and the like, esters such as ethyl acetate, butyl acetate and the like; water; and mixtures thereof.

As the base used, there can be mentioned, for example, alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal bicarbonates such as sodium hydrogen carbonate, potassium hydrogen carbonate and the like; alkali metal acetates such as sodium acetate, potassium acetate and the like; alkali metal fluorides such as sodium fluoride, potassium fluoride and the like; and organic bases such as pyridine, triethylamine, 1,8-diazabicyclo [5.4.0]-7-undecene and the like.

Incidentally, the compound represented by the general formula [10] used in the above production process as an intermediate may be a commercial product or can be produced by a known reaction such as the Witting reaction or the like. The compound represented by the general formula [11] can be produced by, for example, the method described in Liebigs Annalen der Chemie, 985 (1989).

The compound represented by the general formula [1] can be produced from the previously shown compound represented by the general formula [12] by the following methods.

(Step 7 to Step 10)

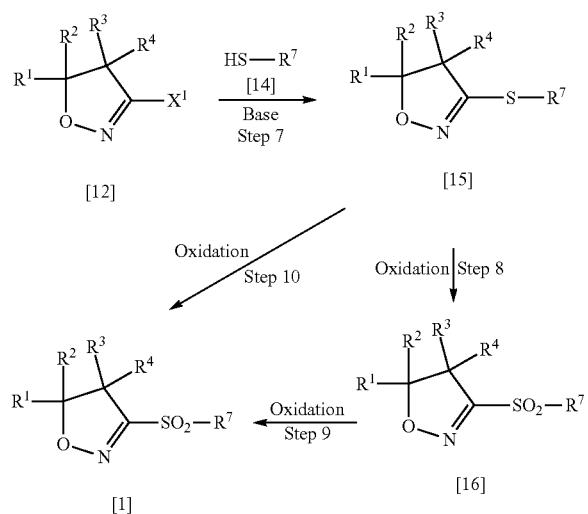

wherein $X^1$, $R^1$, $R^2$, $R^3$, $R^4$ and $R^7$ have the same meanings as given above.

A compound represented by the general formula [15] can be produced based on the method shown in the step 5 (step 7); a compound represented by the general formula [16] can be produced based on the method shown in the step 2 (step 8); the compound represented by the general formula [1] can be produced from the compound of the general formula [15] based on the method shown in the step 4 (step 10), or from the compound of the general formula [16] based on the method shown in the step 3 (step 9). The solvent, base, oxidizing agent and catalyst used can be the same as used in the step 2, the step 3, the step 4 or the step 5.

Of the compounds represented by the general formula [4], a compound represented by the general formula [21] can be produced by the methods shown below.

(Steps 11 and 12)

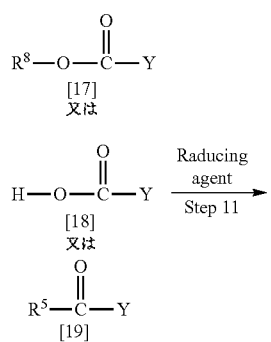

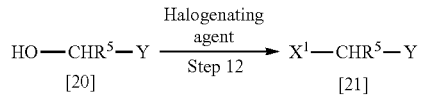

wherein $R^5$, $X^1$ and Y have the same meanings as given above; and $R^8$ is an alkyl group.

(Step 11)

A compound represented by the general formula [20] can be produced by reacting a compound of the general formula [17], [18] or [19] with a reducing agent in a solvent.

This reaction is conducted ordinarily at a temperature of −60 to 150° C. for 10 minutes to 24 hours.

With respect to the amounts of the reagents used, the amount of the reducing agent is desired to be 0.5 to 2 equivalents per 1 equivalent of the compound of the general formula [17], [18] or [19], but it can be varied appropriately depending upon the conditions of the reaction.

As the reducing agent, there can be mentioned, in production of the compound of the general formula [20] from the compound of the general formula [17], metal hydrides such as diisobutyl aluminum hydride and the like; metal-hydrogen complex compounds such as sodium borohydride, lithium aluminum hydride and the like; and so forth. In production of the compound of the general formula [20] from the compound of the general formula [18] or [19], there can be mentioned, for example, metal hydrides such as diisobutyl aluminum hydride and the like; metal-hydrogen complex compounds such as sodium borohydride, lithium aluminum hydride and the like; and diborane.

As the solvent used, there can be mentioned, for example, ethers such as diethyl ether, tetrahydrofuran, dioxane and the like; aromatic hydrocarbons such as benzene, toluene and the like; and alcohols such as methanol, ethanol and the like.

(Step 12)

A compound represented by the general formula [21] can be produced by reacting the compound of the general formula [20] with a halogenating agent in a solvent.

This reaction is conducted ordinarily at −50 to 100° C. for 10 minutes to 24 hours.

With respect to the amounts of the reagents used, the amount of the halogenating agent is desired to be 1 to 3 equivalents per 1 equivalent of the compound of the general formula [20] but it can be varied appropriately depending upon the conditions of the reaction.

As the halogenating agent used, there can be mentioned, for example, hydrogen chloride, hydrogen bromide, phosphorus trichloride, phosphorus tribromide, and thionyl chloride.

As the solvent used, there can be mentioned, for example, halogenated hydrocarbons such as dichloroethane, carbon tetrachloride and the like; acids such as acetic acid and the like; and ethers such as tetrahydrofuran and the like.

The compound represented by the general formula [4] can be produced by the following method.

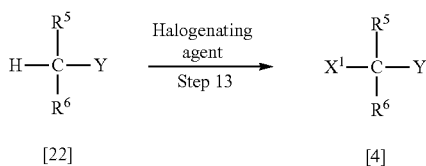

[22] [4]

wherein $R^5$, $R^6$, $X^1$ and Y have the same meanings as given above.

(Step 13)

The compound represented by the general formula [4] can be produced by reacting a compound represented by the general formula [22] with a halogenating agent in a solvent in the presence or absence of a catalyst. In this step, the reaction may be conducted under light irradiation.

This reaction is conducted ordinarily at 30 to 150° C. for 10 minutes to 24 hours.

With respect to the amounts of the reagents used, the amount of the halogenating agent is desired to be 1 to 10 equivalents per 1 equivalent of the compound of the general formula [22] but it can be varied appropriately depending upon the conditions of the reaction. The amount of the catalyst is 0.01 to 0.5 equivalent.

As the halogenating agent used, there can be mentioned, for example, halogens such as bromine, chlorine and the like; N-halosuccinimides such as N-bromosuccinimide and the like; and pyridine salts such as pyridinium perbromide and the like.

As the solvent used, there can be mentioned, for example, halogenated hydrocarbons such as dichloroethane, carbon tetrachloride, chlorobenzene, dichlorobenzene and the like; and carboxylic acids such as formic acid, acetic acid and the like.

As the catalyst used, there can be mentioned, for example, benzoyl peroxide, α,α-azobisisobutyronitrile, and mixtures thereof.

Of the compounds represented by the general formula [4], a compound represented by the general formula [24] can be produced by the following method.

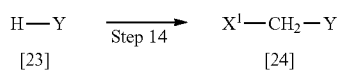

[23] [24]

wherein $X^1$ and Y have the same meanings as given above.

(Step 14)

The compound represented by the general formula [24] can be produced by reacting a compound represented by the general formula [23] with a hydrogen halide and formaldehyde or paraformaldehyde in a solvent in the presence or absence of a Lewis acid, based on the method described in Org. Synth., III, 557 (1955) or J. Am. Chem. Soc., 72, 2216 (1950), or by reacting the compound represented by the general formula [23] with a halogenomethyl ether in a solvent in the presence of a Lewis acid, based on the method described in J. Am. Chem. Soc., 97, 6155 (1975).

This reaction is conducted ordinarily at −40 to 150° C. for 10 minutes to 24 hours.

With respect to the amounts of the reagents used, it is desired that the amount of the hydrogen halide is 1 to 2 equivalents, the amount of formaldehyde or paraformaldehyde is 1 to 2 equivalents, the amount of the Lewis acid is 1 to 2 equivalents, and the amount of the halogenomethyl ether is 1 to 2 equivalents, all relative to 1 equivalent of the compound of the general formula [23]. However, these amounts can be varied appropriately depending upon the conditions of the reaction.

As the Lewis acid used, there can be mentioned, for example, titanium tetrachloride, zinc chloride, aluminum chloride and zinc bromide.

As the hydrogen halide used, there can be mentioned hydrogen chloride, hydrogen bromide and hydrogen iodide.

As the solvent used, there can be mentioned, for example, halogenating hydrocarbons such as dichloroethane, carbon tetrachloride, chloroform and the like; aliphatic hydrocarbons such as hexane, heptane and the like; ethers such as dioxane, tetrahydrofuran and the like; carboxylic acids such as acetic acid and the like; carbon disulfide; and mixtures thereof.

Of the compounds represented by the general formula [19], a compound represented by the general formula [25] can be produced by the following method.

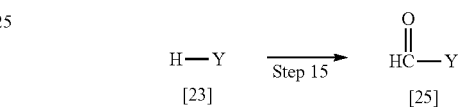

[23] [25]

wherein Y has the same meaning as given above.

(Step 15)

The compound represented by the general formula [25] can be produced by reacting the compound of the general formula [23] with N,N-dimethylformamide (DMF) in a solvent or in the absence of a solvent in the presence of phosphoryl chloride, phosgene or thionyl chloride, based on the method described in Org. Synth., IV, 831 (1963) [Vilsmeier method], or by reacting the compound of the general formula [23] with a dihalogenomethyl ether in a solvent in the presence of a Lewis acid, followed by hydrolysis, based on the method described in Chem. Ber., 93, 88 (1960).

This reaction is conducted ordinarily at −40 to 150° C. for 10 minutes to 24 hours.

With respect to the amounts of reagents used in the reaction, it is desired that the amount of phosphoryl chloride, phosgene or thionyl chloride is 1 to 2 equivalents, the amount of N,N-dimethylformamide is 1 to 2 equivalents, the amount of Lewis acid is 1 to 2 equivalents, and the amount of dihalogenomethyl ether is 1 to 2 equivalents, all relative to 1 equivalent of the compound of the general formula [23]; however, these amounts can be varied appropriately depending upon the conditions of the reaction.

As the Lewis acid used, there can be mentioned, for example, titanium tetrachloride, tin tetrachloride, zinc chloride, aluminum chloride and zinc bromide.

As the solvent used, there can be mentioned, for example, halogenated hydrocarbons such as dichloroethane, carbon tetrachloride, chloroform and the like; aliphatic hydrocarbons such as hexane, heptane and the like; ethers such as dioxane, tetrahydrofuran and the like; carboxylic acids such as acetic acid and the like; amides such as N,N-dimethylformamide and the like; sulfur compound such as carbon disulfide and the like; and mixtures thereof.

The compound represented by the general formula [17], [18] or [19] can be produced by the following method.

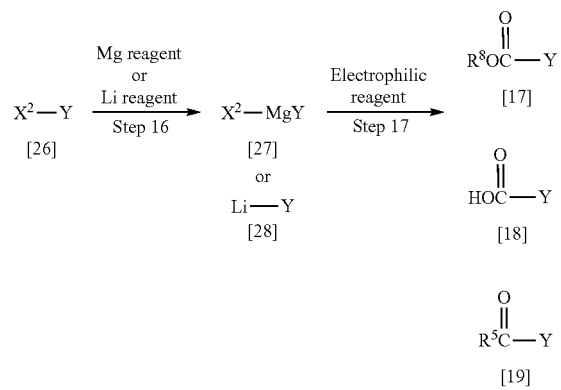

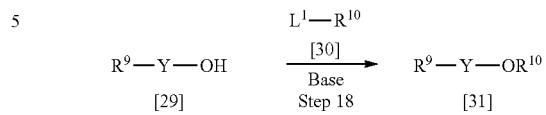

wherein $X^2$ is a chlorine atom, a bromine atom or an iodine atom; and $R^5$, $R^6$ and Y have the same meanings as given above.

(Steps 16 and 17)

The compound represented by the general formula [17], [18] or [19] can be produced by reacting a compound represented by the general formula [26] with a magnesium reagent in a solvent or in the absence of a solvent based on the method described in J. Org. Chem., 65, 4618 (2000), to obtain a compound of the general formula [27] and reacting the compound of the general formula [27] with an electrophilic reagent, or by reacting the compound of the general formula [26] with a lithium reagent based on the method described in Synth. Commun., 24(2), 253 (1994) to obtain a compound of the general formula [28] and reacting the compound of the general formula [28] with an electrophilic reagent.

This reaction is conducted ordinarily at −100 to 150° C. for 10 minutes to 24 hours.

With respect to the amounts of the reagents used in the reaction, it is desired that the amount of the magnesium reagent is 1 to 5 equivalents, the amount of the electrophilic reagent is 1 to 5 equivalents, or the amount of the lithium reagent is 1 to 5 equivalents and the amount of the electrophilic reagent is 1 to 5 equivalents, all relative to 1 equivalent of the compound of the general formula [26]; however, these amounts can be varied appropriately depending upon the conditions of the reaction.

As the magnesium reagent used, there can be mentioned, for example, metallic magnesium, isopropyl magnesium bromide and diisopropyl magnesium and the like.

As the lithium reagent used, there can be mentioned, for example, n-butyl lithium and n-hexyl lithium and the like.

As the electrophilic reagent used, there can be mentioned, for example, esters such as ethyl formate, ethyl cyanoformate, ethyl acetate and the like; acid halides such as acetyl chloride, methyl chloroformate and the like; amides such as N,N-dimethylformamide and the like; and carbon dioxide.

As the solvent used, there can be mentioned, for example, halogenated hydrocarbons such as dichloroethane, carbon tetrachloride, chloroform and the like; aliphatic hydrocarbons such as hexane, pentane and the like; ethers such as dioxane, tetrahydrofuran and the like; and mixtures thereof.

A compound represented by the general formula [31] can be produced by the following method.

$$R^9\text{—Y—OH} \xrightarrow[\text{Base}]{\underset{\text{Step 18}}{L^1\text{—}R^{10}\ [30]}} R^9\text{—Y—OR}^{10}$$
[29]                                                                                                             [31]

wherein Y has the same meaning as given above; $R^9$ is a hydrogen atom, an alkyl group, an acyl group or an alkoxycarbonyl group; $R^{10}$ is an alkyl group, a haloalkyl group, a cycloalkyl group, a cycloalkylalkyl group, an alkoxycarbonylalkyl group, an optionally substituted benzyl group, an optionally substituted heterocyclic alkyl group, alkenyl group, an alkynyl group, an alkylsulfonyl group, a haloalkylsulfonyl group, an optionally substituted aromatic heterocyclic group, an optionally substituted phenylsulfonyl group, an acyl group, a haloalkylcarbonyl group, an optionally substituted benzylcarbonyl group or an optionally substituted benzoyl group; and $L^1$ is an eliminatable group such as halogen atom, C1 to C4 alkylsulfonyloxy group, C1 to C4 alkylsulfonyl group, optionally substituted benzylsulfonyl group, optionally substituted phenylsulfonyloxy group, optionally substituted benzylsulfonyloxy group or the like; when $R^{10}$ is a haloalkyl group, $L^1$ is an eliminatable group having a reactivity higher than that of the halogen atom which remains after haloalkylation and, when $R^{10}$ is, for example, a $CHF_2$ group, $L^1$ is a chlorine atom or a bromine atom and, when $R^{10}$ is a $CH_2CF_3$ group, $L^1$ is a chlorine atom, a bromine atom, an iodine atom, a p-toluenesulfonyloxy group, a methylsulfonyloxy group, a trifluoromethylsulfonyloxy group or the like.

(Step 18)

The compound represented by the general formula [31] can be produced by reacting a compound represented by the general formula [29] with a compound represented by the general formula [30] in a solvent in the presence of a base.

This reaction is conducted ordinarily at 0 to 120° C. for 10 minutes to 24 hours.

With respect to the amounts of the reagents used in the reaction, the amount of the compound represented by the general formula [30] is 1 to 20 equivalents and the amount of the base is 1 to 3 equivalents, all relative to 1 equivalent of the compound represented by the general formula [29].

As the base used, there can be mentioned, for example, alkali metal carbonates such as sodium carbonate, potassium carbonate and the like; alkali metal hydroxides such as sodium hydroxide, potassium hydroxide and the like; alkali metal hydrides such as potassium hydride, sodium hydride and the like; alkali metal alkoxides such as sodium ethoxide, sodium methoxide and the like; and organic bases such as 1,8-diazabicyclo[5.4.0]-7-undecene and the like.

As the solvent used, there can be mentioned, for example, halogenated hydrocarbons such as chloroform, dichloroethane and the like; ethers such as diethyl ether, tetrahydrofuran and the like; aromatic hydrocarbons such as benzene, toluene and the like; aliphatic hydrocarbons such as hexane, heptane and the like; ketones such as acetone, methyl isobutyl ketone and the like; esters such as ethyl acetate and the like; amides such as N-methylpyrrolidone, N,N-dimethylformamide and the like; sulfur compounds such as dimethyl sulfoxide, sulfolane and the like; acetonitrile; and mixtures thereof.

A compound represented by the general formula [34] can be produced by the following method.

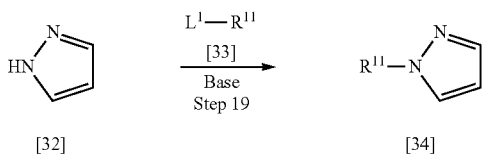

[32]     [34]

wherein L¹, α, β and γ have the same meanings as given above; and R¹¹ is an alkyl group, an alkyl group mono-substituted with a group selected from the substituent group β, a haloalkyl group, a cycloalkyl group, an alkenyl group, an alkynyl group, an alkylsulfinyl group, an alkylsulfonyl group, an alkylsulfonyl group mono-substituted with a group selected from the substituent group γ, a haloalkylsulfonyl group, an optionally substituted phenyl group, an optionally substituted aromatic heterocyclic group, an optionally substituted phenylsulfonyl group, an optionally substituted aromatic heterosulfonyl group, an acyl group, a haloalkylcarbonyl group, an optionally substituted benzylcarbonyl group, an optionally substituted benzoyl group, an alkoxycarbonyl group, an optionally substituted benzyloxycarbonyl group, an optionally substituted phenoxycarbonyl group or a carbamoyl group (its nitrogen atom may be substituted with same or different alkyl groups or an optionally substituted phenyl group; and the carbon atoms of the pyrazole ring may be substituted with 1 to 2 same or different groups selected from the substituent group α.

(Step 19)

The compound represented by the general formula [34] can be produced by reacting a compound represented by the general formula [32] with a compound represented by the general formula [33] in a solvent in the presence of a base.

This reaction is conducted ordinarily at 0 to 120° C. for 10 minutes to 24 hours.

With respect to the amounts of the reagents used in the reaction, the amount of the compound [33] is 1 to 20 equivalents and the amount of the base is 1 to 3 equivalents, all relative to 1 equivalent of the compound represented by the general formula [32].

As the base and solvent used, there can be mentioned, for example, the same substances as used in the step 18.

As the method for introducing a trifluoromethyl group into Y, there can be mentioned, for example, the methods described in J. Chem. Soc. Perkin Trans. 1, 8, 2293-2299 (1990), J. Fluorine Chem., 50(3), 411-426 (1990), J. Chem. Soc. Chem. Commun., 18, 1389-1391 (1993), J. Chem. Soc. Chem. Commun., 1, 53-54 (1992), Chem. Lett., 1719-1720 (1981), Chem. Pharm. Bull., 38(9), 2446-2458 (1990), J. Chem. Soc. Perkin. Trans. 1, 921-926 (1988), Hetercycles, 37(2), 775-782 (1994), Tetrahedron Lett., 30(16), 2133-2136 (1989), J. Chem. Soc. Perkin Trans. 1, 2755-2761 (1980), Hetercycles, 22(1), 117-124 (1984), Eur. J. Med. Chem. Chim. Ther., 24, 249-258 (1989), Acta Chem. Scand. Ser. B, 38(6), 505-508 (1984), J. Fluorine Chem., 21, 495-514 (1982), J. Chem. Soc. Chem. Commun., 10, 638-639 (1988), J. Fluorine Chem., 67(1), 5-6 (1994), J. Heterocycl. Chem., 31(6), 1413-1416 (1994), Chem. Heterocycl. Compd., 30(5), 576-578 (1994), F. Fluorine Chem., 78(2), 177-182 (1996), J. Heterocycl. Chem., 34(2) 551-556 (1997), Tetrahedron, 55(52), 15067-15070 (1999), and Synthesis, 11, 932-933 (1980); and methods similar thereto.

The compounds represented by the general formulas [4], [17], [18], [19], [20], [21], [22], [23], [24], [25], [26], [29] and [31] can be produced by the methods described, when Y is a pyrrolyl group, in Methoden der Organischen Chemie, E6a, 556-798 (1994); when Y is a pyrazolyl group, in Methoden der Organischen Chemie, E8b, 399-763 (1994) or JP-A-2000-219679; when Y is an isothiazolyl group, in Methoden der Organischen Chemie, E8a, 668-798 (1993); when Y is an oxazolyl group, in Methoden der Organischen Chemie, E8a, 891-1019 (1993); when Y is an imidazolyl group, in Methoden der Organischen Chemie, E8c, 1-215 (1994); when Y is a pyridazinyl group, in Methoden der Organischen Chemie, E9a, 557-682 (1997); when Y is a pyrimidinyl group, in Methoden der Organischen Chemie, E9b/1, 1-249 (1998); when Y is a pyrazinyl group, in Methoden der Organischen Chemie, E9b/1, 250-372 (1998); when Y is a triazinyl group, in Methoden der Organischen Chemie, E9c, 530-796 (1998); when Y is a triazolyl group, in Methoden der Organischen Chemie, E8d, 305-405, 479-598 (1994); when Y is an oxadiazolyl group, in Methoden der Organischen Chemie, E8c, 397-818 (1994); when Y is a benzothienyl group, in Methoden der Organischen Chemie, E6b1, 217-322 (1994); when Y is an indolyl group, in Methoden der Organischen Chemie, E6b1, 546-848 (1994), Methoden der Organischen Chemie, E6b2, 849-1336 (1994), or Unexamined International Patent Publication No. WO 97/42188; when Y is a benzoxazolyl group, in Methoden der Organischen Chemie, E8a, 1020-1194 (1993); when Y is a benzoimidazolyl group, in Methoden der Organischen Chemie, E8c, 216-391 (1994); when Y is a benzoisoxazolyl group, in Methoden der Organischen Chemie, E8a, 226-348 (1993); when Y is a benzoisothiazolyl group, in Methoden der Organischen Chemie, E8a, 799-852 (1993); when Y is an indazolyl group, in Methoden der Organischen Chemie, E8b, 764-864 (1994); when Y is a quinolyl group, in Methoden der Organischen Chemie, E7a, 290-570 (1991); when Y is an isoquinolyl group, in Methoden der Organischen Chemie, E7a, 571-758 (1991); when Y is a phthalazinyl group, in Methoden der Organischen Chemie, E9a, 744-789 (1997); when Y is a quinoxalinyl group, in Methoden der Organischen Chemie, E9b/2, 93-265 (1998); when Y is a quinazolinyl group, in Methoden der Organischen Chemie, E9b/2, 1-192 (1998); when Y is a cinnolinyl group, in Methoden der Organischen Chemie, E9a, 683-743 (1997); and when Y is a benzotriazolyl group, in Methoden der Organischen Chemie, E8d, 406-478 (1994); or by methods similar thereto.

[Production Process 2]

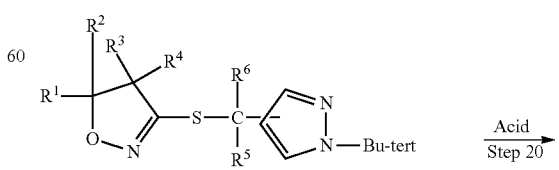

[35]

-continued

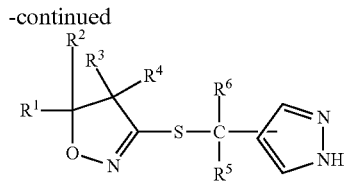

[36]

wherein $R^1$, $R^2$, $R^3$, $R^4$, $R^5$, $R^6$ and α have the same meanings as given above; and the carbon atoms of the pyrazole ring may be substituted with 1 to 2 same or different groups selected from the substituent group α.

(Step 20)

A compound of the present invention represented by the general formula [36] can be produced by reacting a compound of the present invention represented by the general formula [35] (which can be produced by the production process 1) with an acid in a solvent.

This reaction is conducted ordinarily at 0 to 120° C. for 10 minutes to 24 hours.

With respect to the amounts of the reagents used in the reaction, the amount of the acid is desired to be 1 to 10 equivalents per 1 equivalent of the present compound represented by the general formula [35], but can be varied appropriately depending upon the conditions of the reaction.

As the acid used, there can be mentioned, for example, hydrochloric acid, hydrobromic acid and trifluoroacetic acid.

As the solvent used, there can be mentioned, for example, halogenated hydrocarbons such as dichloroethane, carbon tetrachloride, chlorobenzene, dichlorobenzene and the like; amides such as N,N-dimethylacetamide, N,N-dimethylformamide (DMF), N-methyl-2-pyrrolidinone and the like; sulfur compounds such as dimethyl sulfoxide (DMSO), sulfolane and the like; carboxylic acids such as formic acid, acetic acid and the like; and water.

[Production Process 3]

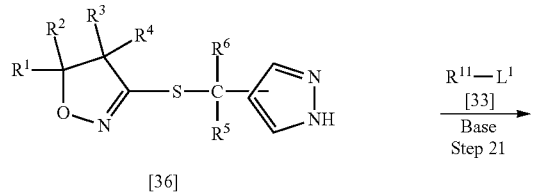

[36]

-continued

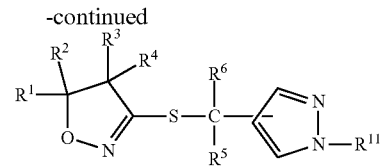

[38]

wherein $R^1$, $R^2$, $R^3$, $R^4$, $R^5$, $R^6$, $R^{11}$ and α have the same meanings as given above; and the carbon atoms of the pyrazole ring may be substituted with 1 to 2 same or different groups selected from the substituent group α.

(Step 21)

A compound of the present invention represented by the general formula [38] can be produced by reacting a compound of the present invention represented by the general formula [36] (which can be produced by the production process 2) with the compound represented by the general formula [33] in a solvent in the presence of a base.

With respect to the amounts of the reagents used in the reaction, the amount of the compound represented by the general formula [33] is 1 to 3 equivalents and the amount of the base is 1 to 3 equivalents, all relative to 1 equivalent of the compound represented by the general formula [36].

As the solvent used, there can be mentioned, for example, ethers such as dioxane, tetrahydrofuran (THF) and the like; halogenated hydrocarbons such as dichloroethane, carbon tetrachloride, chlorobenzene, dichlorobenzene and the like; amides such as N,N-dimethylacetamide, N,N-dimethylformamide (DMF), N-methyl-2-pyrrolidinone and the like; sulfur compounds such as dimethyl sulfoxide (DMSO), sulfolane and the like; aromatic hydrocarbons such as benzene, toluene, xylene and the like; alcohols such as methanol, ethanol, propanol, isopropanol, butanol, tert-butanol and the like; ketones such as acetone, 2-butanone and the like; nitriles such as acetonitrile and the like; water; and mixtures thereof.

As the base used, there can be mentioned, for example, metal hydrides such as sodium hydride and the like; alkali metal amides such as sodium amide, lithium diisopropylamide and the like; organic bases such as pyridine, triethylamine, 1,8-diazabicyclo[5.4.0]-7-undecene and the like; alkali metal hydroxides such as sodium hydroxide, potassium hydroxide and the like; alkaline earth metal hydroxides such as calcium hydroxide, magnesium hydroxide and the like; alkali metal carbonates such as sodium carbonate, potassium carbonate and the like; alkali metal bicarbonates such as sodium hydrogen carbonate, potassium hydrogen carbonate and the like; and metal alkoxides such as sodium methoxide, sodium ethoxide, potassium tert-butoxide and the like.

[Production Process 4]

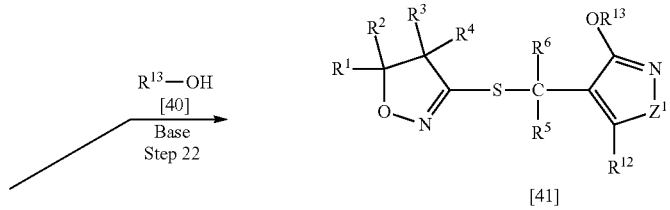

[41]

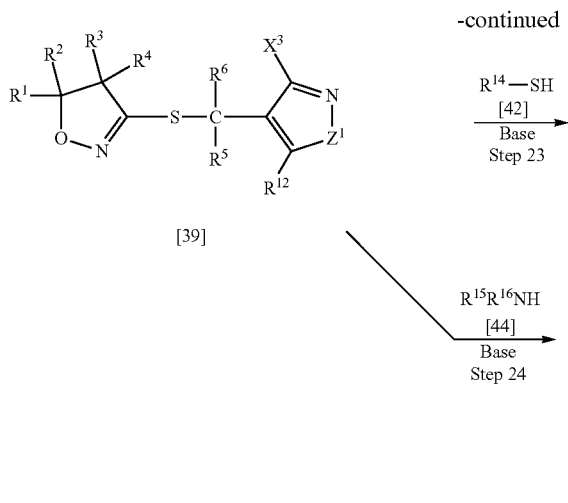

[39]

[43]

[45]

wherein $R^1$, $R^2$, $R^3$, $R^4$, $R^5$, $R^6$ and $R^{10}$ have the same meanings as given above; $R^{12}$ is a trifluoromethyl group, a difluoromethyl group or a difluoromethoxy group; $X^3$ is a chlorine atom or a fluorine atom; $R^{13}$ is an alkyl group, a haloalkyl group, a cycloalkyl group, a cycloalkylalkyl group, an alkenyl group, an alkynyl group, an optionally substituted phenyl group, an optionally substituted aromatic heterocyclic group, an alkoxycarbonylalkyl group, an optionally substituted heteroalkyl group or an optionally substituted benzyl group; $R^{14}$ is an alkyl group, a haloalkyl group, an optionally substituted phenyl group, an optionally substituted aromatic heterocyclic group, an alkoxycarbonylalkyl group or an optionally substituted benzyl group; $R^{15}$ and $R^{16}$ may be the same or different and are each a hydrogen atom, an alkyl group, an optionally substituted phenyl group, an acyl group, a haloalkylcarbonyl group, an optionally substituted benzylcarbonyl group, an optionally substituted benzoyl group, an alkylsulfonyl group, a haloalkylsulfonyl group, an optionally substituted benzylsulfonyl group or an optionally substituted phenylsulfonyl group; and $Z^1$ is a sulfur atom or N—$R^{17}$ ($R^{17}$ is a hydrogen atom or $R^{10}$).

A compound of the present invention represented by the general formula [41], the general formula [43] or the general formula [45] can be produced by reacting a compound of the present invention represented by the general formula [39] with a compound represented by the general formula [40] (step 22), the general formula [42] (step 23) or the general formula [44] (step 24) in the absence or presence of a solvent and, as necessary, in the presence of a base.

This reaction is conducted ordinarily at 20 to 200° C., preferably at 30 to 180° C. for 10 minutes to 48 hours, under pressure if necessary.

With respect to the amounts of the reagents used in the reaction, the amount of the compound represented by the general formula [40], the general formula [42] or the general formula [44] is 1 to 20 equivalents per 1 equivalent of the compound of the present invention represented by the general formula [39].

As the base used, there can be mentioned, for example, inorganic bases such as potassium carbonate, sodium hydroxide, potassium hydride, sodium hydride and the like; alkali metal alkoxides such as sodium ethoxide, sodium methoxide and the like; and organic bases such as 1,8-diazabicyclo [5.4.0]-7-undecene and the like.

As the solvent used, there can be mentioned, for example, halogenated hydrocarbons such as chloroform and the like; ethers such as diethyl ether, tetrahydrofuran and the like; aromatic hydrocarbons such as benzene, toluene and the like; aliphatic hydrocarbons such as hexane, heptane and the like; ketones such as acetone, methyl isobutyl ketone and the like; esters such as ethyl acetate and the like; amides such as N-methylpyrrolidone, N,N-dimethylformamide and the like; sulfur compounds such as dimethyl sulfoxide, sulfolane and the like; nitriles such as acetonitrile and the like; and mixtures thereof.

[Production Process 5]

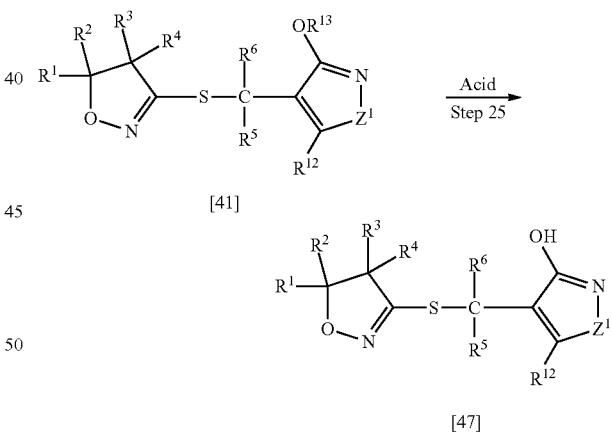

[41]

[47]

wherein $R^1$, $R^2$, $R^3$, $R^4$, $R^5$, $R^6$, $R^{12}$, $R^{13}$ and $Z^1$ have the same meanings as given above.

(Step 25)

A compound of the present invention represented by the general formula [47] can be produced by reacting the present invention compound represented by the general formula [41] with an acid in a solvent.

This reaction is conducted ordinarily at 0 to 120° C. for 10 minutes to 24 hours.

With respect to the amounts of the reagents used in the reaction, the amount of the acid is desirably 1 to 10 equivalents per 1 equivalent of the present invention compound represented by the general formula [41] but can be varied appropriately depending upon the conditions of the reaction.

As the acid and solvent used, there can be mentioned the same substances as used in the production process 2.

[Production Process 6]

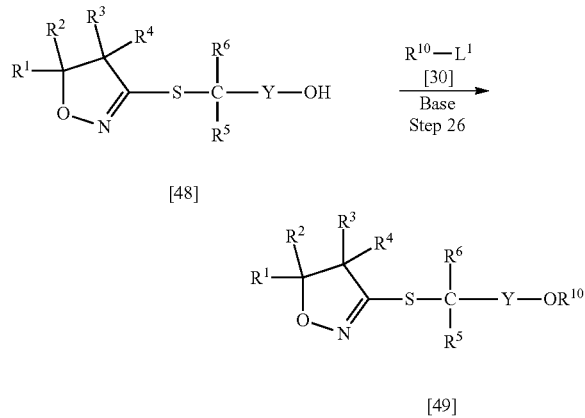

[48]

[49]

wherein Y, $R^1$, $R^2$, $R^3$, $R^4$, $R^5$, $R^6$, $R^{10}$, $L^1$ and α have the same meanings as given above; and Y may be substituted with 1 to 5 same or different groups selected from the substituent group α.

(Step 26)

A compound of the present invention represented by the general formula [49] can be produced by reacting a compound of the present invention represented by the general formula [48] with the compound represented by the general formula [30] in a solvent in the presence of a base.

This reaction is conducted ordinarily at 0 to 150° C. for 10 minutes to 24 hours.

With respect to the amounts of the reagents used in the reaction, the amount of the base is desirably 1 to 1.2 equivalents per 1 equivalent of the present invention compound represented by the general formula [48] but can be varied appropriately depending upon the conditions of the reaction.

As the base and solvent used, there can be mentioned the same substances as used in the production process 3.

[Production Process 7]

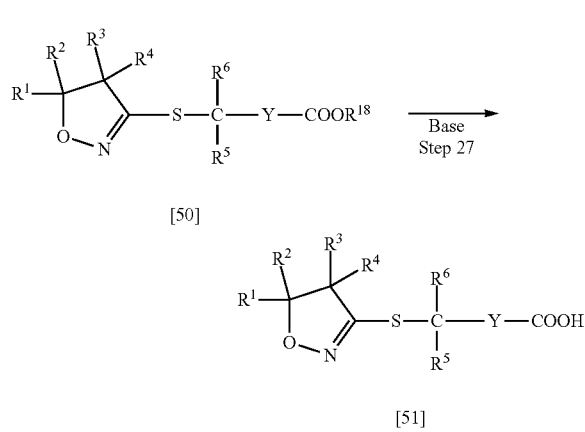

[50]

[51]

wherein Y, $R^1$, $R^2$, $R^3$, $R^4$, $R^5$, $R^6$ and α have the same meanings as given above; $R^{18}$ is an alkyl group, an optionally substituted benzyl group or an optionally substituted phenyl group; and Y may be substituted with 1 to 5 same or different groups selected from the substituent group α.

(Step 27)

A compound of the present invention represented by the general formula [51] can be produced by hydrolyzing a compound of the present invention represented by the general formula [50] in water or a water/solvent mixture in the presence or absence of a base.

This reaction is conducted ordinarily at 0 to 100° C. for 10 minutes to 24 hours.

With respect to the amounts of the reagents used in the reaction, the amount of the base, when used, is desirably 1 to 2 equivalents per 1 equivalent of the present invention compound represented by the general formula [50] but can be varied appropriately depending upon the conditions of the reaction.

As the base used, there can be mentioned, for example, inorganic bases such as potassium carbonate, sodium hydride, sodium hydroxide and the like; and organic bases such as 1,8-diazabicyclo[5.4.0]-7-undecene and the like.

As the solvent to be mixed with water, there can be mentioned, for example, alcohols such as methanol, ethanol and the like; ethers such as tetrahydrofuran and the like; ketones such as acetone, methyl isobutyl ketone and the like; amides such as N,N-dimethylformamide and the like; sulfur compounds such as dimethyl sulfoxide, sulfolane and the like; nitriles such as acetonitrile and the like; and mixtures thereof.

[Production Process 8]

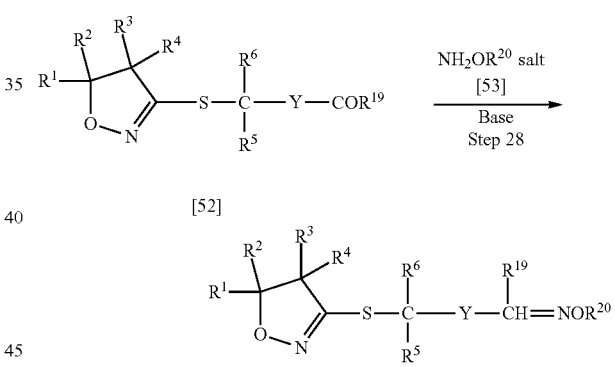

[52]

[54]

wherein Y, $R^1$, $R^2$, $R^3$, $R^4$, $R^5$, $R^6$ and α have the same meanings as given above; $R^{19}$ is a hydrogen atom or an alkyl group; $R^{20}$ is an alkyl group; and Y may be substituted with 1 to 5 same or different groups selected from the substituent group α.

(Step 28)

A compound of the present invention represented by the general formula [54] can be produced by reacting a compound of the present invention represented by the general formula [52] with a compound represented by the general formula [53] in a solvent in the presence of a base.

This reaction is conducted ordinarily at 0 to 100° C. for 10 minutes to 24 hours.

With respect to the amounts of the reagents used in the reaction, it is desired that the amount of the compound represented by the general formula [53] is 1 to 5 equivalents and the amount of the base is 1 to 10 equivalents, all relative to 1 equivalent of the compound of the present invention represented by the general formula [52], but these amounts may be varied appropriately depending upon the conditions of the reaction.

As the base used, there can be mentioned, for example, metal carbonates such as potassium carbonate, sodium carbonate and the like; metal acetates such as potassium acetate, sodium acetate and the like; and organic bases such as triethylamine, dimethylamine, 1,8-diazabicyclo[5.4.0]-7-undecene and the like.

As the salt of $NH_2OR^{20}$ used, there can be mentioned $NH_2OR^{20}$ hydrochloride, $NH_2OR^{20}$ sulfate, etc.

As the solvent used, there can be mentioned, for example, alcohols such as methanol, ethanol and the like; ethers such as tetrahydrofuran and the like; amides such as N,N-dimethylformamide and the like; water; and mixtures thereof.

[Production Process 9]

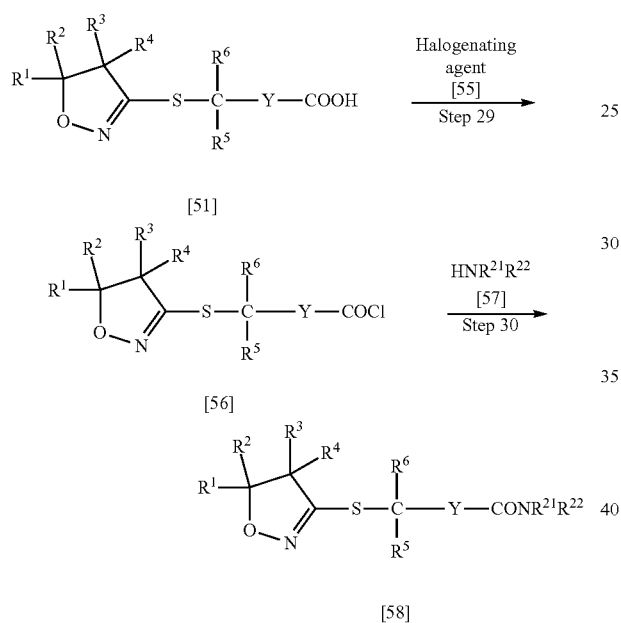

[51]

[56]

[58]

wherein Y, $R^1$, $R^2$, $R^3$, $R^4$, $R^5$, $R^6$ and α have the same meanings as given above; $R^{21}$ and $R^{22}$ are each a hydrogen atom or an alkyl group; and Y may be substituted with 1 to 5 same or different groups selected from the substituent group α.

(Steps 29 and 30)

A compound of the present invention represented by the general formula [58] can be produced by reacting the present invention compound represented by the general formula [51] with a halogenating agent in the presence or absence of a solvent to produce a compound of the present invention represented by the general formula [56] (step 29) and then reacting the compound represented by the general formula [56] with a compound represented by the general formula [57] in the presence or absence of a solvent (step 30).

The reaction of the step 29 is conducted ordinarily at 0 to 100° C. for 10 minutes to 24 hours.

With respect to the amounts of the regents used in the reaction, the amount of the halogenating agent is desired to be 1 to 100 equivalents per 1 equivalent of the present invention compound represented by the general formula [51], but may be varied appropriately depending upon the conditions of the reaction.

As the halogenating agent used, there can be mentioned, for example, thionyl chloride, oxalyl chloride, etc.

As the solvent used, there can be mentioned, for example, halogenated hydrocarbons such as dichloromethane, chloroform and the like; ethers such as diethyl ether, tetrahydrofuran and the like; and aromatic hydrocarbons such as benzene, toluene and the like.

The reaction of the step 30 is conducted ordinarily at 0 to 100° C. for 10 minutes to 24 hours.

With respect to the amounts of the regents used in the reaction, the amount of the compound represented by the general formula [57] is desired to be 2 to 100 equivalents per 1 equivalent of the present invention compound represented by the general formula [56], but may be varied appropriately depending upon the conditions of the reaction.

As the solvent used, there can be mentioned, for example, the same solvents as used in the step 29.

[Production Process 10]

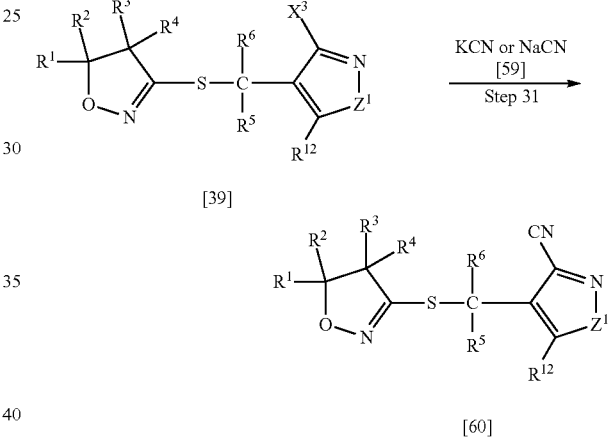

[39]

[60]

wherein $Z^1$, $R^1$, $R^2$, $R^3$, $R^4$, $R^5$, $R^6$, $R^{12}$ and $X^3$ have the same meanings as given above.

A compound of the present invention represented by the general formula [60] can be produced by reacting the present invention compound represented by the general formula [39] with a compound represented by the general formula [59] in a solvent.

This reaction is conducted ordinarily at 0 to 100° C. for 10 minutes to 24 hours.

With respect to the amounts of the regents used in the reaction, the amount of the compound represented by the general formula [59] is desired to be 1 to 2 equivalents per 1 equivalent of the present invention compound represented by the general formula [39], but may be varied appropriately depending upon the conditions of the reaction.

As the solvent used, there can be mentioned, for example, ethers such as dioxane, tetrahydrofuran and the like; halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; ketones such as acetone, 2-butanone and the like; nitriles such as acetonitrile and the like; water; and mixtures thereof.

[Production Process 11]

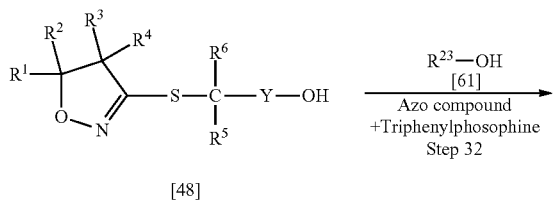

[48]

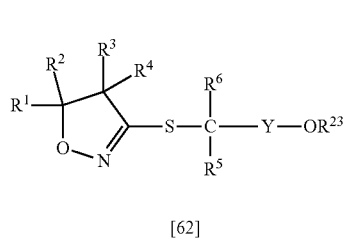

[62]

wherein Y, $R^1$, $R^2$, $R^3$, $R^4$, $R^5$, $R^6$ and α have the same meanings as given above; $R^{23}$ is an alkyl group, a haloalkyl group, a cycloalkyl group, a cycloalkylalkyl group, an alkenyl group, an alkynyl group, an alkoxycarbonylalkyl group, an optionally substituted heteroalkyl group or an optionally substituted benzyl group; and Y may be substituted with 1 to 5 same or different groups selected from the substituent group α.

(Step 32)

A compound of the present invention represented by the general formula [62] can be produced by a known method (Synthesis, 1981, 1-28) of reacting the present invention compound represented by the general formula [48] with a compound represented by the general formula [61] in the presence of an azo compound and triphenylphosphine.

This reaction is conducted ordinarily at 0 to 100° C. for 10 minutes to 24 hours.

With respect to the amounts of the reagents used in the reaction, it is desired that the amount of the compound represented by the general formula [61] is 1 to 1.5 equivalents, the amount of the azo compound is 1 to 1.5 equivalents and the amount of triphenylphosphine is 1 to 1.5 equivalents, all relative to 1 equivalent of the present invention compound represented by the general formula [48], but these amounts can be varied appropriately depending upon the conditions of the reaction.

As the solvent used, there can be mentioned, for example, ethers such as dioxane, tetrahydrofuran and the like; halogenated hydrocarbons such as dichloroethane, carbon tetrachloride, chlorobenzene, dichlorobenzene and the like; amides such as N,N-dimethylacetamide, N,N-dimethylformamide, N-methyl-2-pyrrolidinone and the like; sulfur compounds such as dimethyl sulfoxide, sulfolane and the like; aromatic hydrocarbons such as benzene, toluene, xylene and the like; nitriles such as acetonitrile and the like; and mixtures thereof.

As the azo compound used, there can be mentioned, for example, diethyl azodicarboxylate and diisopropyl azodicarboxylate.

[Production Process 12]

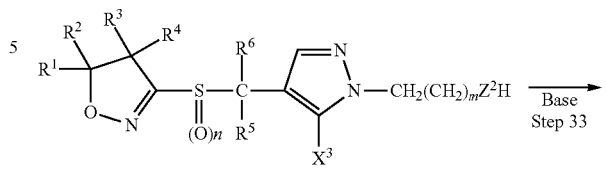

[63]

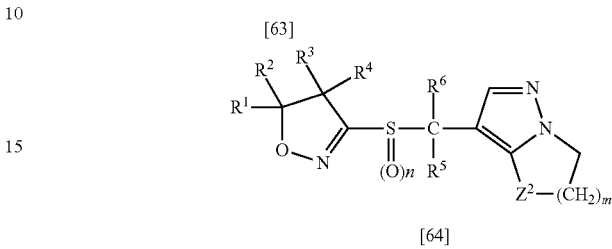

[64]

wherein $X^3$, n, $R^1$, $R^2$, $R^3$, $R^4$, $R^5$, $R^6$, $R^{10}$ and α have the same meanings as given above; $Z^2$ is an oxygen atom, a sulfur atom or N—$R^{17}$; $R^{17}$ is a hydrogen atom or $R^{10}$, m is an integer of 1 to 4; and the carbon atom at the 3-position of the pyrazole ring may be substituted with a group selected from the substituent group α.

(Step 33)

A compound of the present invention represented by the general formula [64] can be produced by reacting a compound of the present invention represented by the general formula [63] in a solvent in the presence of a base.

This reaction is conducted ordinarily at 0 to 100° C. for 10 minutes to 24 hours.

With respect to the amounts of the reagents used in the reaction, the amount of the base is desirably 1 to 3 equivalents per 1 equivalent of the present invention compound represented by the general formula [63], but may be varied appropriately depending upon the conditions of the reaction.

As the base and solvent used, there can be mentioned the same bases and solvents as used in the production process 3.

Next, the process for production of the present invention compound, the method for formulation of the present invention herbicide, and the application of the present herbicide are described specifically by way of examples. Incidentally, description is also made on the process for production of an intermediate for the present invention compound.

EXAMPLE 1

Production of 3-(5-chloro-1-methyl-3-trifluoromethyl-1H-pyrazol-4-ylmethylthio)-5-chloromethyl-5-methyl-2-isoxazoline (present invention compound No. 1)

1.2 g (15.0 mmoles) of sodium hydrosulfide hydrate (purity: 70%) was added into a solution of 2.1 g (10.0 mmoles) of 5-chloromethyl-5-methyl-3-methylsulfonyl-2-isoxazoline dissolved in 20 ml of N,N-dimethylformamide. The mixture was stirred for 2 hours. Then, there were added 2.1 g (15.0 mmoles) of anhydrous potassium carbonate, 2.3 g (15.0 mmoles) of Rongalit and 2.8 g (10.0 mmoles) of 4-bromomethyl-5-chloro-1-methyl-3-trifluoromethyl-1H-pyrazole. The mixture was stirred at room temperature for 2 hours to give rise to a reaction. After the completion of the reaction, the reaction mixture was poured into water and extraction with ethyl acetate was conducted. The resulting organic layer was washed with an aqueous sodium chloride solution, followed by drying over anhydrous magnesium sulfate. The resulting solution was subjected to reduced pressure distillation to remove the solvent contained therein. The residue was purified by silica gel column chromatography to obtain 3.3 g (yield: 100.0%) of 3-(5-chloro-1-methyl-3-trifluoromethyl-1H-pyrazol-4-ylmethylthio)-5-chloromethyl-5-methyl-2-isoxazoline.

EXAMPLE 2

Production of 3-(5-chloro-1-methyl-3-trifluoromethyl-1H-pyrazol-4-ylmethylsulfonyl)-5-chloromethyl-5-methyl-2-isoxazoline (present invention compound No. 2)

4.3 g (25.0 mmoles) of m-chloroperbenzoic acid (70%) was added, with ice-cooling, into a solution of 3.3 g (10.0 mmoles) of 3-(5-chloro-1-methyl-3-trifluoromethyl-1H-pyrazol-4-ylmethylthio)-5-chloromethyl-5-methyl-2-isoxazoline dissolved in 20 ml of chloroform. The mixture was stirred at room temperature for 20 hours to give rise a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride ride solution in this order and then dried over anhydrous magnesium sulfate. The resulting solution was subjected to reduced pressure distillation to remove the solvent contained therein. The resulting crystals were washed with hexane to obtain 2.8 g (yield: 76.0%) of a white powder (melting point: 114 to 116° C.) of 3-(5-chloro-1-methyl-3-trifluoromethyl-1H-pyrazol-4-ylmethylsulfonyl)-5-chloromethyl-5-methyl-2-isoxazoline.

$^1$H-NMR [CDCl$_3$/TMS, δ (ppm)]: 4.63 (2H, s), 3.96 (3H, s), 3.62 (2H, q), 3.32 (2H, ABq, J=13.4, Δv=164.1 Hz), 1.63 (3H, s)

EXAMPLE 3

Production of 3-(1-tert-butyl-5-chloro-3-trifluoromethyl-1H-pyrazol-4-ylmethylthio)-5-chloromethyl-5-methyl-2-isoxazoline (present invention compound No. 3)

Into a solution of 24.2 g (70.9 mmoles) of (1-tert-butyl-5-chloro-3-trifluoromethyl-1H-pyrazol-4-yl)-methane-thiol dissolved in 20 ml of N,N-dimethylformamide were added 11.8 g (85.0 mmoles) of anhydrous potassium carbonate and 20 ml of a N,N-dimethylformamide solution containing 2.1 g (10.0 mmoles) of 5-chloromethyl-5-methyl-3-methylsulfonyl-2-isoxazoline. The mixture was stirred overnight to give rise to a reaction. After the completion of the reaction, the reaction mixture was poured into water and extraction with ethyl acetate was conducted. The resulting organic layer was washed with water and then dried over anhydrous magnesium sulfate. The resulting solution was filtered and the filtrate was subjected to reduced pressure distillation to remove the solvent contained therein. The residue was purified by silica gel column chromatography to obtain 23.1 g (yield: 80.5%) of a colorless viscous liquid (n$_D^{20}$=1.5051) of 3-(1-tert-butyl-5-chloro-3-trifluoromethyl-1H-pyrazol-4-ylmethylthio)-5-chloromethyl-5-methyl-2-isoxazoline.

$^1$H-NMR [CDCl$_3$/TMS, δ (ppm)]: 4.24 (2H, s), 3.55 (2H, q), 3.02 (2H, ABq, J=16.7, Δv=110.5 Hz), 1.71 (9H, s), 1.57 (3H, s)

EXAMPLE 4

Production of 3-(5-chloro-3-trifluoromethyl-1H-pyrazol-4-ylmethylthio)-5-chloromethyl-5-methyl-2-isoxazoline (present invention compound No. 4)

Into 100 ml of an acetic acid solution of 25% hydrobromic acid was added 22.0 g (54.4 mmoles) of 3-(1-tert-butyl-5-chloro-3-trifluoromethyl-1H-pyrazol-4-ylmethylthio)-5-chloromethyl-5-methyl-2-isoxazoline. The mixture was stirred at room temperature for 2 hours and at 40° C. for 1 hour to give rise to a reaction. After the completion of the reaction, the reaction mixture was poured into water and extraction with ethyl acetate was conducted. The resulting organic layer was washed with water and then dried over anhydrous magnesium sulfate. The resulting solution was filtered and the filtrate was subjected to reduced pressure distillation to remove the solvent contained therein. The resulting crystals were washed with hexane to obtain 17.7 g (yield: 93.7%) of a milky white powder (melting point: 105 to 107° C.) of 3-(5-chloro-3-trifluoromethyl-1H-pyrazol-4-ylmethylthio)-5-chloromethyl-5-methyl-2-isoxazoline.

$^1$H-NMR [CDCl$_3$/TMS, δ (ppm)]: 4.26 (2H, s), 3.56 (2H, q), 3.03 (2H, ABq, J=16.7, Δv=111.8 Hz), 1.56 (3H, s)

EXAMPLE 5

Production of 3-(1-ethyl-5-chloro-3-trifluoromethyl-1H-pyrazol-4-ylmethylthio)-5-chloromethyl-5-methyl-2-isoxazoline (present invention compound No. 5) and 3-(1-ethyl-3-chloro-5-trifluoromethyl-1H-pyrazol-4-ylmethylthio)-5-chloromethyl-5-methyl-2-isoxazline (present invention compound No. 6)

0.6 g (4.3 mmoles) of anhydrous potassium carbonate and 0.74 g (4.7 mmoles) of ethyl iodide were added into a solution of 1.5 g (4.3 mmoles) of 3-(5-chlorotrifluoromethyl-1H-pyrazol-4-ylmethylthio)-5-chloromethyl-5-methyl-2-isoxazoline dissolved in 25 ml of N,N-dimethylformamide. The mixture was stirred at room temperature for 5 hours to give rise to a reaction. After confirmation of the completion of the reaction, the reaction mixture was poured into water and extraction with ethyl acetate was conducted. The resulting organic layer was washed with an aqueous citric acid solution and a saturated aqueous sodium chloride solution and then dried over anhydrous magnesium sulfate. The resulting solution was filtered and the filtrate was subjected to reduced pressure distillation to remove the solvent contained therein. The residue was purified by silica gel column chromatography to obtain 0.91 g (yield: 56.0%) of 3-(1-ethyl-5-chloro-3-trifluoromethyl-1H-pyrazol-4-ylmethylthio)-5-chloromethyl-5-methyl-2-isoxazoline and 0.45 g (yield: 28.0%) of 3-(1-ethyl-3-chloro-5-trifluoromethyl-1H-pyrazol-4-ylmethylthio)-5-chloromethyl-5-methyl-2-isoxazline.

EXAMPLE 6

Production of 3-(1-ethyl-5-chloro-3-trifluoromethyl-1H-pyrazol-4-ylmethylsulfonyl)-5-chloromethyl-5-methyl-2-isoxazoline (present invention compound No. 7)

1.31 g (5.3 mmoles) of m-chloroperbenzoic acid (70%) was added, with ice-cooling, into a solution of 0.91 g (2.4 mmoles) of 3-(1-ethyl-5-chloro-3-trifluoromethyl-1H-pyrazol-4-ylmethylthio)-5-chloromethyl-5-methyl-2-isoxazoline dissolved in 40 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with diisopropyl ether to obtain 0.81 g (yield: 82.0%) of a white powder (melting point: 123 to 124° C.) of 3-(1-ethyl-5-chloro-3-trifluoromethyl-1H-pyrazol-4-ylmethylsulfonyl)-5-chloromethyl-5-methyl-2-isoxazoline.

$^1$H-NMR [CDCl$_3$/TMS, δ (ppm)]: 4.64 (2H, s), 4.29 (2H, q), 3.62 (2H, q), 3.30 (2H, ABq, J=17.8, Δv=125.6 Hz), 1.55-1.50 (6H, m)

EXAMPLE 7

Production of 3-(4-ethoxy-6-trifluoromethylpyrimidin-5-ylmethylthio)-5-chloromethyl-5-methyl-2-isoxazoline (present invention compound No. 8)

3.4 g (42.3 mmoles) of sodium hydrosulfide hydrate (purity: 70%) was added into a solution of 4.6 g (21.6 mmoles) of 3-methylsulfonyl-5-chloromethyl-5-methyl-2-isoxazoline dissolved in 70 ml of DMF. The mixture was stirred for 2 hours. Then, there were added 3.0 g (21.6 mmoles) of potassium carbonate, 3.3 g (21.6 mmoles) of Rongalit and 5-bromomethyl-4-ethoxy-6-trifluoromethylpyrimidine. The mixture was stirred at room temperature for 21 hours to give rise to a reaction. After the completion of the reaction, the reaction mixture was poured into water and extraction with ethyl acetate was conducted. The resulting organic layer was washed with an aqueous sodium chloride solution, followed by drying over anhydrous magnesium sulfate. The resulting solution was subjected to reduced pressure distillation to remove the solvent contained therein. The residue was purified by silica gel column chromatography (solvent system: hexane-ethyl acetate) to obtain 1.9 g (yield: 30.3%) of 3-(4-ethoxy-6-trifluoromethylpyrimidin-5-ylmethylthio)-5-chloromethyl-5-methyl-2-isoxazoline.

$^1$H-NMR [CDCl$_3$/TMS, δ (ppm)]: 8.78 (1H, s), 4.57 (2H, q), 4.45 (2H, s), 3.57 (2H, q), 3.03 (2H, ABq, J=16.8, Δv=114.3 Hz), 1.58 (3H, s), 1.45 (3H, t)

EXAMPLE 8

Production of 3-(4-ethoxy-6-trifluoromethylpyrimidin-5-ylmethylsulfonyl)-5-chloromethyl-5-methyl-2-isoxazoline (present invention compound No. 9)

3.2 g (12.9 mmoles) of m-chloroperbenzoic acid (70%) was added, with ice-cooling, into a solution of 1.9 g (5.1 mmoles) of 3-(4-ethoxy-6-trifluoromethylpyrimidin-5-ylmethylthio)-5-chloromethyl-5-methyl-2-isoxazoline dissolved in 30 ml of chloroform. The mixture was stirred at room temperature for 5 hours to give rise to a reaction. After the completion of the reaction, the reaction mixture was poured into water and extraction with chloroform was conducted. The resulting organic layer was washed with an aqueous sodium hydrogensulfite solution, an aqueous sodium hydrogencarbonate solution, and an aqueous sodium chloride solution in this order and then dried over anhydrous magnesium sulfate. The resulting solution was subjected to reduced pressure distillation to remove the solvent contained therein. The resulting crystals were washed with hexane to obtain 1.8 g (yield: 87.7%) of white crystals (melting point: 76.0 to 78.0° C.) of 3-(4-ethoxy-6-trifluoromethylpyrimidin-5-ylmethylsulfonyl)-5-chloromethyl-5-methyl-2-isoxazoline.

$^1$H-NMR [CDCl$_3$/TMS, δ (ppm)]: 8.87 (1H, s), 5.03 (2H, s), 4.59 (2H, q), 3.64 (2H, q), 3.33 (2H, ABq, J=17.7, Δv=125.9 Hz), 1.64 (3H, s), 1.46 (3H, t)

EXAMPLE 9

Production of 5-chloromethyl-3-(1-ethyl-5-fluoro-3-trifluoromethyl-1H-pyrazol-4-ylmethylthio)-5-methyl-2-isoxazoline (present invention compound No. 10)

6.9 g (85.8 mmoles) of sodium hydrosulfide hydrate (purity: 70%) was added, at room temperature, into a solution of 9.1 g (42.9 mmoles) of 5-chloromethyl-5-methyl-3-methylsulfonyl-2-isoxazoline dissolved in 50 ml of N,N-dimethylformamide. The mixture was stirred for 2 hours. Then, there were added 5.9 g (42.9 mmoles) of anhydrous potassium carbonate, 6.6 g (42.9 mmoles) of Rongalit and the crude product of 4-bromomethyl-1-ethyl-5-fluoro-3-trifluoromehtyl-1H-pyrazole (equivalent to 42.9 mmoles) obtained in Reference Example 20. The mixture was stirred at room temperature for 30 minutes to give rise to a reaction. After the completion of the reaction, the reaction mixture was poured into water and extraction with ethyl acetate was conducted. The resulting organic layer was washed with water and then dried over anhydrous magnesium sulfate. The resulting solution was subjected to reduced pressure distillation to remove the solvent contained therein. The residue was purified by silica gel column chromatography to obtain 10.3 g (yield: 66.9%) of 5-chloromethyl-3-(1-ethyl-5-fluoro-3-trifluoromethyl-1H-pyraz-ol-4-ylmethylthio)-5-methyl-2-isoxazoline.

$^1$H-NMR [CDCl$_3$/TMS, δ (ppm)]: 4.15-4.08 (4H, m), 3.54 (2H, q), 3.01 (2H, ABq, J=16.7, Δv=110.8 Hz), 1.55 (3H, s), 1.47 (3H, t)

EXAMPLE 10

Production of 5-chloromethyl-3-(1-ethyl-5-fluoro-3-trifluoromethyl-1H-pyrazol-4-ylmethylsulfonyl)-5-methyl-2-isoxazoline (present invention compound No. 11)

1.23 g (5.0 mmoles) of m-chloroperbenzoic acid (purity: 70%) was added, with ice-cooling, into a solution of 0.72 g (2.0 mmoles) of 5-chloromethyl-3-(1-ethyl-5-fluoro-3-trifluoromethyl-1H-pyrazol-4-ylmethylthio)-5-methyl-2-isoxazoline dissolved in 10 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with n-hexane to obtain 0.64 g (yield: 82.1%) of a white powder (melting point: 73 to 75° C.) of 5-chloromethyl-3-(1-ethyl-5-fluoro-3-trifluoromethyl-1H-pyrazol-4-ylmethylsulfonyl)-5-methyl-2-isoxazoline.

$^1$H-NMR [CDCl$_3$/TMS, δ (ppm)]: 4.56 (2H, s), 4.17 (2H, q), 3.61 (2H, q), 3.31 (2H, ABq, J=17.8, Δv=123.6 Hz), 1.58 (3H, s), 1.50 (3H, t)

EXAMPLE 11

Production of 5-chloromethyl-3-(1-ethyl-5-methoxy-3-trifluoromethyl-1H-pyrazol-4-ylmethylthio)-5-methyl-2-isoxazoline (present invention compound No. 12)

4.3 g (22.5 mmoles) of sodium methoxide (in the form of a 28% methanol solution) was added, at room temperature, into a solution of 5.4 g (15.0 mmoles) of 5-chloromethyl-3-(1-ethyl-5-fluoro-3-trifluoromethyl-1H-pyrazol-4-ylmethylthio)-5-methyl-2-isoxazoline dissolved in 30 ml of methanol. The mixture was heated for refluxing for 8 hours, to give rise to a reaction. After the completion of the reaction, the reaction mixture was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 3.3 g (yield: 59.1%) of 5-chloromethyl-3-(1-ethyl-5-methoxy-3-trifluoromethyl-1H-pyrazol-4-ylmethylthio)-5-meth-yl-2-isoxazoline.

$^1$H-NMR [CDCl$_3$/TMS, δ (ppm)]: 4.26 (2H, s), 4.06 (5H, m), 3.55 (2H, q), 3.02 (2H, ABq, J=16.9, Δv=110.5 Hz), 1.56 (3H, s), 1.41 (3H, t)

EXAMPLE 12

Production of 5-chloromethyl-3-(1-ethyl-5-methoxy-3-trifluoromethyl-1H-pyrazol-4-ylmethylsulfonyl)-5-methyl-2-isoxazoline (present invention compound No. 13)

1.24 g (5.0 mmoles) of m-chloroperbenzoic acid (purity: 70%) was added, with ice-cooling, into a solution of 0.74 g (2.0 mmoles) of 5-chloromethyl-3-(1-ethyl-5-methoxy-3-trifluoromethyl-1H-pyrazol-4-ylmethylthio)-5-methyl-2-isoxazoline dissolved in 10 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with n-hexane to obtain 0.72 g (yield: 89.2%) of a white powder (melting point: 139 to 140° C.) of 5-chloromethyl-3-(1-ethyl-5-methoxy-3-trifluoromethyl-1H-pyrazol-4-ylmethylsulfonyl)-5-methyl-2-isoxazoline.

$^1$H-NMR [CDCl$_3$/TMS, δ (ppm)]: 4.60 (2H, s), 4.13-4.06 (5H, m), 3.30 (2H, ABq, J=17.8, Δv=122.8 Hz), 1.58 (3H, s), 1.46 (3H, t)

EXAMPLE 13

Production of 5-chloromethyl-3-(1-ethyl-5-methylthio-3-trifluoromethyl-1H-pyrazol-4-ylmethylthio)-5-methyl-2-isoxazoline (present invention compound No. 14)

4.21 g (9.0 mmoles) of sodium methyl thioalcoholate (in the form of a 15% aqueous solution) was added, at room temperature, into a solution of 1.08 g (3.0 mmoles) of 5-chloromethyl-3-(1-ethyl-5-fluoro-3-trifluoromethyl-1H-pyrazol-4-ylmethylthio)-5-methyl-2-isoxazoline dissolved in 10 ml of N,N-dimethylformamide. The mixture was stirred at room temperature overnight to give rise to a reaction. After the completion of the reaction, the reaction mixture was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein to obtain a crude product of 5-chloromethyl-3-(1-ethyl-5-methylthio-3-trifluoromethyl-1H-pyrazol-4-ylmethylthio)-5-methyl-2-isoxazoline.

EXAMPLE 14

Production of 5-chloromethyl-3-(1-ethyl-5-methylsulfonyl-3-trifluoromethyl-1H-pyrazol-4-ylmethylsulfonyl)-5-methyl-2-isoxazoline (present invention product No. 15)

3.74 g (15.0 mmoles) of m-chloroperbenzoic acid (purity: 70%) was added, with ice-cooling, into a solution of a crude product of 5-chloromethyl-3-(1-ethyl-5-methylthio-3-trifluoromethyl-1H-pyrazol-4-ylmethylthio)-5-methyl-2-isoxazoline (equivalent to 3.0 mmoles) dissolved in 30 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with n-hexane to obtain 1.15 g (yield: 84.8%) of a white powder (melting point: 113 to 114° C.) of 5-chloromethyl-3-(1-ethyl-5-methylsulfonyl-3-trifluoromethyl-1H-pyrazol-4-ylmethylsulfonyl)-5-methyl-2-isoxazoline.

$^1$H-NMR [CDCl$_3$/TMS, δ (ppm)]: 5.08 (2H, bR), 4.60 (2H, q), 3.64 (2H, q), 3.41 (3H, s), 3.36 (2H, ABq, J=17.5, Δv=163.1 Hz), 1.65 (3H, s), 1.60 (3H, t)

EXAMPLE 15

Production of 5-chloromethyl-3-(5-cyano-1-ethyl-3-trifluoromethyl-1H-pyrazol-4-ylmethylthio)-5-methyl-2-isoxazoline (present invention product No. 16)

0.30 g (6.0 mmoles) of sodium cyanide was added, at room temperature, into a solution of 1.08 g (3.0 mmoles) of 5-chloromethyl-3-(1-ethyl-5-fluoro-3-trifluoromethyl-1H-pyrazol-4-ylmethylthio)-5-methyl-2-isoxazoline dissolved in 10 ml of N,N-dimethylformamide. The mixture was stirred at 50° C. for 10 hours to give rise to a reaction. After the completion of the reaction, the reaction mixture was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 1.10 g (yield: quantitative) of 5-chloromethyl-3-(5-cyano-1-ethyl-3-trifluoromethyl-1H-pyrazol-4-ylmethylthio)-5-methyl-2-isoxazoline.

EXAMPLE 16

Production of 5-chloromethyl-3-(5-cyano-1-ethyl-3-trifluoromethyl-1H-pyrazol-4-ylmethylsulfonyl)-5-methyl-2-isoxazoline (present invention product No. 17)

1.85 g (7.5 mmoles) of m-chloroperbenzoic acid (purity: 70%) was added, with ice-cooling, into a solution of 1.10 g (3.0 mmoles) of 5-chloromethyl-3-(5-cyano-1-ethyl-3-trifluoromethyl-1H-pyrazol-4-ylmethylthio)-5-methyl-2-isoxazoline dissolved in 20 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with n-hexane to obtain 1.15 g (yield: 84.8%) of a white powder (melting point: 76 to 78° C.) of 5-chloromethyl-3-(5-cyano-1-ethyl-3-trifluoromethyl-1H-pyrazol-4-ylmethylsulfonyl)-5-methyl-2-isoxazoline.

$^1$H-NMR [CDCl$_3$/TMS, δ (ppm)]: 4.73 (2H, s), 4.45 (2H, q), 3.62 (2H, q), 3.35 (2H, ABq, J=17.6, Δv=129.6 Hz), 1.59-1.46 (6H, m)

EXAMPLE 17

Production of 5-chloromethyl-3-(1-ethyl-5-hydroxy-3-trifluoromethyl-1H-pyrazol-4-ylmethylthio)-5-methyl-2-isoxazoline (present invention compound No. 18)

10 ml of boron tribromide (2 M/liter of dichloromethane solution, 20.2 mmoles) was added, at –60° C., into a solution of 2.5 g (6.7 mmoles) of 5-chloromethyl-3-(1-ethyl-5-methoxy-3-trifluoromethyl-1H-pyrazol-4-ylmethylthio)-5-methyl-2-isoxazoline dissolved in 30 ml of dichloromethane. The mixture was stirred at room temperature overnight to give rise to a reaction. After the completion of the reaction, the reaction mixture was poured into ice water and extraction with chloroform was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 1.6 g (yield: 66.7%) of 5-chloromethyl-3-(1-ethyl-5-hydroxy-3-trifluoromethyl-1H-pyrazol-4-ylmethylthio)-5-methyl-2-isoxazoline.

EXAMPLE 18

Production of 5-chloromethyl-3-(5-ethoxy-1-ethyl-3-trifluoromethyl-1H-pyrazol-4-ylmethylthio)-5-methyl-2-isoxazoline (present invention product No. 19)

0.3 g (5.4 mmoles) of ethanol and 1.4 g (5.4 mmoles) of triphenylphosphine were added, at room temperature, into a solution of 1.6 g (4.5 mmoles) of 5-chloromethyl-3-(1-ethyl-5-hydroxy-3-trifluoromethyl-1H-pyrazol-4-ylmethylthio)-5-meth-yl-2-isoxazoline dissolved in 20 ml of tetrahydrofuran. Thereto was added, with ice-cooling, 1.1 g (5.4 mmoles) of diisopropyl azodicarboxylate. The mixture was stirred for 1 hour to give rise to a reaction. After the completion of the reaction, the reaction mixture was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 1.5 g (yield: 86.8%) of 5-chloromethyl-3-(5-ethoxy-1-ethyl-3-trifluoromethyl-1H-pyrazol-4-ylmethylthio)-5-methyl-2-isoxazoline.

EXAMPLE 19

Production of 5-chloromethyl-3-(5-ethoxy-1-ethyl-3-trifluoromethyl-1H-pyrazol-4-ylmethylsulfonyl)-5-methyl-2-isoxazoline (present invention product No. 20)

2.4 g (9.7 mmoles) of m-chloroperbenzoic acid (purity: 70%) was added, with ice-cooling, into a solution of 1.5 g (3.9 mmoles) of 5-chloromethyl-3-(5-ethoxy-1-ethyl-3-trifluoromethyl-1H-pyrazol-4-ylmethylthio)-5-methyl-2-isoxazoline dissolved in 10 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with diisopropyl ether to obtain 0.71 g (yield: 43.8%) of a white powder (melting point: 67 to 69° C.) of 5-chloromethyl-3-(5-ethoxy-1-ethyl-3-trifluoromethyl-1H-pyrazol-4-ylmethylsulfonyl)-5-methyl-2-isoxazoline.

$^1$H-NMR [CDCl$_3$/TMS, δ (ppm)]: 4.58 (2H, s), 4.32 (2H, q), 4.09 (2H, q), 3.61 (2H, q), 3.28 (2H, ABq, J=17.8, Δv=121.7 Hz), 1.62 (3H, s), 1.48-1.43 (6H, m)

EXAMPLE 20

Production of 5-chloromethyl-3-(5-fluoro-1-methyl-3-trifluoromethyl-1H-pyrazol-4-ylmethylthio)-5-methyl-2-isoxazoline (present invention compound No. 21)

6.4 g (80.0 mmoles) of sodium hydrosulfide hydrate (purity: 70%) was added, at room temperature, into a solution of 8.5 g (40.0 mmoles) of 5-chloromethyl-5-methyl-3-methylsulfonyl-2-isoxazoline dissolved in 40 ml of N,N-dimethylformamide. The mixture was stirred for 1 hour. Then, there were added, with ice-cooling, 6.6 g (48.0 mmoles) of anhydrous potassium carbonate, 7.4 g (48.0 mmoles) of Rongalit and 10.4 g (40.0 mmoles) of 4-bromomethyl-5-fluoro-1-methyl-3-trifluoromethyl-1H-pyrazole. The mixture was stirred with ice-cooling for 30 minutes, to give rise to a reaction. After the completion of the reaction, the reaction mixture was poured into water and extraction with ethyl acetate was conducted. The resulting organic layer was washed with water and then dried over anhydrous magnesium sulfate. The resulting solution was subjected to reduced pressure distillation to remove the solvent contained therein. The residue was purified by silica gel column chromatography to obtain 11.8 g (yield: 85.5%) of a light yellow viscous liquid (refractive index: $n_D^{20}=1.4974$) of 5-chloromethyl-3-(5-fluoro-1-methyl-3-trifluoromethyl-1H-pyrazol-4-ylmethylthio)-5-methyl-2-iso-xazoline.

$^1$H-NMR [CDCl$_3$/TMS, δ (ppm)]: 4.15 (2H, s), 3.80 (3H, s), 3.54 (2H, q), 3.01 (2H, ABq, J=16.8, Δν=147.8 Hz), 1.53 (3H, s)

EXAMPLE 21

Production of 5-chloromethyl-3-(5-methoxy-1-methyl-3-trifluoromethyl-1H-pyrazol-4-ylmethylthio)-5-methyl-2-isoxazoline (present invention compound No. 22)

0.9 g (4.4 mmoles) of sodium methoxide (in the form of a 28% methanol solution) was added, at room temperature, into a solution of 1.0 g (2.9 mmoles) of 5-chloromethyl-3-(5-fluoro-1-methyl-3-trifluoromethyl-1H-pyrazol-4-ylmethylthio)-5-methyl-2-isoxazoline dissolved in 10 ml of methanol. The mixture was heated for refluxing for 5 hours, to give rise to a reaction. After the completion of the reaction, the reaction mixture was poured into water and extraction with ethyl acetate was conducted. The resulting organic layer was washed with water and an aqueous sodium chloride solution in this order, and then dried over anhydrous magnesium sulfate. The resulting solution was subjected to reduced pressure distillation to remove the solvent contained therein. The residue was purified by silica gel column chromatography to obtain 3.3 g (yield: quantitative) of 5-chloromethyl-3-(5-methoxy-1-methyl-3-trifluoromethyl-1H-pyrazol-4-ylmethylthio)-5-methyl-2-isoxazoline.

$^1$H-NMR [CDCl$_3$/TMS, δ (ppm)]: 4.26 (2H, s), 4.06 (3H, s), 3.72 (3H, s), 3.55 (2H, q), 3.02 (2H, ABq, J=16.7, Δν=111.0 Hz), 1.56 (3H, s)

EXAMPLE 22

Production of 5-chloromethyl-3-(5-hydroxy-1-methyl-3-trifluoromethyl-1H-pyrazol-4-ylmethylthio)-5-methyl-2-isoxazoline (present invention compound No. 23)

28.0 ml of boron tribromide (2 M/liter of a dichloromethane solution, 55.9 mmoles) was added, at 0° C., into a solution of 10.0 g (28.0 mmoles) of 5-chloromethyl-3-(5-methoxy-1-methyl-3-trifluoromethyl-1H-pyrazol-4-ylmethylthio)-5-meth-yl-2-isoxazoline dissolved in 30 ml of dichloromethane. The mixture was stirred at room temperature for 30 minutes to give rise to a reaction. After the completion of the reaction, the reaction mixture was poured into ice water and extraction with ethyl acetate was conducted. The resulting organic layer was washed with water and an aqueous sodium chloride solution in this order, and then dried over anhydrous magnesium sulfate. The resulting solution was subjected to reduced pressure distillation to remove the solvent contained therein. The resulting crystals were washed with n-hexane to obtain 8.4 g (yield: 87.2%) of a light pink powder (melting point: 111 to 112° C.) of 5-chloromethyl-3-(5-hydroxy-1-methyl-3-trifluoromethyl-1H-pyrazol-4-ylmethylthio)-5-methyl-2-iso-xazoline.

$^1$H-NMR [CDCl$_3$/TMS, δ (ppm)]: 4.01 (2H, s), 3.69 (3H, s), 3.55 (2H, q), 3.09 (2H, ABq, J=17.0, Δν=114.4 Hz), 1.56 (3H, s)

EXAMPLE 23

Production of 5-chloromethyl-3-(1-methyl-5-isopropoxy-3-trifluoromethyl-1H-pyrazol-4-ylmethylthio)-5-methyl-2-isoxazoline (present invention compound No. 24)

0.5 g (3.5 mmoles) of anhydrous potassium carbonate was added, at room temperature, into a solution of 1.0 g (2.9 mmoles) of 5-chloromethyl-3-(5-hydroxy-1-methyl-3-trifluoromethyl-1H-pyrazol-4-ylmethylthio)-5-methyl-2-isoxazoline dissolved in 10 ml of N,N-dimethylformamide. Thereto was added, at room temperature, 0.6 g (3.5 mmoles) of isopropyl iodide. The mixture was stirred for 30 minutes to give rise to a reaction. After the completion of the reaction, the reaction mixture was poured into water and extraction with ethyl acetate was conducted. The resulting organic layer was washed with water and an aqueous sodium chloride solution in this order, and then dried over anhydrous magnesium sulfate. The resulting solution was subjected to reduced pressure distillation to remove the solvent contained therein. The residue was purified by silica gel column chromatography to obtain 0.5 g (yield: 45.0%) of 5-chloromethyl-3-(1-methyl-5-isopropoxy-3-trifluoromethyl-1H-pyrazol-4-ylmethylthio)-5-methyl-2-isoxazoline.

EXAMPLE 24

Production of 5-chloromethyl-3-(1-methyl-5-isopropoxy-3-trifluoromethyl-1H-pyrazol-4-ylmethylsulfonyl)-5-methyl-2-isoxazoline (present invention compound No. 25)

0.65 g (2.64 mmoles) of m-chloroperbenzoic acid (purity: 70%) was added, with ice-cooling, into a solution of 0.5 g (1.2 mmoles) of 5-chloromethyl-3-(1-methyl-5-isopropoxy-3-trifluoromethyl-1H-pyrazol-4-ylmethylthio)-5-methyl-2-isoxa-zoline dissolved in 10 ml of chloroform. The mixture was stirred at room temperature for 20 hours to give rise to a reaction. After the completion of the reaction, the reaction mixture was poured into water and extraction with chloroform was conducted. The resulting organic layer was washed with an aqueous sodium hydrogensulfite solution, water, an aqueous sodium hydrogencarbonate solution, water and an aqueous sodium chloride solution in this order and then dried over anhydrous magnesium sulfate. The resulting solution was subjected to reduced pressure distillation to remove the solvent contained therein. The resulting crystals were washed with diisopropyl ether to obtain 0.49 g (yield: 90.0%) of a light yellow viscous liquid of 5-chloromethyl-3-(1-methyl-5-isopropoxy-3-trifluoromethyl-1H-pyrazol-4-ylmethylsulfonyl)-5-methyl-2-isoxazoline.

$^1$H-NMR [CDCl$_3$/TMS, δ (ppm)]: 4.64 (1H, s), 4.51 (2H, s), 3.76 (3H, s), 3.61 (2H, q), 3.24 (2H, ABq, J=17.8, Δν=116.9 Hz), 1.61 (3H, s), 1.40 (6H, d)

The compounds produced based on the methods of Examples 1 to 24 are shown in Tables 58 to 60.

TABLE 58

| Compound No. | Structural formula | Melting point (° C.) or refractive index (nD20) |
| --- | --- | --- |
| 26 | ClCH₂–C(Me)(–O–N=C(–SO₂–CH₂–[pyrazole: 3-CF₃, 5-Cl, 1-CH₂OMe])–CH₂–) (4,5-dihydroisoxazole) | 111-112 |
| 27 | ClCH₂–C(Me)(–O–N=C(–SO₂–CH₂–[pyrazole: 3-CF₃, 5-Cl, 1-Pr-i])–CH₂–) (4,5-dihydroisoxazole) | 130-132 |
| 28 | ClCH₂–C(Me)(–O–N=C(–SO₂–CH₂–[pyrazole: 3-CF₃, 5-Cl, 1-Bu-t])–CH₂–) (4,5-dihydroisoxazole) | 122-124 |
| 29 | ClCH₂–C(Me)(–O–N=C(–SO₂–CH₂–[pyrazole: 3-Cl, 5-CF₃, 1-Et])–CH₂–) (4,5-dihydroisoxazole) | 122-123 |
| 30 | ClCH₂–C(Me)(–O–N=C(–SO₂–CH₂–[pyrazole: 3-Cl, 5-CF₃, 1-Pr-i])–CH₂–) (4,5-dihydroisoxazole) | 155-156 |
| 31 | ClCH₂–C(Me)(–O–N=C(–SO₂–CH₂–[pyrazole: 3-Cl, 5-CF₃, 1-CHF₂])–CH₂–) (4,5-dihydroisoxazole) | 117-118 |
| 32 | ClCH₂–C(Me)(–O–N=C(–SO₂–CH₂–[pyrazole: 3-CF₃, 5-Cl, 1-CHF₂])–CH₂–) (4,5-dihydroisoxazole) | 137-138 |

TABLE 58-continued

| Compound No. | Structural formula | Melting point (° C.) or refractive index (nD20) |
| --- | --- | --- |
| 33 | ClCH₂–C(Me)(–O–N=C(–SO₂–CH₂–[pyrazole: 3-Cl, 5-CF₃, 4-linked, N1-CH₂OMe])–CH₂–) (isoxazoline) | 114-116 |
| 34 | ClCH₂–C(Me)(–O–N=C(–SO₂–CH₂–[pyrazole: 3-Cl, 5-CF₃, 4-linked, N1-CH₂Pr-c])–CH₂–) (isoxazoline) | 125-126 |
| 35 | ClCH₂–C(Me)(–O–N=C(–SO₂–CH₂–[pyrazole: 3-CF₃, 5-Cl, 4-linked, N1-CH₂Pr-c])–CH₂–) (isoxazoline) | 77-78 |

TABLE 59

| Compound No. | Structural formula | Melting point (° C.) or refractive index (nD20) |
| --- | --- | --- |
| 36 | ClCH₂–C(Me)(–O–N=C(–SO₂–CH₂–[pyrazole: 3-Cl, 5-CF₃, 4-linked, N1-CH₂C≡CH])–CH₂–) (isoxazoline) | 114-115 |
| 37 | ClCH₂–C(Me)(–O–N=C(–SO₂–CH₂–[pyrazole: 3-CF₃, 5-Cl, 4-linked, N1-CH₂C≡CH])–CH₂–) (isoxazoline) | 125-126 |
| 38 | ClCH₂–C(Me)(–O–N=C(–SO₂–CH₂–[pyrazole: 3-CF₃, 5-F, 4-linked, N1-Me])–CH₂–) (isoxazoline) | 1.4828 |

TABLE 59-continued

| Compound No. | Structural formula | Melting point (° C.) or refractive index (nD20) |
|---|---|---|
| 39 | ClCH₂―[5-Me,5-(isoxazoline)]―SO₂―CH₂―[pyrazole: 3-CF₃, 5-CN, 1-Me] | 77-79 |
| 40 | ClCH₂―[5-Me,5-(isoxazoline)]―SO₂―CH₂―[pyrazole: 3-CF₃, 5-OMe, 1-Me] | 139-140 |
| 41 | ClCH₂―[5-Me,5-(isoxazoline)]―SO₂―CH₂―[cyclopenta-fused pyrazole, N-CHF₂] | 101-103 |
| 42 | ClCH₂―[5-Me,5-(isoxazoline)]―SO₂―CH₂―[pyrazole: 5-CF₃, 3-Cl, 1-Me] | 123-124 |
| 43 | ClCH₂―[5-Me,5-(isoxazoline)]―SO₂―CH₂―[pyrazole: 3-CF₃, 5-OEt, 1-Me] | 106-107 |
| 44 | ClCH₂―[5-Me,5-(isoxazoline)]―SO₂―CH₂―[pyrazole: 3-CF₃, 5-O-n-Pr, 1-Me] | Impossible to measure |
| 45 | ClCH₂―[5-Me,5-(isoxazoline)]―SO₂―CH₂―[pyrazole: 3-CF₃, 5-OCHF₂, 1-Me] | Impossible to measure |

TABLE 60

| Compound No. | Structural formula | Melting point (° C.) or refractive index (nD20) |
|---|---|---|
| 46 | (structure: 5-(chloromethyl)-5-methyl-isoxazoline-SO₂-CH₂-pyrazole with F₃C, F₂HCH₂CO, N-Me substituents) | Impossible to measure |
| 47 | (structure: 5-(chloromethyl)-5-methyl-isoxazoline-SO₂-CH₂-pyrazole with F₃C, EtO₂S, N-Et substituents) | 88-90 |
| 48 | (structure: 5-(chloromethyl)-5-methyl-isoxazoline-SO₂-CH₂-pyrazole with F₂HC, Cl, N-Me substituents) | 80-81 |
| 49 | (structure: 5-(chloromethyl)-5-methyl-isoxazoline-SO₂-CH₂-pyrazole with F₃C, Et, N-Me substituents) | 1.5006 |

PRODUCTION OF INTERMEDIATES

Reference Example 1

Production of 1-methyl-3-trifluoromethyl-1H-pyrazol-5-ol 23.0 g (0.5 M) of monomethylhydrazine and 5 ml of concentrated hydrochloric acid were added into a solution of 92.1 g (0.5 M) of ethyl trifluoroacetoacetate dissolved in 500 ml of ethanol. The mixture was heated and refluxed for 2 days to give rise to a reaction. After the completion of the reaction, the reaction mixture was subjected to reduced pressure distillation to remove the most part of the solvent contained therein. The residue was poured into water and extraction with ethyl acetate was conducted. The resulting organic layer was washed with water and an aqueous sodium chloride solution in this order and then dried over anhydrous magnesium sulfate. The resulting material was subjected to reduced pressure distillation to remove the solvent contained therein. The residue was washed with n-hexane to obtain 60.0 g (yield: 72.2%) of a white powder of 1-methyl-3-trifluoromethyl-1H-pyrazol-5-ol.

Reference Example 2

Production of 5-chloro-1-methyl-3-trifluoromethyl-1H-pyrazol-4-carboaldehyde 360 g (2.31 M) of phosphorus oxychloride was added to 60.0 g (0.76 M) of N,N-dimethylformamide with ice-cooling. Thereto was added, at room temperature, 64.0 g (0.385 M) of 1-methyl-3-trifluoromethyl-1H-pyrazol-5-ol. The mixture was heated and refluxed for 1 hour to give rise to a reaction. After the completion of the reaction, the reaction mixture was poured into water with ice-cooling, and extraction with chloroform was conducted. The resulting organic layer was washed with an aqueous sodium hydrogencarbonate solution and an aqueous sodium chloride solution in this order and then dried over anhydrous magnesium sulfate. The resulting solution was subjected to reduced pressure distillation to remove the solvent contained therein. The residue was purified by silica gel column chromatography (eluting solvent: hexane/ethyl acetate mixed solvent) to obtain 60.4 g (yield: 73.4%) of white crystals of 5-chloro-1-methyl-3-trifluoromethyl-1H-pyrazole-4-carboaldehyde.

$^1$H-NMR [CDCl$_3$/TMS, δ (ppm)]: 9.96 (1H, d), 3.96 (3H, s)

Reference Example 3

Production of (5-chloro-1-methyl-3-trifluoromethyl-1H-pyrazol-4-yl)-methanol A solution of 10.0 g (47.0 mmoles) of 5-chloro-1-methyl-3-trifluoromethyl-1H-pyrazole-4-carboaldehyde dissolved in 100 ml of methanol was cooled to 0° C. Thereto was gradually added 2.1 g (56.5 mmoles) of sodium borohydride. The mixture was stirred at room temperature for 2 hours to give rise to a reaction. After the completion of the reaction, the reaction mixture was poured into water and extraction with ethyl acetate was conducted. The resulting organic layer was washed with an aqueous sodium chloride solution and then dried over anhydrous magnesium sulfate. The resulting solution was subjected to reduced pressure distillation to remove the solvent contained therein, to obtain 8.3 g (yield: 82.2%) of (5-chloro-1-methyl-3-trifluoromethyl-1H-pyrazol-4-yl)-methanol.

Reference Example 4

Production of 4-bromomethyl-5-chloro-1-methyl-3-trifluoromethyl-1H-pyrazole

A solution of 8.3 g (38.7 mmoles) of (5-chloro-1-methyl-3-trifluoromethyl-1H-pyrazol-4-yl)-methanol dissolved in 100 ml of diethyl ether was cooled to −10° C. Thereto was added 12.6 g (46.4 mmoles) of phosphorus tribromide. The mixture was stirred at room temperature for 1 hour to give rise to a reaction. After the completion of the reaction, the reaction mixture was poured into ice water and extraction with diethyl ether was conducted. The resulting organic layer was washed with an aqueous sodium chloride solution and then dried over anhydrous magnesium sulfate. The resulting solution was subjected to reduced pressure distillation to remove the solvent contained therein, to obtain 10.7 g (yield: 99.9%) of 4-bromomethyl-5-chloro-1-methyl-3-trifluoromethyl-1H-pyrazole.

Reference Example 5

Production of 1-tert-butyl-3-trifluoromethyl-1H-pyrazol-5-ol 373.8 g (3.0 M) of tert-butylhydrazine hydrochloride and 50 ml of concentrated hydrochloric acid were added to a solution of 552.3 g (3.0 M) of ethyl trifluoroacetoacetate dissolved in 1,500 ml of ethanol. The mixture was heated and refluxed for 2 days to give rise to a reaction. After the completion of the reaction, the reaction mixture was subjected to reduced pressure distillation to remove the most part of the solvent contained therein. The residue was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was washed with n-hexane to obtain 369.0 g (yield: 59.1%) of a white powder of 1-tert-butyl-3-trifluoromethyl-1H-pyrazol-5-ol.

Reference Example 6

Production of 1-tert-butyl-5-chloro-3-trifluoromethyl-1H-pyrazole-4-carboaldehyde 462.0 g (3.0 M) of phosphorus oxychloride was added to 87.7 g (1.2 M) of N,N-dimethylformamide with ice-cooling. Thereto was added, at room temperature, 208.2 g (1.0 M) of 1-tert-butyl-3-trifluoromethyl-1H-pyrazol-5-ol. The mixture was heated and refluxed for 10 hours to give rise to a reaction. After the completion of the reaction, the reaction mixture was poured into water and extraction with chloroform was conducted. The resulting organic layer was washed with water, a 5% aqueous sodium hydroxide solution and water in this order and then dried over anhydrous magnesium sulfate. The resulting solution was subjected to reduced pressure distillation to remove the solvent contained therein. The residue was purified by silica gel column chromatography (eluting solvent: hexane/ethyl acetate mixed solvent) to obtain 131.5 g (yield: 21.7%) of white crystals of 1-tert-butyl-5-chloro-3-trifluoromethyl-1H-pyrazole-4-carboaldehyde.

$^1$H-NMR [CDCl$_3$/TMS, δ (ppm)]: 9.97 (1H, d), 1.76 (9H, s)

Reference Example 7

Production of (1-tert-butyl-5-chloro-3-trifluoromethyl-1H-pyrazol-4-yl)-methanol A solution of 39.9 g (156.9 mmoles) of 1-tert-butyl-5-chloro-3-trifluoromethyl-1H-pyrazole-4-carboaldehyde dissolved in 300 ml of methanol was cooled to 0° C. Thereto was gradually added 6.5 g (172.6 mmoles) of sodium borohydride. The mixture was stirred at room temperature for 3 hours to give rise to a reaction. After the completion of the reaction, the reaction mixture was poured into water and extraction with ethyl acetate was conducted. The resulting organic layer was washed with an aqueous sodium chloride solution and then dried over anhydrous magnesium sulfate. The resulting solution was subjected to reduced pressure distillation to remove the solvent contained therein, to obtain 37.7 g (yield: 93.6%) of (1-tert-butyl-5-chloro-3-trifluoromethyl-1H-pyrazol-4-yl)-methanol.

$^1$H-NMR [CDCl$_3$/TMS, δ (ppm)]: 4.60 (2H, d), 1.72 (9H, s), 1.58 (1H, t)

Reference Example 8

Production of 4-bromomethyl-1-tert-butyl-5-chloro-3-trifluoromethyl-1H-pyrazole A solution of 9.2 g (35.7 mmoles) of (1-tert-butyl-5-chloro-3-trifluoromethyl-1H-pyrazol-4-yl)-methanol dissolved in 100 ml of diethyl ether was cooled to −10° C. Thereto was added 11.6 g (42.9 mmoles) of phosphorus tribromide. The mixture was stirred at room temperature overnight to give rise to a reaction. After the completion of the reaction, the reaction mixture was poured into ice water and extraction with diethyl ether was conducted. The resulting organic layer was washed with an aqueous sodium chloride solution and then dried over anhydrous magnesium sulfate. The resulting solution was subjected to reduced pressure distillation to remove the solvent contained therein, to obtain 10.0 g (yield: 87.3%) of 4-bromomethyl-1-tert-butyl-5-chloro-3-trifluoromethyl-1H-pyra-zole.

Reference Example 9

Production of (1-tert-butyl-5-chloro-3-trifluoromethyl-1H-pyrazol-4-yl)-methanethiol 43.5 g (136.1 mmoles) of 4-bromomethyl-1-tert-butyl-5-chloro-3-trifluoromethyl-1H-pyrazole was added to 300 ml of a N,N-dimethylformamide solution containing 21.8 g (272.2 mmoles) of sodium hydrosulfide hydrate (purity: 70%). The mixture was stirred at room temperature overnight to give rise to a reaction. After the completion of the reaction, the reaction mixture was poured into ice water and extraction with diethyl ether was conducted. The resulting organic layer was washed with an aqueous sodium chloride solution and then dried over anhydrous magnesium sulfate. The resulting solution was subjected to reduced pressure distillation to remove the solvent contained therein, to obtain 32.3 g (yield: 87.0%) of (1-tert-butyl-5-chloro-3-trifluoromethyl-1H-pyrazol-4-yl)-metha-nethiol.

$^1$H-NMR [CDCl$_3$/TMS, δ (ppm)]: 3.65 (2H, d), 1.90 (1H, t), 1.70 (9H, s)

Reference Example 10

Production of 5-bromo-4-hydroxy-6-trifluoromethylpyrimidine 77.5 g (945.0 mmoles) of anhydrous sodium acetate was added, at room temperature, into a solution of 49.2 g (300.0 mmoles) of 4-hydroxy-6-trifluoromethylpyrimidine dissolved in 600 ml of acetic acid. Thereto was gradually added, at 45° C., 50.3 g (315 mmoles) of bromine. The mixture was stirred at the same temperature for 3 hours to give rise to a reaction. After confirmation of the completion of the reaction, the reaction mixture was subjected to reduced pressure distillation to remove the solvent contained therein. The residue was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was washed with n-hexane to obtain 38.9 g (yield: 53.4%) of 5-bromo-4-hydroxy-6-trifluoromethylpyrimidine.

Reference Example 11

Production of 5-bromo-4-chloro-6-trifluoromethylpyrimidine 24.3 g (100.0 mmoles) of 5-bromo-4-hydroxy-6-trifluoromethylpyrimidine was suspended in 18.5 g (120.0 mmoles) of phosphorus oxychloride. The suspension was stirred at 100° C. for 2 hours to give rise to a reaction. After confirmation of the completion of the reaction, the reaction mixture was gradually poured into water and extraction with chloroform was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 21.5 g (yield: 82.4%) of 5-bromo-4-chloro-6-trifluoromethylpyrimidine.

Reference Example 12

Production of 5-bromo-4-ethoxy-6-trifluoromethylpyrimidine 0.94 g (13.77 mmoles) of sodium ethoxide was added at room temperature into a solution of 3.00 g (11.48 mmoles) of 5-bromo-4-chloro-trifluoromethylpyrimidine dissolved in 50 ml of ethanol. The mixture was stirred to give rise to a reaction. After confirmation of the completion of the reaction, the reaction mixture was subjected to reduced pressure distillation to remove the solvent contained therein. The residue was poured into water and extraction with chloroform was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 2.44 g (yield: 82.9%) of 5-bromo-4-ethoxy-6-trifluoromethylpyrimidine.

Reference Example 13

Production of 4-ethoxy-6-trifluoromethylpyrimidine-5-carboaldehyde

A solution of 5.76 g (21.3 mmoles) of 5-bromo-4-ethoxy-6-trifluoromethylpyrimidine dissolved in 250 ml of tetrahydrofuran was cooled to −78° C. Thereinto was dropwise added 22.6 ml of a 1.6 M hexane solution containing 36.1 mM of n-butyl lithium. The mixture was stirred for 40 minutes. Thereto was added 2.7 g (45.1 mmoles) of methyl formate. The mixture was stirred for 1.5 hours to give rise to a reaction. After the completion of the reaction, an aqueous ammonium chloride solution was added and extraction with ether was conducted. The resulting organic layer was washed with an aqueous sodium chloride solution and then dried over anhydrous magnesium sulfate. The resulting solution was subjected to reduced pressure distillation to remove the solvent contained therein. The residue was purified by silica gel column chromatography (eluting solvent: hexane/ethyl acetate mixed solvent) to obtain 3.82 g (yield: 81.6%) of 4-ethoxy-6-trifluoromethylpyrimidine-5-carboaldehyde.

$^1$H-NMR [CDCl$_3$/TMS, δ (ppm)]: 10.41 (1H, s), 8.95 (1H, s), 4.63 (2H, q), 1.48 (3H, t)

Reference Example 14

Production of (4-ethoxy-6-trifluoromethylpyrimidin-5-yl)-methanol

A solution of 3.82 g (17.2 mmoles) of 4-ethoxy-6-trifluoromethylpyrimidine-5-carboaldehyde dissolved in 50 ml of methanol was added, with ice-cooling, into a solution of 1.7 g (45.7 mmoles) of sodium borohydride dissolved in 50 ml of methanol. The mixture was stirred at 0° C. for 1 hour to give rise to a reaction. After the completion of the reaction, the reaction mixture was poured into water and extraction with ethyl acetate was conducted. The resulting organic layer was washed with an aqueous sodium chloride solution and then dried over anhydrous magnesium sulfate. The resulting solution was subjected to reduced pressure distillation to remove the solvent contained therein, to obtain 3.77 g (yield: 97.8%) of (4-ethoxy-6-trifluoromethylpyrimidin-5-yl)-methanol.

$^1$H-NMR [CDCl$_3$/TMS, δ (ppm)]: 8.80 (1H, s), 4.81 (2H, s), 4.59 (2H, q), 2.28 (1H, bR), 1.48 (3H, t)

Reference Example 15

Production of 5-bromomethyl-4-ethoxy-6-trifluoromethylpyrimidine

A solution of 3.77 g (17.0 mmoles) of (4-ethoxy-6-trifluoromethylpyrimidin-5-yl)-methanol dissolved in 50 ml of ether was cooled to 0° C. Thereto was added 2.0 g (7.2 mmoles) of phosphorus tribromide. The mixture was stirred at room temperature for 1 hour. The resulting salt was dissolved in methanol and the solution was stirred for 1 hour to give rise to a reaction. The reaction mixture was poured into water and extraction with ether was conducted. The resulting organic layer was washed with an aqueous sodium chloride solution and then dried over anhydrous magnesium sulfate. The resulting solution was subjected to reduced pressure distillation to remove the solvent contained therein, to obtain a crude product of 5-bromomethyl-4-ethoxy-6-trifluoromethylpyrimidine.

$^1$H-NMR [CDCl$_3$/TMS, δ (ppm)]: 8.79 (1H, s), 4.61 (2H, q), 4.55 (2H, s), 1.49 (3H, t)

Reference Example 16

Production of 1-ethyl-3-trifluoromethyl-1H-pyrazol-5-ol

Into a solution of 55.2 g (300.0 mmoles) of ethyl trifluoroacetoacetate dissolved in 300 ml of ethanol were added 18.0 g (300.0 mmoles) of monoethylhyrazine and 5 ml of concentrated hydrochloric acid. The mixture was heated and refluxed for 2 days to give rise a reaction. After the completion of the reaction, the reaction mixture was subjected to reduced pressure distillation to remove the most part of the solvent contained therein. The residue was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was washed with n-hexane to obtain 35.5 g (yield: 65.7%) of a white powder of 1-ethyl-3-trifluoromethyl-1H-pyrazol-5-ol.

Reference Example 17

Production of 5-chloro-1-ethyl-3-trifluoromethyl-1H-pyrazole-4-carboaldehyde 91.1 g (591.2 mmoles) of phosphorus oxychloride was added to 18.0 g (246.3 mmoles) of N,N-dimethylformamide with ice-cooling. Thereto was added, at room temperature, 35.5 g (197.1 mmoles) of 1-ethyl-3-trifluoromethyl-1H-pyrazol-5-ol. The mixture was heated and refluxed for 3 hours to give rise to a reaction. After the completion of the reaction, the reaction mixture was poured into water with ice-cooling, and extraction with chloroform was conducted. The resulting organic layer was washed with an aqueous sodium hydrogencarbonate solution and an aqueous sodium chloride solution in this order and then dried over anhydrous magnesium sulfate. The resulting solution was subjected to reduced pressure distillation to remove the solvent contained therein. The residue was purified by silica gel column chromatography to obtain a crude product of 5-chloro-1-ethyl-3-trifluoromethyl-1H-pyrazole-4-carboaldehyde.

Reference Example 18

Production of 1-ethyl-5-fluoro-3-trifluoromethyl-1H-pyrazole-4-carboaldehyde 34.3 g (591.3 mmoles) of potassium fluoride (a spray-dried product) was added, at room temperature, into a solution of a crude product of 5-chloro-1-ethyl-3-trifluoromethyl-1H-pyrazole-4-carboaldehyde (equivalent to 197.1 mmoles) dissolved in 100 ml of dimethyl sulfoxide. The mixture was stirred at 100° C. for 3 days to give rise to a reaction. After the completion of the reaction, the reaction mixture was poured into water and extraction with ethyl acetate was conducted. The resulting organic layer was washed with water and an aqueous sodium chloride solution in this order and then dried over anhydrous magnesium sulfate. The resulting solution was subjected to reduced pressure distillation to remove the solvent contained therein. The residue was purified by silica gel column chromatography to obtain 11.1 g (yield: 26.8%) of 1-ethyl-5-fluoro-3-trifluoromethyl-1H-pyrazole-4-carboaldehyde.

$^1$H-NMR [CDCl$_3$/TMS, δ (ppm)]: 9.86 (1H, d), 4.19 (2H, q), 1.52 (3H, t)

Reference Example 19

Production of (1-ethyl-5-fluoro-3-trifluoromethyl-1H-pyrazol-4-yl)-methanol

A solution of 11.1 g (52.8 mmoles) of 1-ethyl-5-fluoro-3-trifluoromethyl-1H-pyrazole-4-carboaldehyde dissolved in 50 ml of methanol was cooled to 0° C. Thereto was gradually added 2.1 g (55.5 mmoles) of sodium borohydride. The mixture was stirred at room temperature for 3 hours to give rise to a reaction. After the completion of the reaction, the reaction mixture was poured into water and extraction with diethyl ether was conducted. The resulting organic layer was washed with an aqueous sodium chloride solution and then dried over anhydrous magnesium sulfate. The resulting solution was subjected to reduced pressure distillation to remove the solvent contained therein, to obtain 9.1 g (yield: 81.3%) of (1-ethyl-5-fluoro-3-trifluoromethyl-1H-pyrazol-4-yl)-methanol.

Reference Example 20

Production of 4-bromomethyl-1-ethyl-5-fluoro-3-trifluoromethyl-1H-pyrazole

A solution of 9.1 g (42.9 mmoles) of (1-ethyl-5-fluoro-3-trifluoromethyl-1H-pyrazol-4-yl)-methanol dissolved in 100 ml of diethyl ether was cooled to −10° C. Thereto was added 12.2 g (45.0 mmoles) of phosphorus tribromide. The mixture was stirred at room temperature overnight to give rise to a reaction. After the completion of the reaction, the reaction mixture was poured into ice water and extraction with diethyl ether was conducted. The resulting organic layer was washed with an aqueous sodium chloride solution and then dried over anhydrous magnesium sulfate. The resulting solution was subjected to reduced pressure distillation to remove the solvent contained therein, to obtain a crude product of 4-bromomethyl-1-ethyl-5-fluoro-3-trifluoromethyl-1H-pyrazole.

Reference Example 21

Production of 5-fluoro-1-methyl-3-trifluoromethyl-1H-pyrazole-4-carboaldehyde 42.0 g (711.9 mmoles) of potassium fluoride was added into a solution of 60.4 g (282.7 mmoles) of 5-chloro-1-methyl-3-trifluoromethyl-1H-pyrazole-4-carboaldehyde dissolved in 700 ml of dimethyl sulfoxide. The mixture was stirred at 120 to 140° C. for 5 hours to give rise to a reaction. After confirmation of the completion of the reaction, the reaction mixture was poured into water and extraction with ethyl acetate was conducted. The resulting organic layer was washed with water and an aqueous sodium chloride solution and then dried over anhydrous magnesium sulfate. The resulting solution was subjected to reduced pressure distillation to remove the solvent contained therein. The residue was purified by silica gel column chromatography (developing solvent: hexane/ethyl acetate mixed solvent) to obtain 36.8 g (yield: 66.0%) of 5-fluoro-1-methyl-3-trifluoromethyl-1H-pyrazole-4-.

Reference Example 22

Production of (5-fluoro-1-methyl-3-trifluoromethyl-1H-pyrazol-4-yl)-methanol

A solution of 36.8 g (187.6 mmoles) of 5-fluoro-1-methyl-3-trifluoromethyl-1H-pyrazole-4-carboaldehyde dissolved in 200 ml of methanol was added, with ice-cooling, into a solution of 3.9 g (102.6 mmoles) of sodium borohydride dissolved in 500 ml of methanol. The mixture was stirred at 0° C. for 30 minutes to give rise to a reaction. After confirmation of the completion of the reaction, the reaction mixture was poured into water and extraction with ethyl acetate was conducted. The resulting organic layer was washed with water and an aqueous sodium chloride solution and then dried over anhydrous magnesium sulfate. The resulting solution was subjected to reduced pressure distillation to remove the solvent contained therein, to obtain 35.4 g (yield: 95.4%) of (5-fluoro-1-methyl-3-trifluoromethyl-1H-pyrazol-4-yl)-methanol.

Reference Example 23

Production of 4-bromomethyl-5-fluoro-1-methyl-3-trifluoromethyl-1H-pyrazole

A solution of 35.4 g (178.7 mmoles) of 5-fluoro-1-methyl-3-trifluoromethyl-1H-pyrazole-4-carboaldehyde dissolved in 500 ml of diethyl ether was cooled to −30° C. Thereto was added 54.0 g (199.5 mmoles) of phosphorus tribromide. The mixture was stirred at room temperature for 12 hours to give rise to a reaction. After confirmation of the completion of the reaction, the reaction mixture was poured into water and extraction with diethyl ether was conducted. The resulting organic layer was washed with water and an aqueous sodium chloride solution and then dried over anhydrous magnesium sulfate. The resulting solution was subjected to reduced pressure distillation to remove the solvent contained therein, to obtain 31.4 g (yield: 80.8%) of 4-bromomethyl-5-fluoro-1-methyl-3-trifluoromethyl-1H-pyrazole.

The herbicide of the present invention contains, as an active ingredient, an isoxazoline derivative represented by the general formula [I].

In using the compound of the present invention as a herbicide, the present compound may be used by itself. It can also be used in the form of a powder, a wettable powder, an emulsion, a flowable agent, fine granules, granules, etc. by mixing with a carrier, a surfactant, a dispersing agent, an auxiliary agent, etc. all generally used in herbicide production.

As the carrier used in herbicide production, there can be mentioned, for example, solid carriers such as talc, bentonite, clay, kaolin, diatomaceous earth, white carbon, vermiculite, calcium carbonate, slaked lime, siliceous sand, ammonium sulfate, urea and the like; and liquid carriers such as isopropyl alcohol, xylene, cyclohexane, methylnaphthalene and the like.

As the surfactant and the dispersing agent, there can be mentioned, for example, metal salts of alkylbenzenesulfonic acids, metal salts of dinaphthylmethanedisulfonic acid, salts of alcohol sulfates, alkylarylsulfonic acid salts, ligninsulfonic acid salts, polyoxyethylene glycol ether, polyoxyethylene alkyl aryl ethers, monoalkylates of polyoxyethylene sorbitan and the like. As the auxiliary agent, there can be mentioned, for example, carboxymethyl cellulose, polyethylene glycol and gum arabic. The present herbicide, when used, is diluted to an appropriate concentration and sprayed or applied directly.

The herbicide of the present invention can be used by post-emergence application, pre-emergence application or water surface application, etc. The amount of the active ingredient used is determined appropriately so as to meet the application purpose. When the present compound is made into a powder or granules, the amount is appropriately determined in a range of 0.01 to 10% by weight, preferably 0.05 to 5% by weight. When the present compound is made into an emulsion or a wettable powder, the amount is appropriately determined in a range of 1 to 50% by weight, preferably 5 to 30% by weight. When the present compound is made into a flowable agent, the amount is appropriately determined in a range of 1 to 40% by weight, preferably 5 to 30% by weight.

The amount of the present herbicide used varies depending upon the kind of the compound used, the target weed, the tendency of weed emergence, the environmental conditions, the form of the herbicide used, etc. When the present herbicide is used per se as in the case of a powder or granules, the amount is appropriately selected in a range of 1 g to 50 kg, preferably 10 g to 10 kg per 1 hectare in terms of the active ingredient. When the present herbicide is used in a liquid form as in the case of an emulsion, a wettable powder or a flowable agent, the amount is appropriately selected in a range of 0.1 to 50,000 ppm, preferably 10 to 10,000 ppm.

The compound of the present invention may be mixed as necessary with an insecticide, a fungicide, other herbicide, a plant growth-regulating agent, a fertilizer, etc.

Next, herbicide formulation from the present compound is described specifically by showing typical examples of herbicide formulation. The kinds of compounds and additives and their compounding ratios are not restricted to those shown below and can be varied widely. In the following description, "parts" refer to parts by weight.

(Formulation 1) Wettable Powder 10 parts of a present invention compound No. 2 were mixed with 0.5 part of polyoxyethylene octylphenyl ether, 0.5 part of a sodium salt of a β-naphthalenesulfonic acid-formalin condensate, 20 parts of diatomaceous earth and 69 parts of clay. The mixture was ground to obtain a wettable powder.

(Formulation 2) Flowable Agent 20 parts of a coarsely ground present invention compound No. 2 were dispersed in 69 parts of water. Thereto were added 4 parts of a sulfate of a polyoxyethylene styrenated phenyl ether, 7 parts of ethylene glycol and 200 ppm, relative to the herbicide produced, of Silicone AF-118N (a product of Asahi Chemical Industry, Co. Ltd.). The resulting mixture was stirred for 30 minutes using a high-speed stirrer and then ground using a wet grinder to obtain a flowable agent.

(Formulation 3) Emulsion

To 30 parts of a present invention compound No. 2 were added 60 parts of an equal volume mixture of xylene and isophorone and 10 parts of a surfactant mixture of a polyoxyethylene sorbitan alkylate, a polyoxyethylene alkylaryl polymer and an alkylaryl sulfonate. The resulting mixture was stirred sufficiently to obtain an emulsion.

Formulation 4) Granules 10 parts of water was added to 10 parts of a present invention compound No. 2, 80 parts of an extender which was a 1:3 mixture of talc and bentonite, 5 parts of white carbon and 5 parts of a surfactant mixture of a polyoxyethylene sorbitan alkylate, a polyoxyethylene alkylaryl polymer and an alkylaryl sulfonate. The resulting mixture was kneaded sufficiently to form a paste. The paste was extruded through the eyes (diameter: 0.7 mm) of a sieve. The extrudate was dried and cut into a length of 0.5 to 1 mm to obtain granules.

Next, Application Examples of the present herbicide are described to show the effect of the present compound.

Application Example 1

Test For Herbicidal Effect By Paddy Field Pre-Emergence Treatment

A paddy field soil was filled in a plastic pot of 100 cm$^2$ and subjected to puddling. Then, seeds of *Echinochloa oryzicola* Vasing. and *Monochoria vaginalis* (Murm. f.) Presl var. *plantaginea* (Roxb.) Solms-Laub. were sowed and water was filled in a depth of 3 cm. Next day, wettable powders produced in accordance with the Formulation 1 were diluted with water and dropped on the water surface. The application amount of each wettable powder was 1,000 g per 1 hectare in terms of the active ingredient. Then, breeding was made in a greenhouse, and the herbicidal effect of each wettable powder was examined at the 21st day from the treatment in accordance with the standard shown in Table 61. The results are shown in Table 62.

TABLE 61

| Index | Herbicidal effect (extent of growth inhibition) and phytotoxicity |
|---|---|
| 5 | A herbicidal effect or phytotoxicity of 90% or more |
| 4 | A herbicidal effect or phytotoxicity of 70% to less than 90% |
| 3 | A herbicidal effect or phytotoxicity of 50% to less than 70% |
| 2 | A herbicidal effect or phytotoxicity of 30% to less than 50% |
| 1 | A herbicidal effect or phytotoxicity of 10% to less than 30% |
| 0 | A herbicidal effect or phytotoxicity of 0% to less than 10% |

TABLE 62

| Comp. No | Active ingredient (g/ha) | *Echinochloa oryzicola* Vasing | *Monochoria vaginalis* (Burm. f) Presl Var. *plantaginea* (Roxb.) Solms-Laub. |
|---|---|---|---|
| 2 | 1000 | 5 | 5 |

Application Example 2

Test For Herbicidal Effect By Upland Field Pre-Emergence Treatment

An upland field soil was filled in a plastic pot of 80 cm$^2$. Seeds of *Echinochloa crus-galli* (L.) Beauv. var. *crus-galli* and *Setaria viridis* (L.) Beauv. were sowed, followed by covering with the same soil. Wettable powders produced in accordance with the Formulation 1 were diluted with water and sprayed uniformly on the soil surface using a small sprayer, in an amount of 1,000 liters per 1 hectare so that the amount of each active ingredient became 1,000 g per 1 hectare. Then, breeding was made in a greenhouse, and the herbicidal effect of each wettable powder was examined at the 21st day from the treatment in accordance with the standard shown in Table 61. The results are shown in Table 63.

TABLE 63

| Comp. No | Active ingredient (g/ha) | *Echinochloa crus-galli* (L.) Beauv. Var. *crus-galli* | *Setaria viridis* (L.) Beauv. |
|---|---|---|---|
| 2 | 1000 | 5 | 5 |

Application Example 3

Test For Herbicidal Effect By Upland Foliage Treatment

A sand was filled in a plastic pot of 80 cm$^2$. Seeds of *Echinochloa crus-galli* (L.) Beauv. var. *crus-galli* and *Setaria viridis* (L.) Beauv. were sowed. Breeding was made in a greenhouse for 2 weeks. Wettable powders produced in accordance with the Formulation 1 were diluted with water and sprayed on the whole foliage of plants from above the plants using a small sprayer in an amount of 1,000 liters per 1 hectare so that the amount of each active ingredient became 1,000 g per 1 hectare. Then, breeding was made in the greenhouse, and the herbicidal effect of each wettable powder was examined at the 14th day from the treatment in accordance with the standard shown in Table 61. The results are shown in Table 64.

TABLE 64

| Comp. No | Active ingredient (g/ha) | *Echinochloa crus-galli* (L.) Beauv. Var. *crus-galli* | *Setaria viridis* (L.) Beauv. |
|---|---|---|---|
| 40 | 1000 | 5 | 5 |

INDUSTRIAL APPLICABILITY

The compound represented by the general formula [I] according to the present invention shows an excellent herbicidal effect over a wide period from before germination to growth, to various weeds causing problems in upland fields, for example, broadleaf weeds [e.g. *Polygonum lapathifolium* L. subsp. *nodosum* (Pers.) Kitam., *Amaranthus viridis* L., *Chenopodium album* L., *Stellaria media* (L.) Villars, *Abutilon theophrasti* Medik., *Sida spinosa, Sesbaria exaltata, Ipomoea* spp. and *Xanthium strumarium* L.], perennial or annual cyperaceous weeds [e.g. *Cyperus rotundus* L., *Cyperus esculentus, Kyllinga brevifolia* Rottb. subsp. *leiolepis* (Fraxch. et Savat.) T. Koyama, *Cyperus microiria* Steud., and *Cyperus iria* L.], and Granineous weeds [e.g. *Echinochloa crus-galli* (L.) Beauv. var. *crus-galli, Digitaria ciliaris* (Retz.) Koeler, *Setaria viridis* (L.) Beauv., *Poa annua* L., *Sorghum halepense* (L.) Pers., *Alopecurus aequalis* Sobol. var. *amurensis* (Komar.) Ohwi, and *Avena fatua* L.]. Further, the present compound shows a herbicidal effect also to weeds emerging in paddy fields, i.e. annual weeds [e.g. *Echinochloa oryzicola* Vasing., *Cyperus difformis* L., and *Monochoria vaginalis* (Burm. f.) Presl. var. *plantaginea* (Roxb.) Solms-Laub.] and perennial weeds [e.g. *Sagittaria trifolia* L., *Sagittaria pygmaea* Miq., *Cyperus serotinus* Rottb., *Eleocharis kuroguwai* Ohwi, *Scirpus juncoides* Roxb. subsp. *hotarui* (Ohwi) T. Koyama and *Alisma canaliculatum*].

The herbicide of the present invention has high safety to crops, particularly to rice, wheat, barley, corn, grain sorghum, soybean, cotton, sugar beet, etc.

The invention claimed is:

1. An isoxazoline compound having the following formula and salts thereof:

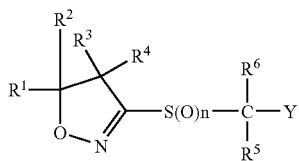

[I]

wherein:
$R^1$ is a chloromethyl group;
$R^2$ is a methyl group;
$R^3$, $R^4$, $R^5$ and $R^6$ are each a hydrogen atom;
Y is a pyrazolyl group or a pyrazolyl group substituted with one to three of the same or different groups selected from the following substituent group a;
n is 2;
wherein when the pyrazolyl group is substituted at two adjacent positions with two alkyl groups which may form a 5- to 8-membered ring;
wherein substituent group α is hydroxyl group; halogen atoms; C1 to C10 alkyl groups; C1 to C10 alkyl groups each mono-substituted with a group selected from the following substituent group β, C1 to C4 haloalkyl groups; C3 to C8 cycloalkyl groups; C1 to C10 alkoxy groups; C1 to C4 haloalkoxy groups; C3 to C8 cycloalkyloxy groups; C1 to C10 alkylthio groups; C1 to C4 haloalkylthio groups; C2 to C6 alkenyl groups; C2 to C6 alkynyl groups; C1 to C10 alkylsulfinyl groups; C1 to C10 alkylsulfonyl groups; C1 to C4 haloalkylsulfinyl groups; C1 to C4 haloalkylsulfonyl groups; C1 to C10 alkylsulfonyloxy groups; C1 to C4 haloalkylsulfonyloxy groups; or cyano group;
wherein substitutent group β is C3 to C8 cycloalkyl groups or C1 to C10 alkoxy groups.

2. An isoxazoline compound or a salt thereof according to claim 1, wherein Y is a pyrazol-4-yl group.

3. An isoxazoline compound or a salt thereof according to claim 2, wherein the pyrazol-4-yl group is substituted at the 3- and 5-positions with a group selected from the substituent group α and at the 1-position with a hydrogen atom, a C1 to C10 alkyl group, a C1 to C10 alkyl group mono-substituted with a group selected from the substituent group β, a C1 to C4 haloalkyl group, a C3 to C8 cycloalkyl group, a C2 to C6 alkenyl group, a C2 to C6 alkynyl group.

4. A herbicide containing, as an active ingredient, an isoxazoline compound or a salt thereof according to claim 1.

5. A herbicide containing, as an active ingredient, an isoxazoline compound or a salt thereof according to claim 2.

6. A herbicide containing, as an active ingredient, an isoxazoline compound or a salt thereof according to claim 3.

* * * * *

UNITED STATES PATENT AND TRADEMARK OFFICE
CERTIFICATE OF CORRECTION

PATENT NO. : 7,875,606 B2
APPLICATION NO. : 10/480376
DATED : January 25, 2011
INVENTOR(S) : Masao Nakatani et al.

It is certified that error appears in the above-identified patent and that said Letters Patent is hereby corrected as shown below:

IN THE CLAIMS:

Column 114, line 7 (claim 1, line 10) delete "a" and insert --$\alpha$--

Signed and Sealed this
Eighth Day of March, 2011

David J. Kappos
*Director of the United States Patent and Trademark Office*